(12) United States Patent
Alt

(10) Patent No.: US 7,625,410 B2
(45) Date of Patent: Dec. 1, 2009

(54) STENT DEVICE AND METHOD

(75) Inventor: Eckhard Alt, Otttobrunn (DE)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 11/338,452

(22) Filed: Jan. 23, 2006

(65) Prior Publication Data
US 2006/0122690 A1 Jun. 8, 2006

Related U.S. Application Data

(63) Continuation of application No. 10/443,266, filed on May 22, 2003, now Pat. No. 7,011,680, which is a continuation of application No. 09/847,626, filed on May 2, 2001, now Pat. No. 6,613,083.

(51) Int. Cl.
*A61F 2/06* (2006.01)
(52) U.S. Cl. ........................................................ 623/42
(58) Field of Classification Search ....... 623/1.42–1.54, 623/1.13, 1.15
See application file for complete search history.

(56) References Cited

U.S. PATENT DOCUMENTS

| | | |
|---|---|---|
| 2,914,563 A | 11/1959 | Allen et al. |
| 3,010,965 A | 11/1961 | Elpem |
| 3,168,565 A | 2/1965 | Palopoli et al. |
| 3,279,996 A | 10/1966 | Long et al. |
| 3,288,806 A | 11/1966 | Dewald et al. |
| 3,445,473 A | 5/1969 | Ruschig et al. |
| 3,526,005 A | 9/1970 | Bokros et al. |
| 3,634,517 A | 1/1972 | Palopoli et al. |
| 3,738,365 A | 6/1973 | Schulte |
| 3,879,516 A | 4/1975 | Wolvek |
| 3,932,627 A | 1/1976 | Margraf |
| 3,940,422 A | 2/1976 | Harita et al. |
| 3,952,334 A | 4/1976 | Bokros et al. |
| 4,070,484 A | 1/1978 | Harita et al. |
| 4,093,709 A | 6/1978 | Choi et al. |
| 4,133,814 A | 1/1979 | Jones et al. |
| 4,205,685 A | 6/1980 | Yoshida et al. |
| 4,219,520 A | 8/1980 | Kline |
| 4,219,656 A | 8/1980 | Press et al. |
| 4,221,785 A | 9/1980 | Sorenson |
| 4,230,862 A | 10/1980 | Suarez et al. |
| 4,235,988 A | 11/1980 | Fildes et al. |
| 4,239,778 A | 12/1980 | Venton et al. |
| 4,282,246 A | 8/1981 | Holland |
| 4,287,190 A | 9/1981 | Boettcher et al. |

(Continued)

FOREIGN PATENT DOCUMENTS

AU 31079/93 12/1995

(Continued)

OTHER PUBLICATIONS

"Breast Cancer Prevention Trial Should Resume, ODAC Says", *The Breast Cancer Letter*, 20, 4-5, (Jun. 17, 1994).

(Continued)

*Primary Examiner*—Alvin J Stewart
(74) *Attorney, Agent, or Firm*—Vidas, Arrett & Steinkraus

(57) ABSTRACT

A stent for delivering a therapeutic dose of the immnuosupressant tacrolimus is disclosed.

20 Claims, 1 Drawing Sheet

U.S. PATENT DOCUMENTS

| | | | |
|---|---|---|---|
| 4,292,965 A | 10/1981 | Nash et al. | |
| 4,300,244 A | 11/1981 | Bokros | |
| 4,307,111 A | 12/1981 | Crawley | |
| 4,310,523 A | 1/1982 | Neumann | |
| 4,315,028 A | 2/1982 | Scheinberg | |
| 4,317,915 A | 3/1982 | Confalone et al. | |
| 4,323,707 A | 4/1982 | Suarez et al. | |
| 4,332,791 A | 6/1982 | Raaf et al. | |
| 4,339,429 A | 7/1982 | Raaf et al. | |
| 4,380,635 A | 4/1983 | Peters | |
| 4,382,143 A | 5/1983 | Shepherd | |
| 4,389,330 A | 6/1983 | Tice et al. | |
| 4,418,068 A | 11/1983 | Jones | |
| 4,428,963 A | 1/1984 | Confalone et al. | |
| 4,440,754 A | 4/1984 | Sorenson | |
| 4,442,119 A | 4/1984 | Magarian et al. | |
| 4,485,096 A | 11/1984 | Bell | |
| 4,485,097 A | 11/1984 | Bell | |
| 4,487,780 A | 12/1984 | Scheinberg | |
| 4,491,574 A | 1/1985 | Seifter et al. | |
| 4,512,762 A | 4/1985 | Spears | |
| 4,536,516 A | 8/1985 | Harper et al. | |
| 4,555,402 A | 11/1985 | Matsuda et al. | |
| 4,577,636 A | 3/1986 | Spears | |
| 4,605,644 A | 8/1986 | Foker | |
| 4,613,665 A | 9/1986 | Larm | |
| 4,629,694 A | 12/1986 | Harpel | |
| 4,655,771 A | 4/1987 | Wallsten | |
| 4,656,083 A | 4/1987 | Hoffman et al. | |
| 4,657,928 A | 4/1987 | Sorenson | |
| 4,664,097 A | 5/1987 | McGrath et al. | |
| 4,670,428 A | 6/1987 | Sorenson | |
| 4,675,189 A | 6/1987 | Kent et al. | |
| 4,678,466 A | 7/1987 | Rosenwald | |
| 4,687,482 A | 8/1987 | Hanson | |
| 4,689,046 A | 8/1987 | Bokros | |
| 4,696,949 A | 9/1987 | Toivola et al. | |
| 4,705,647 A | 11/1987 | Yamaguchi et al. | |
| 4,732,763 A | 3/1988 | Beck et al. | |
| 4,733,665 A | 3/1988 | Palmaz | |
| 4,739,762 A | 4/1988 | Palmaz | |
| 4,744,981 A | 5/1988 | Pavanasasivam | |
| 4,748,982 A | 6/1988 | Horzewski et al. | |
| 4,753,652 A | 6/1988 | Langer et al. | |
| 4,757,059 A | 7/1988 | Sorenson | |
| 4,758,554 A | 7/1988 | Sorenson et al. | |
| 4,758,555 A | 7/1988 | Sorenson | |
| 4,760,051 A | 7/1988 | Pickart | |
| 4,762,129 A | 8/1988 | Bonzel | |
| 4,767,758 A | 8/1988 | Breccia et al. | |
| 4,768,507 A | 9/1988 | Fischell et al. | |
| 4,776,337 A | 10/1988 | Palmaz | |
| 4,786,500 A | 11/1988 | Wong | |
| 4,793,348 A | 12/1988 | Palmaz | |
| 4,824,436 A | 4/1989 | Wolinsky | |
| 4,824,661 A | 4/1989 | Wagner | |
| 4,826,672 A | 5/1989 | Milius et al. | |
| 4,835,002 A | 5/1989 | Wolf et al. | |
| RE32,944 E | 6/1989 | Harita et al. | |
| 4,839,155 A | 6/1989 | McCague | |
| 4,840,939 A | 6/1989 | Leveen et al. | |
| 4,853,377 A | 8/1989 | Pollack | |
| 4,859,585 A | 8/1989 | Sonnenschein et al. | |
| 4,867,973 A | 9/1989 | Goers et al. | |
| 4,872,867 A | 10/1989 | Joh et al. | |
| 4,879,225 A | 11/1989 | Morgan, Jr. et al. | |
| 4,879,315 A | 11/1989 | Magarian et al. | |
| 4,886,062 A | 12/1989 | Wiktor | |
| 4,897,255 A | 1/1990 | Fritzberg et al. | |
| 4,900,561 A | 2/1990 | Abdel-Monem et al. | |
| 4,906,452 A | 3/1990 | Sivam | |
| 4,916,193 A | 4/1990 | Tang et al. | |
| 4,922,905 A | 5/1990 | Strecker | |
| 4,929,602 A | 5/1990 | Harker et al. | |
| 4,935,415 A | 6/1990 | Nakane et al. | |
| 4,952,607 A | 8/1990 | Sorenson | |
| 4,954,126 A | 9/1990 | Wallsten | |
| 4,956,188 A | 9/1990 | Anderson | |
| 4,959,355 A | 9/1990 | Fischbarg et al. | |
| RE33,403 E | 10/1990 | Stolle et al. | |
| 4,962,091 A | 10/1990 | Eppstein et al. | |
| 4,968,350 A | 11/1990 | Bindschaedler et al. | |
| 4,973,601 A | 11/1990 | Dowd et al. | |
| 4,973,755 A | 11/1990 | Grafe et al. | |
| 4,984,594 A | 1/1991 | Vinegar et al. | |
| 4,990,158 A | 2/1991 | Kaplan et al. | |
| 4,990,538 A | 2/1991 | Harris et al. | |
| 4,994,033 A | 2/1991 | Shockey et al. | |
| 4,994,071 A | 2/1991 | MacGregor | |
| 4,994,384 A | 2/1991 | Prather et al. | |
| 4,996,225 A | 2/1991 | Toivola et al. | |
| 4,997,652 A | 3/1991 | Wong | |
| 4,999,347 A | 3/1991 | Sorenson | |
| 5,002,531 A | 3/1991 | Bonzel | |
| 5,008,279 A | 4/1991 | Franckowiak et al. | |
| 5,009,659 A | 4/1991 | Hamlin | |
| 5,015,578 A | 5/1991 | Schroeder et al. | |
| 5,015,666 A | 5/1991 | Magarian et al. | |
| 5,019,096 A | 5/1991 | Fox, Jr. et al. | |
| 5,019,504 A | 5/1991 | Christen et al. | |
| 5,023,237 A | 6/1991 | Pickart et al. | |
| 5,026,537 A | 6/1991 | Daddona et al. | |
| 5,030,637 A | 7/1991 | Einzig et al. | |
| 5,032,679 A | 7/1991 | Brandley et al. | |
| 5,034,265 A | 7/1991 | Hoffman et al. | |
| 5,037,641 A | 8/1991 | Juhos et al. | |
| 5,040,548 A | 8/1991 | Yock | |
| 5,043,335 A | 8/1991 | Kleinschroth et al. | |
| 5,047,431 A | 9/1991 | Schickaneder et al. | |
| 5,049,132 A | 9/1991 | Schaffer et al. | |
| 5,053,033 A | 10/1991 | Clarke et al. | |
| 5,053,048 A | 10/1991 | Pinchuk et al. | |
| 5,059,166 A | 10/1991 | Fischell et al. | |
| 5,061,273 A | 10/1991 | Yock | |
| 5,061,275 A | 10/1991 | Wallsten et al. | |
| 5,064,435 A | 11/1991 | Porter | |
| 5,066,789 A | 11/1991 | Srinivasa et al. | |
| 5,073,633 A | 12/1991 | Schroeder et al. | |
| 5,075,321 A | 12/1991 | Schreiber | |
| 5,082,834 A | 1/1992 | Sorensen | |
| 5,092,877 A | 3/1992 | Pinchuk | |
| 5,093,330 A | 3/1992 | Caravatti et al. | |
| 5,098,903 A | 3/1992 | Magarian et al. | |
| 5,099,504 A | 3/1992 | Pettit | |
| 5,100,885 A | 3/1992 | Abrams et al. | |
| 5,102,402 A | 4/1992 | Dror et al. | |
| 5,102,417 A | 4/1992 | Palmaz | |
| 5,108,989 A | 4/1992 | Amento et al. | |
| 5,112,305 A | 5/1992 | Barath et al. | |
| 5,114,719 A | 5/1992 | Sabel et al. | |
| 5,114,847 A | 5/1992 | Jungfer et al. | |
| 5,116,864 A | 5/1992 | March et al. | |
| 5,118,791 A | 6/1992 | Burnier et al. | |
| 5,120,535 A | 6/1992 | Marguardt et al. | |
| 5,126,348 A | 6/1992 | McMurray | |
| 5,140,012 A | 8/1992 | McGovern et al. | |
| 5,145,684 A | 9/1992 | Liversidge et al. | |
| 5,145,838 A | 9/1992 | Pickart | |
| 5,163,952 A | 11/1992 | Froix | |
| 5,166,143 A | 11/1992 | Ondetti et al. | |
| 5,166,191 A | 11/1992 | Cronin et al. | |
| 5,167,960 A | 12/1992 | Ito et al. | |
| 5,171,217 A | 12/1992 | March et al. | |
| 5,175,235 A | 12/1992 | Domb et al. | |

| Patent | Date | Inventor |
|---|---|---|
| 5,176,617 A | 1/1993 | Fischell et al. |
| 5,180,366 A | 1/1993 | Woods |
| 5,180,376 A | 1/1993 | Fischell |
| 5,182,317 A | 1/1993 | Winters et al. |
| 5,185,260 A | 2/1993 | Crissman et al. |
| 5,185,408 A | 2/1993 | Tang et al. |
| 5,189,046 A | 2/1993 | Burch et al. |
| 5,189,212 A | 2/1993 | Ruenitz |
| 5,192,525 A | 3/1993 | Yang et al. |
| 5,195,984 A | 3/1993 | Schatz |
| 5,199,939 A | 4/1993 | Dake et al. |
| 5,199,951 A | 4/1993 | Spears |
| 5,208,019 A | 5/1993 | Hanson et al. |
| 5,208,238 A | 5/1993 | King |
| 5,211,940 A | 5/1993 | Ishiguro et al. |
| 5,213,576 A | 5/1993 | Abiuso et al. |
| 5,213,580 A | 5/1993 | Slepian et al. |
| 5,216,021 A | 6/1993 | Sorenson |
| 5,216,024 A | 6/1993 | Markaverich et al. |
| 5,216,126 A | 6/1993 | Cox et al. |
| 5,219,548 A | 6/1993 | Yang et al. |
| 5,221,620 A | 6/1993 | Purchio et al. |
| 5,222,971 A | 6/1993 | Willard et al. |
| 5,226,430 A | 7/1993 | Spears et al. |
| 5,226,913 A | 7/1993 | Pinchuk |
| 5,229,495 A | 7/1993 | Ichijo et al. |
| 5,232,444 A | 8/1993 | Just et al. |
| 5,232,911 A | 8/1993 | Vidal et al. |
| 5,234,456 A | 8/1993 | Silverstrini |
| 5,234,957 A | 8/1993 | Mantelle |
| 5,238,714 A | 8/1993 | Wallace et al. |
| 5,238,950 A | 8/1993 | Clader et al. |
| 5,242,397 A | 9/1993 | Barath et al. |
| 5,248,764 A | 9/1993 | Flanagan et al. |
| 5,252,579 A | 10/1993 | Skotnicki et al. |
| 5,254,594 A | 10/1993 | Niikura et al. |
| 5,258,020 A | 11/1993 | Froix |
| 5,260,224 A | 11/1993 | Stossel et al. |
| 5,262,319 A | 11/1993 | Iwata et al. |
| 5,262,451 A | 11/1993 | Winters et al. |
| 5,268,358 A | 12/1993 | Fretto et al. |
| 5,268,455 A | 12/1993 | Cianciolo |
| 5,270,047 A | 12/1993 | Kauffman et al. |
| 5,280,016 A | 1/1994 | Conrad et al. |
| 5,280,040 A | 1/1994 | Labroo et al. |
| 5,280,109 A | 1/1994 | Miyazono et al. |
| 5,282,785 A | 2/1994 | Shapland et al. |
| 5,282,823 A | 2/1994 | Schwartz et al. |
| 5,283,257 A | 2/1994 | Gregory et al. |
| 5,284,763 A | 2/1994 | Derynk et al. |
| 5,284,869 A | 2/1994 | Bisaccia et al. |
| 5,288,711 A | 2/1994 | Mitchell et al. |
| 5,288,735 A | 2/1994 | Trager et al. |
| 5,290,271 A | 3/1994 | Jernberg |
| 5,292,802 A | 3/1994 | Rhee et al. |
| 5,296,492 A | 3/1994 | Shiozawa et al. |
| 5,302,584 A | 4/1994 | Kao et al. |
| 5,304,121 A | 4/1994 | Sahatjian |
| 5,304,325 A | 4/1994 | Kaufman et al. |
| 5,304,541 A | 4/1994 | Purchio et al. |
| 5,308,622 A | 5/1994 | Casscells et al. |
| 5,308,862 A | 5/1994 | Ohlstein et al. |
| 5,308,889 A | 5/1994 | Rhee et al. |
| 5,314,679 A | 5/1994 | Lewis et al. |
| 5,316,766 A | 5/1994 | Baldus et al. |
| 5,318,779 A | 6/1994 | Hakamatsuka et al. |
| 5,324,736 A | 6/1994 | Magarin et al. |
| 5,324,739 A | 6/1994 | Germick et al. |
| 5,326,757 A | 7/1994 | Demopoulos |
| 5,328,471 A | 7/1994 | Slepian |
| 5,332,576 A | 7/1994 | Mantelle |
| 5,332,584 A | 7/1994 | Scher et al. |
| 5,338,770 A | 8/1994 | Winters et al. |
| 5,340,925 A | 8/1994 | Lioubin et al. |
| 5,342,348 A | 8/1994 | Kaplan |
| 5,342,926 A | 8/1994 | Hattner |
| 5,344,926 A | 9/1994 | Murakata et al. |
| 5,346,702 A | 9/1994 | Na et al. |
| 5,346,897 A | 9/1994 | King |
| 5,346,993 A | 9/1994 | Miyazono et al. |
| 5,354,562 A | 10/1994 | Platz et al. |
| 5,354,774 A | 10/1994 | Deckelbaum et al. |
| 5,354,801 A | 10/1994 | O'toole |
| 5,356,433 A | 10/1994 | Rowland et al. |
| 5,356,713 A | 10/1994 | Charmot et al. |
| 5,358,844 A | 10/1994 | Stossel et al. |
| 5,362,424 A | 11/1994 | Lee et al. |
| 5,362,478 A | 11/1994 | Desai et al. |
| 5,362,718 A | 11/1994 | Skotnicki et al. |
| 5,364,632 A | 11/1994 | Benita |
| 5,364,843 A | 11/1994 | King |
| 5,378,475 A | 1/1995 | Smith et al. |
| 5,380,299 A | 1/1995 | Fearnot et al. |
| 5,380,716 A | 1/1995 | Conrad et al. |
| 5,383,928 A | 1/1995 | Scott et al. |
| 5,384,332 A | 1/1995 | Fontana |
| 5,385,935 A | 1/1995 | Tamai et al. |
| 5,387,680 A | 2/1995 | Nelson |
| 5,389,670 A | 2/1995 | Fontana |
| 5,391,378 A | 2/1995 | Sanderson |
| 5,391,557 A | 2/1995 | Cullinan et al. |
| 5,393,763 A | 2/1995 | Black et al. |
| 5,393,772 A | 2/1995 | Yu et al. |
| 5,393,785 A | 2/1995 | Labrie et al. |
| 5,395,610 A | 3/1995 | King |
| 5,395,842 A | 3/1995 | Labrie et al. |
| 5,399,352 A | 3/1995 | Hanson |
| 5,401,730 A | 3/1995 | Sauvage et al. |
| 5,407,609 A | 4/1995 | Tice et al. |
| 5,407,658 A | 4/1995 | Hattner |
| 5,411,967 A | 5/1995 | Kao et al. |
| 5,411,988 A | 5/1995 | Bockow et al. |
| 5,415,619 A | 5/1995 | Lee et al. |
| 5,416,205 A | 5/1995 | della Valle et al. |
| 5,418,252 A | 5/1995 | Williams |
| 5,419,760 A | 5/1995 | Narciso, Jr. |
| 5,420,243 A | 5/1995 | Ogawa et al. |
| 5,421,955 A | 6/1995 | Lau et al. |
| 5,422,362 A | 6/1995 | Vincent et al. |
| 5,423,885 A | 6/1995 | Williams |
| 5,424,331 A | 6/1995 | Shlyankevich |
| 5,426,123 A | 6/1995 | Fontana |
| 5,429,618 A | 7/1995 | Keogh |
| 5,429,634 A | 7/1995 | Narcisco et al. |
| 5,434,166 A | 7/1995 | Glasebrook |
| 5,436,243 A | 7/1995 | Sachs et al. |
| 5,439,689 A | 8/1995 | Hendrickson et al. |
| 5,439,923 A | 8/1995 | Cullinan |
| 5,439,931 A | 8/1995 | Sales |
| 5,441,734 A | 8/1995 | Reichert et al. |
| 5,441,947 A | 8/1995 | Dodge et al. |
| 5,441,964 A | 8/1995 | Bryant et al. |
| 5,441,965 A | 8/1995 | Sall et al. |
| 5,441,966 A | 8/1995 | Dodge |
| 5,441,986 A | 8/1995 | Thompson |
| 5,443,458 A | 8/1995 | Eury |
| 5,444,164 A | 8/1995 | Purchio et al. |
| 5,445,941 A | 8/1995 | Yang |
| 5,446,053 A | 8/1995 | Keohane |
| 5,446,070 A | 8/1995 | Mantelle |
| 5,447,724 A | 9/1995 | Helmus et al. |
| 5,447,941 A | 9/1995 | Zuckerman |
| 5,449,382 A | 9/1995 | Dayton |
| 5,451,233 A | 9/1995 | Yock |
| 5,451,414 A | 9/1995 | Steward |
| 5,451,589 A | 9/1995 | Dodge |

| | | | | | | |
|---|---|---|---|---|---|---|
| 5,451,590 A | 9/1995 | Dodge | | 5,534,527 A | 7/1996 | Black et al. |
| 5,451,603 A | 9/1995 | Piggott | | 5,538,892 A | 7/1996 | Donahoe et al. |
| 5,453,436 A | 9/1995 | Ohlstein | | 5,541,174 A | 7/1996 | Sorenson |
| 5,453,442 A | 9/1995 | Bryant et al. | | 5,543,155 A | 8/1996 | Fekete et al. |
| 5,453,492 A | 9/1995 | Butzow et al. | | 5,545,208 A | 8/1996 | Wolff et al. |
| 5,455,275 A | 10/1995 | Fontana | | 5,545,409 A | 8/1996 | Laurencin et al. |
| 5,457,113 A | 10/1995 | Cullinan et al. | | 5,545,569 A | 8/1996 | Grainger et al. |
| 5,457,116 A | 10/1995 | Black et al. | | 5,551,954 A | 9/1996 | Buscemi et al. |
| 5,457,117 A | 10/1995 | Black et al. | | 5,552,415 A | 9/1996 | May |
| 5,458,568 A | 10/1995 | Racchini et al. | | 5,552,433 A | 9/1996 | Bryant et al. |
| 5,460,807 A | 10/1995 | Cardin et al. | | 5,554,182 A | 9/1996 | Dinh et al. |
| 5,461,064 A | 10/1995 | Cullinan | | 5,556,876 A | 9/1996 | Bryant et al. |
| 5,461,065 A | 10/1995 | Black et al. | | 5,562,922 A | 10/1996 | Lambert |
| 5,462,925 A | 10/1995 | Ogawa et al. | | 5,563,054 A | 10/1996 | Briggs et al. |
| 5,462,937 A | 10/1995 | Cullinan et al. | | 5,563,145 A | 10/1996 | Failli et al. |
| 5,462,949 A | 10/1995 | Jones et al. | | 5,563,146 A | 10/1996 | Morris et al. |
| 5,462,950 A | 10/1995 | Fontana | | 5,567,713 A | 10/1996 | Cullinan et al. |
| 5,462,966 A | 10/1995 | Sofia | | 5,569,463 A | 10/1996 | Helmus et al. |
| 5,464,450 A | 11/1995 | Buscemi et al. | | 5,571,166 A | 11/1996 | Dinh et al. |
| 5,464,650 A | 11/1995 | Berg et al. | | 5,571,714 A | 11/1996 | Dasch et al. |
| 5,466,810 A | 11/1995 | Godfrey | | 5,571,808 A | 11/1996 | Leeds |
| 5,468,746 A | 11/1995 | Casagrande et al. | | 5,574,047 A | 11/1996 | Bumol et al. |
| 5,470,876 A | 11/1995 | Proctor | | 5,576,345 A | 11/1996 | Mansson et al. |
| 5,470,883 A | 11/1995 | Stromberg | | 5,578,075 A | 11/1996 | Dayton |
| 5,472,985 A | 12/1995 | Grainger et al. | | 5,578,703 A | 11/1996 | Ichijo et al. |
| 5,474,563 A | 12/1995 | Myler et al. | | 5,580,898 A | 12/1996 | Trojanowski et al. |
| 5,478,847 A | 12/1995 | Draper | | 5,583,153 A | 12/1996 | Brahn |
| 5,478,860 A | 12/1995 | Wheeler et al. | | 5,591,224 A | 1/1997 | Schwartz et al. |
| 5,480,888 A | 1/1996 | Kodama et al. | | 5,591,227 A | 1/1997 | Dinh et al. |
| 5,480,903 A | 1/1996 | Piggott et al. | | 5,595,722 A | 1/1997 | Grainger et al. |
| 5,480,904 A | 1/1996 | Bryant et al. | | 5,597,578 A | 1/1997 | Brown et al. |
| 5,482,851 A | 1/1996 | Derynck et al. | | 5,599,352 A | 2/1997 | Dinh et al. |
| 5,482,949 A | 1/1996 | Black et al. | | 5,599,844 A | 2/1997 | Grainger et al. |
| 5,482,950 A | 1/1996 | Bryant et al. | | 5,605,696 A | 2/1997 | Eury et al. |
| 5,484,795 A | 1/1996 | Bryant et al. | | 5,605,700 A | 2/1997 | DeGregorio et al. |
| 5,484,796 A | 1/1996 | Bryant et al. | | 5,607,463 A | 3/1997 | Schwartz et al. |
| 5,484,797 A | 1/1996 | Bryant et al. | | 5,609,629 A | 3/1997 | Fearnot et al. |
| 5,484,798 A | 1/1996 | Bryant et al. | | 5,610,166 A | 3/1997 | Singh |
| 5,484,808 A | 1/1996 | Grinell | | 5,610,168 A | 3/1997 | Draper |
| 5,486,357 A | 1/1996 | Narayanan | | 5,616,608 A | 4/1997 | Kinsella et al. |
| 5,489,587 A | 2/1996 | Fontana | | 5,622,975 A | 4/1997 | Singh et al. |
| 5,491,159 A | 2/1996 | Malamas | | 5,624,411 A | 4/1997 | Tuch |
| 5,491,173 A | 2/1996 | Toivola et al. | | 5,626,600 A | 5/1997 | Horzewski et al. |
| 5,492,895 A | 2/1996 | Vlasuk et al. | | 5,629,077 A | 5/1997 | Turnlund et al. |
| 5,492,921 A | 2/1996 | Bryant et al. | | 5,632,840 A | 5/1997 | Campbell |
| 5,492,922 A | 2/1996 | Palkowitz | | 5,635,406 A * | 6/1997 | Grenier et al. ............... 436/536 |
| 5,492,926 A | 2/1996 | Cullinan et al. | | 5,635,489 A | 6/1997 | Haley |
| 5,492,927 A | 2/1996 | Gitter et al. | | 5,637,113 A | 6/1997 | Tartaglia et al. |
| 5,496,346 A | 3/1996 | Horzewski et al. | | 5,639,274 A | 6/1997 | Fischell et al. |
| 5,496,557 A | 3/1996 | Feijen et al. | | 5,639,738 A | 6/1997 | Falk et al. |
| 5,496,581 A | 3/1996 | Yianni et al. | | 5,641,790 A | 6/1997 | Draper |
| 5,496,828 A | 3/1996 | Cullinan | | 5,643,580 A | 7/1997 | Subramanian |
| 5,496,851 A | 3/1996 | Grinnell | | 5,646,160 A | 7/1997 | Morris et al. |
| 5,498,775 A | 3/1996 | Novak et al. | | 5,651,627 A | 7/1997 | Dowzall et al. |
| 5,500,013 A | 3/1996 | Buschemi et al. | | 5,652,259 A | 7/1997 | May |
| 5,504,091 A | 4/1996 | Molnar-Kimber et al. | | 5,656,450 A | 8/1997 | Boyan et al. |
| 5,508,292 A | 4/1996 | Sall et al. | | 5,656,587 A | 8/1997 | Sporn et al. |
| 5,510,077 A | 4/1996 | Dinh et al. | | 5,658,883 A | 8/1997 | Ogawa et al. |
| 5,510,370 A | 4/1996 | Hock et al. | | 5,658,927 A | 8/1997 | Magarian et al. |
| 5,512,055 A | 4/1996 | Domb et al. | | 5,658,951 A | 8/1997 | Magarian et al. |
| 5,512,268 A | 4/1996 | Grinstaff et al. | | 5,660,873 A | 8/1997 | Nikolaychik et al. |
| 5,514,154 A | 5/1996 | Lau et al. | | 5,662,712 A | 9/1997 | Pathak et al. |
| 5,516,781 A | 5/1996 | Morris et al. | | 5,665,728 A | 9/1997 | Morris et al. |
| 5,516,807 A | 5/1996 | Hupe et al. | | 5,667,764 A | 9/1997 | Kopia et al. |
| 5,519,042 A | 5/1996 | Morris et al. | | 5,677,295 A | 10/1997 | Failli et al. |
| 5,521,171 A | 5/1996 | Sorenson | | 5,679,400 A | 10/1997 | Tuch |
| 5,521,172 A | 5/1996 | Bryant et al. | | 5,681,835 A | 10/1997 | Willson |
| 5,521,191 A | 5/1996 | Greenwald | | 5,686,467 A | 11/1997 | Bumol et al. |
| 5,521,198 A | 5/1996 | Zuckerman | | 5,686,476 A | 11/1997 | May |
| 5,523,092 A | 6/1996 | Hanson et al. | | 5,688,813 A | 11/1997 | Sall et al. |
| 5,525,610 A | 6/1996 | Caufield et al. | | 5,688,855 A | 11/1997 | Stoy et al. |
| 5,525,624 A | 6/1996 | Gitter et al. | | 5,693,607 A | 12/1997 | Segrini et al. |
| 5,527,337 A | 6/1996 | Stack et al. | | 5,697,967 A | 12/1997 | Dinh et al. |

| | | | | | | |
|---|---|---|---|---|---|---|
| 5,700,559 A | 12/1997 | Sheu et al. | | 6,241,762 B1 | 6/2001 | Shanley |
| 5,705,477 A | 1/1998 | Sporn et al. | | 6,251,920 B1 | 6/2001 | Grainger et al. |
| 5,705,609 A | 1/1998 | Ruoslahti et al. | | 6,268,390 B1 | 7/2001 | Kunz |
| 5,716,981 A | 2/1998 | Hunter et al. | | 6,273,913 B1 | 8/2001 | Wright et al. |
| 5,722,984 A | 3/1998 | Fischell et al. | | 6,306,421 B1 | 10/2001 | Kunz et al. |
| 5,726,186 A | 3/1998 | Grese | | 6,309,412 B1 | 10/2001 | Lau et al. |
| 5,731,144 A | 3/1998 | Toothman et al. | | 6,309,414 B1 | 10/2001 | Rolando et al. |
| 5,731,200 A | 3/1998 | Ichijo et al. | | 6,358,989 B1 | 3/2002 | Kunz et al. |
| 5,731,424 A | 3/1998 | Toothman et al. | | 6,395,326 B1 | 5/2002 | Castro et al. |
| 5,733,303 A | 3/1998 | Israel et al. | | 6,403,635 B1 | 6/2002 | Kinsella et al. |
| 5,733,925 A | 3/1998 | Kunz et al. | | 6,429,232 B1 | 8/2002 | Kinsella et al. |
| 5,735,897 A | 4/1998 | Buirge | | 6,432,133 B1 | 8/2002 | Lau et al. |
| 5,736,401 A * | 4/1998 | Grenier et al. ................. 436/8 | | 6,443,982 B1 | 9/2002 | Israel et al. |
| 5,747,510 A | 5/1998 | Draper | | 6,461,381 B2 | 10/2002 | Israel et al. |
| 5,749,888 A | 5/1998 | Yock | | 6,476,200 B1 | 11/2002 | Sabatini et al. |
| 5,749,915 A | 5/1998 | Slepian | | 6,485,511 B2 | 11/2002 | Lau et al. |
| 5,767,079 A | 6/1998 | Glaser et al. | | 6,488,694 B1 | 12/2002 | Lau et al. |
| 5,770,609 A | 6/1998 | Grainger et al. | | 6,491,617 B1 | 12/2002 | Ogle et al. |
| 5,773,479 A | 6/1998 | Grainger et al. | | 6,491,938 B2 | 12/2002 | Kunz et al. |
| 5,776,184 A | 7/1998 | Tuch | | 6,492,106 B1 | 12/2002 | Sabatini et al. |
| 5,779,732 A | 7/1998 | Amundson | | 6,497,647 B1 | 12/2002 | Tucker |
| 5,797,898 A | 8/1998 | Santini, Jr. et al. | | 6,515,009 B1 | 2/2003 | Kunz et al. |
| 5,800,507 A | 9/1998 | Schwartz | | 6,527,789 B1 | 3/2003 | Lau et al. |
| 5,811,447 A | 9/1998 | Kunz et al. | | 6,544,544 B2 | 4/2003 | Hunter et al. |
| 5,821,234 A | 10/1998 | Dzau | | 6,544,790 B1 | 4/2003 | Sabatini |
| 5,824,048 A | 10/1998 | Tuch | | 6,555,138 B1 | 4/2003 | Karlsson |
| 5,824,049 A | 10/1998 | Ragheb et al. | | 6,562,065 B1 | 5/2003 | Shanley |
| 5,824,054 A | 10/1998 | Khosravi et al. | | 6,575,993 B1 | 6/2003 | Yock |
| 5,824,647 A | 10/1998 | Postlethwaite et al. | | 6,585,764 B2 | 7/2003 | Wright et al. |
| 5,837,008 A | 11/1998 | Berg et al. | | 6,596,022 B2 | 7/2003 | Lau et al. |
| 5,837,313 A | 11/1998 | Ding et al. | | 6,599,928 B2 | 7/2003 | Kunz et al. |
| 5,843,120 A | 12/1998 | Israel et al. | | 6,613,083 B2 * | 9/2003 | Alt ............................ 623/1.42 |
| 5,847,007 A | 12/1998 | Grainger et al. | | 6,616,690 B2 | 9/2003 | Rolando et al. |
| 5,849,034 A | 12/1998 | Schwartz | | 6,616,765 B1 | 9/2003 | Castro et al. |
| 5,863,285 A | 1/1999 | Coletti | | 6,656,162 B2 | 12/2003 | Santini, Jr. et al. |
| 5,873,904 A | 2/1999 | Ragheb et al. | | 6,656,216 B1 | 12/2003 | Nossainy et al. |
| 5,877,224 A | 3/1999 | Brocchini et al. | | 6,663,881 B2 | 12/2003 | Kunz et al. |
| 5,900,246 A | 5/1999 | Lambert | | 6,689,159 B2 | 2/2004 | Lau et al. |
| 5,902,332 A | 5/1999 | Schatz | | 6,764,507 B2 | 7/2004 | Shanley et al. |
| 5,945,456 A | 8/1999 | Grainger et al. | | 6,776,796 B2 | 8/2004 | Falotico et al. |
| 5,948,639 A | 9/1999 | Ginemo et al. | | 6,783,543 B2 | 8/2004 | Jang |
| 5,972,018 A | 10/1999 | Israel et al. | | 6,808,536 B2 | 10/2004 | Wright et al. |
| 5,980,972 A | 11/1999 | Ding | | 7,011,680 B2 * | 3/2006 | Alt ............................ 623/1.42 |
| 5,981,568 A | 11/1999 | Kunz et al. | | 7,078,495 B1 * | 7/2006 | Kasper et al. ............ 530/389.8 |
| 5,990,095 A | 11/1999 | Falk et al. | | 2002/0013275 A1 | 1/2002 | Kunz et al. |
| 6,001,622 A | 12/1999 | Dedhar et al. | | 2002/0019344 A1 * | 2/2002 | Pershadsingh ................. 514/9 |
| 6,013,099 A | 1/2000 | Dinh et al. | | 2002/0040064 A1 | 4/2002 | Kunz et al. |
| 6,022,866 A | 2/2000 | Falk et al. | | 2002/0086896 A1 | 7/2002 | Kunz et al. |
| 6,036,715 A | 3/2000 | Yock | | 2003/0039675 A1 | 2/2003 | Kunz et al. |
| 6,042,875 A | 3/2000 | Ding et al. | | 2004/0236416 A1 | 11/2004 | Falotico |
| 6,066,167 A | 5/2000 | Lau et al. | | | | |
| 6,074,337 A | 6/2000 | Tucker et al. | | FOREIGN PATENT DOCUMENTS | | |
| 6,074,659 A | 6/2000 | Kunz et al. | | | | |
| 6,086,910 A | 7/2000 | Howard et al. | | CA | 2086642 | 7/1993 |
| 6,087,479 A | 7/2000 | Stamler et al. | | CA | 2079205 | 3/1994 |
| 6,093,221 A | 7/2000 | Kunz et al. | | CA | 2207659 | 6/1996 |
| 6,096,070 A | 8/2000 | Ragheb et al. | | CA | 2231727 | 9/2004 |
| 6,099,499 A | 8/2000 | Ciamacco et al. | | DE | 3 918 736 | 12/1990 |
| 6,099,562 A | 8/2000 | Ding et al. | | DE | 40 22 956 | 2/1992 |
| 6,106,454 A | 8/2000 | Berg et al. | | DE | 4401554 | 8/1994 |
| 6,110,483 A | 8/2000 | Whitbourne et al. | | DE | 4320896 | 1/1995 |
| 6,120,536 A | 9/2000 | Ding et al. | | DE | 4320898 | 1/1995 |
| 6,129,757 A | 10/2000 | Weadock | | DE | 19948126 * | 4/2001 |
| 6,133,242 A | 10/2000 | Zalewski et al. | | EP | 0 002 341 | 6/1979 |
| 6,146,358 A | 11/2000 | Rowe | | EP | 0 024 096 A2 | 2/1981 |
| 6,152,869 A | 11/2000 | Park et al. | | EP | 0 054 168 A1 | 6/1982 |
| 6,168,619 B1 | 1/2001 | Dinh et al. | | EP | 0 095 875 A2 | 12/1983 |
| 6,171,609 B1 | 1/2001 | Kunz | | EP | 0 260 066 B1 | 3/1988 |
| 6,187,370 B1 | 2/2001 | Dinh et al. | | EP | 0 290 012 | 11/1988 |
| 6,187,745 B1 * | 2/2001 | Striker et al. ................. 514/11 | | EP | 0 297 946 A2 | 1/1989 |
| 6,198,016 B1 | 3/2001 | Lucast et al. | | EP | 0 302 034 | 2/1989 |
| 6,203,536 B1 | 3/2001 | Berg et al. | | EP | 0 365 863 B1 | 5/1990 |
| 6,210,393 B1 | 4/2001 | Brisken et al. | | EP | 0 374 044 B1 | 6/1990 |

| | | | | | | |
|---|---|---|---|---|---|---|
| EP | 0 377 526 A2 | 7/1990 | | WO | WO 90/11676 | 10/1990 |
| EP | A 0 430 542 A2 | 11/1990 | | WO | WO 90/12597 | 11/1990 |
| EP | A 0 435 518 | 12/1990 | | WO | WO 90/13293 | 11/1990 |
| EP | 0 411 893 A2 | 2/1991 | | WO | WO 90/13332 A1 | 11/1990 |
| EP | 0 451 202 B1 | 10/1991 | | WO | WO 91/08291 | 6/1991 |
| EP | 0 524 093 | 1/1993 | | WO | WO 91/12779 | 9/1991 |
| EP | 0 577 215 | 1/1993 | | WO | WO 91/15219 | 10/1991 |
| EP | 0 526 102 | 2/1993 | | WO | WO 91/15222 | 10/1991 |
| EP | 0 701 802 A1 | 3/1993 | | WO | WO 91/17731 | 11/1991 |
| EP | 0 542 679 | 5/1993 | | WO | WO 91/17789 A1 | 11/1991 |
| EP | 0 551 182 | 7/1993 | | WO | WO 91/18940 A1 | 12/1991 |
| EP | 0 551 182 A1 | 7/1993 | | WO | WO 92/00330 | 1/1992 |
| EP | 0 566 245 A1 | 10/1993 | | WO | WO 92/06068 | 4/1992 |
| EP | 0 578 998 | 1/1994 | | WO | WO 92/08480 | 5/1992 |
| EP | 0 588 518 A1 | 3/1994 | | WO | WO 92/11872 | 7/1992 |
| EP | 0 623 345 A1 | 5/1994 | | WO | WO 92/11890 | 7/1992 |
| EP | 0 604 022 A1 | 6/1994 | | WO | WO 92/11895 | 7/1992 |
| EP | 0 606 613 | 7/1994 | | WO | WO 92/12717 | 8/1992 |
| EP | 0 619 314 | 10/1994 | | WO | WO 92/13867 | 8/1992 |
| EP | 0 622 076 | 11/1994 | | WO | WO 92/15286 | 9/1992 |
| EP | 0 623 354 A1 | 11/1994 | | WO | WO 92/18546 | 10/1992 |
| EP | 0 629 697 | 12/1994 | | WO | WO 92/19273 | 11/1992 |
| EP | 0 35270 A2 | 1/1995 | | WO | WO 92/19612 | 11/1992 |
| EP | 0 639 577 | 2/1995 | | WO | WO 92/21363 | 12/1992 |
| EP | 0 659 413 A2 | 6/1995 | | WO | WO 93/02065 | 2/1993 |
| EP | 0 659 415 A2 | 6/1995 | | WO | WO 93/04191 | 3/1993 |
| EP | 0 659 418 | 6/1995 | | WO | WO 93/06792 A1 | 4/1993 |
| EP | 0 659 419 A1 | 6/1995 | | WO | WO 93/07748 A2 | 4/1993 |
| EP | 0 659 429 A1 | 6/1995 | | WO | WO 93/09228 | 5/1993 |
| EP | 0 664 121 | 7/1995 | | WO | WO 93/09765 | 5/1993 |
| EP | 0 664 122 | 7/1995 | | WO | WO 93/09790 | 5/1993 |
| EP | 0 664 123 | 7/1995 | | WO | WO 93/09800 | 5/1993 |
| EP | 0 664 124 A1 | 7/1995 | | WO | WO 93/09802 A2 | 5/1993 |
| EP | 0 664 125 | 7/1995 | | WO | WO 93/10808 | 6/1993 |
| EP | 0 664 198 | 7/1995 | | WO | WO 93/11120 | 6/1993 |
| EP | 0 665 015 A2 | 8/1995 | | WO | WO 93/11757 | 6/1993 |
| EP | 0 668 075 A2 | 8/1995 | | WO | WO 93/16724 | 9/1993 |
| EP | 0 670 162 | 9/1995 | | WO | WO 93/17121 | 9/1993 |
| EP | 0 673 936 | 9/1995 | | WO | WO 93/19746 | 10/1993 |
| EP | 0 674 903 | 10/1995 | | WO | WO 93/19769 | 10/1993 |
| EP | 0 675 121 | 10/1995 | | WO | WO 93/24476 | 12/1993 |
| EP | 0 684 259 A1 | 11/1995 | | WO | WO 94/01056 | 1/1994 |
| EP | 0 716 836 A1 | 12/1995 | | WO | WO 94/02595 | 2/1994 |
| EP | 0 691 130 | 1/1996 | | WO | WO 94/03644 | 2/1994 |
| EP | 0 699 673 | 3/1996 | | WO | WO 94/04164 | 3/1994 |
| EP | 0717 041 A1 | 6/1996 | | WO | WO 94/04178 | 3/1994 |
| EP | 0 734 721 A2 | 10/1996 | | WO | WO 94/07529 | 4/1994 |
| EP | 0 747 069 B1 | 12/1996 | | WO | WO 94/08604 | 4/1994 |
| EP | 0 706 376 B1 | 6/1997 | | WO | WO 94/08605 | 4/1994 |
| EP | 0 975 340 B1 | 2/2000 | | WO | WO 94/09010 | 4/1994 |
| EP | 1 360 967 A1 | 11/2003 | | WO | WO 94/09764 | 5/1994 |
| EP | 0 711 158 B1 | 12/2003 | | WO | WO 94/09812 | 5/1994 |
| EP | 0 621 015 A1 | 4/2004 | | WO | WO 94/13706 | 6/1994 |
| FR | 2255063 | 7/1975 | | WO | WO 94/15589 | 7/1994 |
| GB | 1 587 084 | 5/1981 | | WO | WO 94/15590 | 7/1994 |
| GB | 2 153 253 | 1/1985 | | WO | WO 94/15646 | 7/1994 |
| GB | 2 273 873 | 6/1994 | | WO | WO 94/16706 | 8/1994 |
| GB | 1 015 787 | 1/1996 | | WO | WO 94/17786 | 8/1994 |
| GB | 1 205 743 | 7/1996 | | WO | WO 94/18345 | 8/1994 |
| IT | 1247527 | 4/1991 | | WO | WO 94/18954 | 9/1994 |
| JP | 59-042375 | 3/1984 | | WO | WO 94/18967 | 9/1994 |
| JP | 03-297469 | 12/1991 | | WO | WO 94/18968 | 9/1994 |
| JP | 32-97469 | 12/1991 | | WO | WO 94/19000 | 9/1994 |
| JP | 60-25288 | 2/1994 | | WO | WO 94/19001 | 9/1994 |
| JP | 06-121828 | 6/1994 | | WO | WO 94/19003 | 9/1994 |
| JP | 06-205838 | 7/1994 | | WO | WO 94/20096 | 9/1994 |
| JP | 08-33718 | 2/1996 | | WO | WO 94/20097 | 9/1994 |
| JP | 09-255570 | 3/1996 | | WO | WO 94/20098 | 9/1994 |
| WO | WO 85/00107 | 1/1985 | | WO | WO 94/20099 | 9/1994 |
| WO | WO 88/10259 | 12/1988 | | WO | WO 94/20116 | 9/1994 |
| WO | WO 89/03232 A1 | 4/1989 | | WO | WO 94/20117 | 9/1994 |
| WO | WO 90/01969 | 3/1990 | | WO | WO 94/20126 | 9/1994 |
| WO | WO 90/07328 | 7/1990 | | WO | WO 94/20127 | 9/1994 |

| | | |
|---|---|---|
| WO | WO 94/21308 | 9/1994 |
| WO | WO 94/21309 | 9/1994 |
| WO | WO 94/21679 | 9/1994 |
| WO | WO 94/22436 | 10/1994 |
| WO | WO 94/23068 | 10/1994 |
| WO | WO 94/23699 | 10/1994 |
| WO | WO 94/24961 | 11/1994 |
| WO | WO 94/25020 | 11/1994 |
| WO | WO 94/25053 | 11/1994 |
| WO | WO 94/25588 | 11/1994 |
| WO | WO 94/26291 | 11/1994 |
| WO | WO 94/26303 | 11/1994 |
| WO | WO 94/26888 | 11/1994 |
| WO | WO 94/27612 | 12/1994 |
| WO | WO 94/28721 | 12/1994 |
| WO | WO 95/03036 | 2/1995 |
| WO | WO 95/03795 | 2/1995 |
| WO | WO 95/04544 | 2/1995 |
| WO | WO 95/05191 | 2/1995 |
| WO | WO 95/10611 | 4/1995 |
| WO | WO 94/10187 | 5/1995 |
| WO | WO 95/17095 | 6/1995 |
| WO | WO 95/19987 | 7/1995 |
| WO | WO 95/20582 | 8/1995 |
| WO | WO 95/30900 | 11/1995 |
| WO | WO 95/33736 | 12/1995 |
| WO | WO 96/01102 | 1/1996 |
| WO | WO 96/03092 | 2/1996 |
| WO | WO 96/07402 | 3/1996 |
| WO | WO 96/15224 | 5/1996 |
| WO | WO 96/20698 A2 | 7/1996 |
| WO | WO 96/21442 | 7/1996 |
| WO | WO 96/21443 | 7/1996 |
| WO | WO 96/24356 | 8/1996 |
| WO | WO 96/25176 | 8/1996 |
| WO | WO 96/32907 | 10/1996 |
| WO | WO 96/36349 | 11/1996 |
| WO | WO 96/40098 | 12/1996 |
| WO | WO 97/10011 | 3/1997 |
| WO | WO 97/10334 | 3/1997 |
| WO | WO 97/15319 | 5/1997 |
| WO | WO 97/21455 | 6/1997 |
| WO | WO 97/22697 | 6/1997 |
| WO | WO 97/33552 | 9/1997 |
| WO | WO 97/45105 | 12/1997 |
| WO | WO 00/00238 | 1/2000 |
| WO | WO 0047197 | 8/2000 |

OTHER PUBLICATIONS

"Churchill's Medical Dictionary", *definition of "cytostatic"*, 473, (1989).

"Cytochalasins", In: The Merck Index, Eleventh Edition, Merck & Co., Rahway NJ, 438-439 (1989).

"Glaxo Wellcome Preclinical Data: Preclinical studies conducted with GW 5638, a selective estrogen receptor modulator developed by Glaxo Wellcome, indicate that the compound acts both as an agonist and antagonist at estrogen receptor within specific . . . ", R & D Focus Drug News, (Sep. 8, 1997).

"Growth Factor Via Gene Therapy Abates Sore Rheumatoid Joints", BioWorld Today: The Daily Biotechnoloqy Newspaper, 9(115), Leff, David N., Editor, 1, (Jun. 17, 1998).

"Health Report—The Good News", Time, 23, (Apr. 1, 1996).

"Heparin", In: Modern Pharmacology, Craig, C.R., et al., (eds.), Little, Brown and Company, Boston, MA, p. 399, (1982).

"ICI United States, Inc., Tamoxifen citrate, Summary For Basis of Approval", (Dec. 30, 1977).

"Johnson & Johnson receives FDA approval to market Palmaz Balloon-expandable Stent for iliac arteries," Business Wire, Oct. 2, 1991.

"Micellar and Lyotropic Liquid Crystalline Phases Containing Nonionic Active Substances", In: Lyotropic Liquid Crystals and the Structure of Biomembranes, S. Fribert, (ed.), Advances in Chemistry Series, No. 152, American Chemical Society, 28-42, (1976).

"Muscle-Binding Gene Sees Two-Track Payoff: Human Therapies, Animal Meat", BioWorld Today: The Daily Biotechnology Newspaper, 8(85), Leff, David N., Editor, 1-3, (May 2, 1997).

"Nolvadex Tamoxifene Citrate", ICI Pharma, 64033-02, Rev L/07/92.

"Prevention of Coronary Heart Disease", In: Avery's Drug Treatment—Principles and Practice of Clinical Pharmacology and Therapeutics, Speight, T. M., (ed.), Williams and Wilkins, Baltimore, 594-595, (1987).

"Schering/Orion Fareston Anti-Estrogen for Treatment of Metastatic Breast Cancer 'Similar' to Tamoxifen, FDA Oncologic Committee Says in Approval Vote", F-D-C Reports, 15-16, (Oct. 23, 1995).

Shiga Medical Center for Adult Diseases, "The Impact of Tranilast on Restenosis Following Coronary Angioplasty: The Tranilast Restenosis Following Angioplasty Trial (TREAT)", Circulation, 90, 1-82, Abstract No. 0, (Oct. 1988).

"Tamoxifen therapy found safe for survivors of breast cancer", Fred Hutchinson Cancer Research Center Newsletter, 1(21), (Oct. 1995).

"Toprol XLTM Tablets", In: Physician's Desk Reference., 658-660, (Probably 1992).

Agarwal, A.K., et al., "Estrogen Receptor-Binding Affinity of Tamoxifen Analogs with Various Side Chains and their Biologic Profile in Immature Rat Uterus", Steroids, 56, 486-489, (1991).

AinMelk, Y., et al., "Tamoxifen Citrate Therapy in Male Fertility", Fertility and Sterility, 48, 113-117, (Jul. 1987).

Akselband, Y., et al., "Rapamycin Inhibits Spontaneous and Fibroblast Growth Factor Beta-Stimulated Proliferation of Endothelial Cells and Fibroblasts", Transplantation Proceedings, 23, 2833-2836, (1991).

Alberts, B. et al., "Molecular Biology of the Cell" $2^{nd}$ edition 1989, p. 653.

Alberts, B., et al., "Actin Filaments are Continually Formed and Broken Down in Cells", In: Molecular Biology of the Cell, Garland Publishing, London, 571, (1983).

Alderson, T. 1990.. "New targets for cancer chemotherapy—poly(ADP-ribosylation) processing and polyisoprenc metabolism," Biol. Rev. 65:623-641.

Aldridge, D.C., et al., "The Structures of Cytochalasins A and B", J. Chem. Soc., 17, 1667-1676, (1967).

Alich, A.A., et al., "Comparison of Aspirin and Copper Aspirinate with Respect to Gastric Mucosal Damage in the Rat", Journal of Pharmaceutical Sciences, 72, 1457-1461, (Dec. 1983).

Alich, A.A., et al., "Gastric Mucosal Damage Due to Aspirin and Copper Aspirinate Assessed by Gastric Mucosal Potential Difference Changes", Journal of Pharmacological and Toxicological Methods, 27, 245-250, (Jul. 1992).

Alich, A.A., et al., "Response to: 'The Ulcerogenic Potential of Copper Aspirinate Seems to be More Imaginary than Real'", Journal of Pharmaceutical Sciences, 73, Open Forum, 1876-1877, (Dec. 1984).

Allemann, et al., "Distribution, Kinetics, and Elimination of Radioactivity after Intravenous and Intramuscular Injection of 14C-Savoxepoine Loaded Poly (D,L-lactic acid) Nanospheres to Rats", J. Controlled Release, 29, 97-104, (1994).

Allemann, et al., "Drug Loaded Poly(Lactic Acid) Nanoparticles Produced by a Reversible Salting-out Process: Purification of an Injectable Dosage Form," Eur. J. Pharm. Biopharm., vol. 39 (1), pp. 13-18 (1993).

Allen, K.E., et al., "Evidence For The Metabolic Activation of Non-Steroidal Antioestrogens: A Study of Structure-Activity Relationships", Br.J. Pharmac., 71, 83-91, (1980).

Allen, R.E. & Boxhor, L.K. "Inhibition of skeletal muscle satellite cell differentiation by transforming growth factor-beta," J Cell. Physiol. 133:567-572.(1987).

Allgemeine und spezielle Pharmakologie und Toxikolgie, by W. Forth et al. 1984, pp. 524-531 and 627-633.

Alvarado, et al. "Evaluation of Polymer-Coated Balloon Expandable Stents in Bile Ducts," Radiology 165 (suppl.):33 1 (1987).

Anderson et al., "Restenosis after coronary angioplasty," J. Interv. Cardiol., 6(3)187-202 (1993).

Anderson, et al., "Effects of Acetate Dialysate on Transforming Growth Factor $\beta_1$ Interleukin, and $\beta_2$-Microglobulin Plasma Levels," Kidney International, vol. 40, pp. 1110-1117 (1991).

Ando et al., "Chimeric DNA-RNA hammerhead ribozyme targeting transforming growth factor-beta 1 mRNA inhibits neointima formation in rat carotid artery after balloon injury", Eur. J. Phamacol., 438:207-14 (2004).

Anker, et al., "Plasma Levels of the Atherogenic Amino Acid Homocysteine in Post-Menopausal Women with Breast Cancer Treated with Tamoxifen", Int. J. Cancer, 60, 365-368, (1995).

Arao, Y., et al., "A synthetic oestrogen antagonist, tamoxifen, inhibits oestrogen-induced transcriptional, but not post-transcriptional, regulation of gene expression", Biochem, J., 313, 269-274, (1996).

Aschermann, M., "Restenosis After Percutaneous Transluminal Coronary Angioplasty Pathophysiology, New Trends in Prevention and Treatment," Cor. Vasa., 36:211-218 (1994).

Assoian and Sporn, "Type beta Transforming Growth Factor in Human Platelets: Release During Platelet Degranulation and Action on Vascular Smooth Muscle Cells," The Journal of Cell Biology, vol. 102, pp. 1217-1223 (1986).

Assoian et al., "Transforming growth factor-beta in human platelets: identification of a major storage site, purification, .and characterization", J. Biol. Chem. 258:7155-7160 (1983).

Assoian, R.K., et al., "Cellular Transformation by Coordinated Action of Three Peptide Growth Factors from Human Platelets", Nature, 309, 804-806, (Jun. 28, 1984).

Attwood, et al., "A Light Scattering Study on Oil-in-Water Microemulsions" Int'l J. Pharm, 52 165-171 (1989).

Babaev, et al.,"Heterogeneity of smooth muscle cells in atheromatous plaques of human aorta," Am J. Pathol. 136:1031-1042. (1990).

Bagdade, et al., "Effects of Tamoxifen Treatment on Plasma Lipids and Lipoprotein Lipid Composition," J. of Clinical Endocrinology and Metabolism, vol. 70, No. 4, pp. 1132-1135 (1990).

Bailey et al., "Polymer Coating of Palmaz-Schatz Stent Attenuates Vascular Spasm after stent placement." Circulation 82:III-541 (1990).

Baim, D.S., et al., "Nonatherosclerotic Coronary Heart Disease", In: The Heart: Arteries and Veins, Sixth Edition, Logue, R.B., et al., (eds.), McGraw-Hill Book Company, New York, 1016-1025, (1986).

Bamburg, James R., "Biological and Biochemical Actions of Trichothecene Mycotoxins," Progress in Molecular and Subcellular Biology, (Hahn F.E., et al., ed.), Springer-Verlag, pp. 41-110) (1983).

Bang, H.O., et al., "The Composition of the Eskimo Food in North Western Greenland", Am. J. Clin. Nutr., 33, 2657-2661, (1980).

Baquial, J.G., et al., Down-Regulation of NADPH-Diaphorase (Nitric Oxide Synthase) May Account for the Pharmacological Activities of Cu(II)sub2(3,5-Diisopropylsalicylate)sub4., J. Inorganic Biochem., 60, 133-148, (1995).

Baral, E., et al., "Modulation of Lymphokine-Activated Killer Cell-Mediated Cytotoxicity By Estradiol and Tamoxifen", Int. J. Cancer, 66, 214-218, (1996).

Barath, et al., "Low Dose of Antitumor Agents Prevents Smooth Muscle Cell Proliferation After Endothelial Injury," JACC, vol. 13, No. 2, p. 252A Abstract (1989).

Barbacid, et al., "Binding of [acetyl-[14] C] Trichodermin to the Peptidyl Transferase Center of Eukaryotic Ribosomes," Eur. J. Biochem. 44, pp. 437-444 (1974).

Barbucci, et al., Coating of Commercially available materials with a new heparinizable material, 1991, pp. 1259-1274.

Barnard, et al., "Regulation of intestinal epithelial cell growth by transforming growth factor-beta." Proc. Natl Acad. Sci. USA 86:1518-1582.(1989).

Bartoli et al. "In vitro and in vivo Antitumoral Activity of Free, and Encapsulated taxol". J. Microencapsulation, 7 (2):191-197, 1990.

Basel, C. T., "The Antibiotic Complex of the Verrucarins and Roridins," Fortschr. Chem. Org. Naturst., 31:65 117 (1974).

Bassing et al., "FKBP12 is not required for the modulation of transforming growth factor beta receptor I signaling activity in embryonic fibroblasts and thymocytes", Cell Growth Differ., 9(3):223-8 (1998).

Battegay et al., "TGF-beta induces bimodal proliferation of connective tissue cells via complex control of an autocrine PDGF loop", Cell, 63:5t5-524 (1990).

Beck, et al., "Poly(DL-Lactide-co-glycolide) /Norethisterone Microcapsules: An Injectable Biodegradable Contraceptive," Biology of Reproduction, vol. 28, pp. 186-195 (1983).

Beck, L., et al., "Vascular Development: Cellular and Molecular Regulation", The FASEB Journal, 11, 365-373, (1997).

Benita et al., "Submicron Emulsions as Colloidal Drug Carries for Intravenous Administration: Comprehensive Physicochemical Characterization", Journal of Pharmaceutical Sciences, 82, (Nov. 1993).

Bergstrom, Reduction of fibrinogen adsorption on PEG-coated polystyrene surfaces, 1992, p. 779-790.

Bernhardt et al., "Acetylsalicylic acid, at high concentrations, inhibits vascular smooth muscle cell proliferation", J. Cardiovasc. Pharmacol., 21(6):973-6 (1993).

Bertelli, et al., "Adjuvant Tamoxifen in Primary Breast Cancer: Influence on Plasma Lipids and Antithrombin III Levels," Breast Cancer Res. and Treatment, vol. 12, pp. 307-310 (1988).

Berven, L.A., et al., "Cellular Function of p70S6K: A Role in Regulating Cell Motility", Immunology and Cell Biology, 78, 447-451, (2000).

Bier et al., "Arterial Remodeling: Importance in Primary Versus Restenoic Lesions", JACC, p. 139A, Abstract No. 875-96 (Feb. 1994).

Billmeyer, F., Textbook of Polymer Science (2d ed.) John Wiley & Sons, Inc. (1971).

Binmoeller, et al., "Silicone-Covered Expandable Metallic Stents in the Esophagus: An Experimental Study" Endoscopy 1992; 24:416-20.

Bittiner, S.B., et al., "A Double-Blind, Randomised, Placebo-Controlled Trial of Fish Oil in Psoriasis", The Lancet, 1, 378-380, (Feb. 20, 1988).

Bjorkerud, "Effects of transforming growth factor-beta1 on human arterial smooth muscle cells in vitro", Arterioscler. Thromb., 11(4):892-902 (1991).

Block, P.C. "Coronary-artery stents and other endoluminal devices," New Engl.J.Med. 1991; 324-52-3.

Bluming, "Hormone Replacement Therapy: Benefits and Risks for the General Postmenopausal Female Population and for Women with a History of Previously Treated Breast Cancer", Seminars in Oncology, 20, 662-674, (Dec. 1993).

Bogyo, et al., "Cytochalasin-β-Induced Immunosuppression of Murine Allogeneic Anti-tumor Response and the Effect of Recombinant Human Interleukin-2," Cancer Immunol. Immunother, vol. 32, pp. 400-405 (1991).

Bohmova et al., "Effect of sirolimus on ischemia/reperfusion injury in transgenic hypertensive rat", Transplant Proc., 34(8):3051-3052 (2002).

Border, W.A., et al., "Targeting TGF-Beta for Treatment of Disease", Nature Medicine, 1(10), 1000-1001, (Oct. 1995).

Boscoboinik et al., "Alpha-tocopherol (vitamin E) regulates vascular smooth muscle cell proliferation and protein kinase C activity", Arch. Biochem. Biophys., 286(1):264-9 (1991).

Bousquet, et al., "Effects of Cytochalasin β in Culture and in Vivo on Murine Madison 109 Lung Carcinoma and on B16 Melanoma," Cancer Res., vol. 50, pp. 1431-1439 (1990).

Boyle, "Macrophage activation in atherosclerosis: pathogenesis and pharmacology of plaque rupture", Curr. Vasc. Pharmacol., 3(1):63-8 (2005).

Brand, C., et al., "Transforming Growth Factor Beta1 Decreases Cholesterol Supply to Mitochondria via Repression of Steroidogenic Acute Regulatory Protein Expression", The Journal of Biochemistry, 273(11), 6410-6416, (1998).

Braun-Dullaeus et al., "Cell cycle protein expression in vascular smooth muscle cells in vitro and in vivo is regulated through phosphatidylinositol 3-kinase and mammalian target of rapamycin", Arterioscler Thromb Vasc Biol. 21(7):1152-58 (2001).

Brem et al., "Polymers as Controlled Drug Delivery Devices for the Treatment of Malignant Brain Tumours." European Journal of Pharmaceuticals and Biopharmaceutics, 1993, vol. 39, No. 1, pp. 2-7.

Brody, J.E., "Study Finds New Estrogen Offers Benefit Without Risk", The New York Times, A32, (Dec. 4, 1997).

Brott et al., "Vessel Remodeling After Angioplasty: Comparative Anatomic Studies", JACC, p. 138A, Abstract No. 875-43 (Feb. 1994).

Bruengger, et al., "Smooth Muscle Cell of the Canine Prostate in Spontaneous Benign Hyperplasia, Steroid Induced Hyperplasia and Estrogen or Tamoxifen Treated Dogs," J. Urol. vol. 130, No. 6, pp. 1208-1210 (1983).

Bruning, et al., "Tamoxifen, Serum Lipoproteins and Cardiovascular Risk", Br. J. Cancer, 58, 497-499 (1988).

Bumol, et al., "Unique Glycoprotein-Proteoglycan Complex Defined by Monoclonal Antibody on Human Melanoma Cells," PNAS (USA), vol. 79, pp. 1245-1249 (1982).

Burr, M.L., et al., "Effects of Changes in Fat, Fish and ibre Intakes on Death and Myocardial Reinfarction: Diat and Reinfarction Trial (DART)", The Lancet, 757-761, (Sep. 30, 1989).

Burton, T.M., "Lilly Osteoporosis Treatment Shows Promise", The Wall Street Journal, p. A3, A6, (Jun. 6, 1997).

Butta, et al., "Induction of Transforming Growth Factor $\beta_1$ in Human Breast Cancer in vivo Following Tamoxifen Treatment," Cancer Res. vol. 52, pp. 4261-4264 (1992).

C. Chamsangavej et al., A New Expandable Metallic Stent for Dilation of Stenotic Tubular Structures: Experimental and Clinical Evaluation, Houston Medical Journal 1987;2:41-51.

C. T. Dotter, "Transluminally Placed Coil Spring Endarterial Tube Grafts Long Term Patency in Canine Popliteal Arteries," Investigative Radiology 1969;4:329-332.

Calver et al. "Intracoronary Multi-link stents: experience in 218 patients using aspirin alone," Heart 1998;80:499-504.

Camenzind, et al., "Use of Locally Delivered Conventional Drug Therapies", Semin. Intervent. Cardiol., 1, 67-76 (1996).

Casscells, W., et al., "Elimination of Smooth Muscle Cells in Experimental Restenosis: Targeting of Fibroblast Growth Factor Receptors", Proc. Natl. Acad. Sci. USA, 89, 7159-7163 (1992).

Castellot et al., "Cultured endothelial cells produce a heparinlike inhibitor of smooth muscle cell growth", J. Cell Biol., 90:372-379 (1981).

Castellot et al., "Effect of heparin on vascular smooth muscle cells. I. Cell metabolism", J. Cell. Physiol., 124:21-28 (1985).

Castellot et al., Heparin selectively inhibits a protein kinase c-dependent mechanism of cell cycle progression in calf aortic smooth muscle cells, J Cell Biol.., 109:3147-3155 (1989).

Chaldakov, et al., "Cyclic AMP-and Cytochalasin B-induced Arborization in Cultured Aortic Smooth Muscle Cells: Its Cytopharmacological Characterization," Cell Tissue Res. vol. 255, pp. 435-442 (1989).

Chamberlain, Transforming growth factor-beta: a promising target for anti-stenosis therapy, Cardiovasc. Drug Rev.., 19(4):329-344 (2001).

Chamley-Campbell and Campbell, "What controls smooth muscle phenotype?", Atherosclerosis, 40:347-357 (1981).

Chamsangavej et al., "Endovascular Stent for Vena Caval Stenosis: Laboratory Experiment and Potential Clinical Applications," Radiology Nov. 1985;157(P):66 Abs. 129.

Chander, et al., "Pyrrolidino-4-iodotamoxifen and 4-lodotamoxifen, New Analogues of the Antiestrogen Tamoxifen for the Treatment of Breast Cancer," Cancer Research, vol. 51, pp. 5851-5858 (1991).

Chandrasekar, B., et al., "Dietary Omega-3 Lipids Delay the Onset and Progression of Autoimmune Lupus Nephritis by Inhibiting Transforming Growth Factor Beta mRNA and Protein Expression", Journal of Autoimmunity, 8, 381-393, (1995).

Chandy, T., et al., "Chitosan Matrix for Oral Sustained Delivery of Ampicillin", Biomaterials, 14, 939-944, (1993).

Chang, M.P., et al., "Comparison of the Intoxication Pathways of Tumor Necrosis Factor and Diphtheria Toxin", Infection and Immunity, 58, 2644-2650, (Aug. 1990).

Chao, et al., "Altered Cytokine Release in Peripheral Blood Mononuclear Cell Cultures from Patients with the Chronic Fatigue Syndrome," Cytokine, vol. 3, No. 4, pp. 292-298 (1991).

Chapman, et al., "A Bioabsorbable Stent: Initial Experimental Results," Supplement III Cir., vol. 82, No. 4, p. III-72 (1990).

Charles Dotter et al., "Transluminal Treatment of Arteriosclerotic Obstruction Description of a New Technique and a Preliminary Report of its Application," Circulation 1964;30:654-669.

Charlier, C., et al., "Tamoxifen and Its Active Metabolite Inhibit Growth of Estrogen Receptor-Negative MDA-MB-435 cells", Biochemical Pharmacology, 49(3), 351-358, (Jan. 1995).

Charlier, et al., "Tamoxifen in the Treatment of Breast Cancer", J. Gynecol. Obstet Biol. Reprod., 23, 751-756, (1994).

Charnsangavej, et al., "Stenosis of the Vena Cava: Preliminary Assessment of Treatment with Expandable Metallic Stents," Radiology Nov. 1986;161:295.

Chauhan et al., "Activation of Transforming Growth Factor-B is Inversely Correlated with Three Major Risk Factors for Coronary Artery Disease: Lipoprotein(a), LDL-Cholesterol and Plasminogen Activator Inhibitor-1", Circulation, 90 I-623, Abstract No. 3354 (Oct. 1994).

Cheitlin, M.D., et al., "Myocardial Infarction without Atherosclerosis", JAMA, 231, 951-959, (1975).

Chen et al., "Transforming growth factor type beta specifically stimulates synthesis of proteoglycan in human adult arterial smooth muscle cells", Proc. Natl. Acad. Sci., 84:5287-5291 (1987).

Clark, D.A., et al., "Coronary Artery Spasm: Medical Management, Surgical Denegration, and Autotransplantation", The Journal of Thoracic and Cardiovascular Surgery, 73, 332-339, (1977).

Clarke, S.C., et al., "Tolerance and Responses To Tamoxifen and Toremifene in Male Patients with Coronary Artery Disease.", Abstract for ACC Meeting, Mar. 1999.

Clowes and Karnowsky, "Suppression by heparin of smooth muscle cell proliferation in injured arteries", Nature, 265:625-626 (1977).

Clowes et al., "Heparin and cilazapril together inhibit injury-induced intimal hyperplasia", Hypertension, 18:II-65-II-69 (1991).

Clowes et al., "Significance of Quiescent Smooth Muscle Migration in the Injured Rat Carotid Artery," Cir. Res. vol. 56, No. 1, pp. 139-145 (1985).

Clowes, et al. "Mechanisms of Stenosis After Arterial Injury", Laboratory Investigation, vol. 49, No. 2, pp. 208-215 (1983).

Clowes, et al., "Kinetics of Cellular Proliferation After Arterial Injury—I. Smooth Muscle Growth in the Absence of Endothelium", Laboratory Investigation, vol. 49, No. 3, pp. 327-333 (1983).

Clowes, et al., "Kinetics of Cellular Proliferation After Arterial Injury—III, Endothelial and Smooth Muscle Growth in Chronically Denuded Vessels", Laboratory Investigation, vol. 54, No. 3, pp. 295-303 (1986).

Cohen, et al., "Controlled Delivery Systems for Proteins Based on Poly(Lactic/Glycolic Acid) Microspheres," Pharmaceutical Research, vol. 8, No. 6, pp. 713-720 (1991).

Cole, R. J. et al., "The Cytochalasins", In: Handbook of Toxic Fungal Metabolics, Academic Press, New York, p. 264-265, 281-282 (1981).

Colletta, A.A. et al., "Anti-oestrogens induce the secretion of active transforming growth factor beta from human fetal fibroblasts", Br. J. Cancer, 62, 405-409, (1990).

Columbo et al., "A Novel Strategy for Stent Deployment in the Treatment of Acute or Threatened Closure Complicating Balloon Coronary Angioplasty," JACC Dec. 1993;22(7):1887-91.

Comezoglu, F.T. et al., "Serum Stability and Cytotoxicity of the Macrocyclic Trichothecenes Roridin A, Verrucarin A and Their Monoclonal Antibody Conjugates", Proceedings of the American Association for Cancer Research, 31, Abstract No. 1723, p. 291, (Mar. 1990).

Coomber and Gotlieb "In vitro endothelial wound repair. Interaction of cell migration and proliferation". Aterioslcerosis, 10 (2):215-222, 1990.

Coombes, R.C., et al., "Idoxifene: Report of a Phase I Study in Patients with Metastatic Breast Cancer", Cancer Research, 55, 1070-1074, (Mar. 1, 1995).

Corcos, et al., "Failure of diltiazem to prevent restenosis after percutaneous transluminal coronary angioplasty", Am. Heart J., 109(5):926-931 (1985).

Cotton, P., "Restenosis Trials Suggest Role for Remodeling", JAMA, 271, 1302-1305, (May 4, 1994).

Cowsar, et al., "Poly(Lactide-co-glycolide) Microcapsules for Controlled Release of Steroids," Methods in Enzymology, vol. 112, pp. 101-117 (1985).

Cox et al., "Effects of local delivery of heparin and methotrexate on neointimal proliferation in stented porcine coronary arteries". Coronary Artery Disease, 3:237-248, 1992.

Cox et al., "Local Delivery of Heperin and methotrexate fails to inhibit in vivo smooth muscle cell proliferation". Circulation Suppl. 84(4):11-71, #0284, 1991.

Craig et al., "Anticoagulant Drugs" in Modern Pharmacology; Little, Brown & Co.: Boston; p. 399 (1982(.

Crissman, et al., "Transformed Mammalian Cells are Deficient in Kinase-Mediated Control of Progression Through the $G_1$ Phase of the Cell Cycle," PNAS (USA), vol. 88, pp. 7580-7584 (1991).

Csernok, E., et al., "Transforming Growth Factor-beta (TGF-beta) Expression and Interaction with Proteinase 3 (PR3) in Anti-Neutrophil Cytoplasmic Antibody (ANCA)-associated Vasculitis", Clin. Exp. Immunol., 105, 104-111, (1996).

Cunningham, A., et al., "A Study of the Structural Basis of the Carcinogenicity of Tamoxifen, Toremifene and their Metabolites", Mutation Research, 349, 85-94, (1996).

Currier et al., "Low molecular weight heparin (enoxaparin) reduces restenosis after iliac angioplasty in the hypercholesterolemic rabbit", J. Am. Coll. Cardiol., 17(6):118B-125B (1991).

Currier, "Restenosis After Percutaneous Transluminal Coronary Angioplasty: Have We Been Aiming at the Wrong Target?", JACC, 25 516-520 (Feb. 1995).

Dangas, G., et al., "Management of Restenosis after Coronary Intervention", American Heart Journal, 132, 428-436, (1996).

Danielpour, David, "Improved Sandwich Enzyme-Linked Immunosorbent Assays for Transforming Growth Factor," Journal of Immunological Methods, vol. 158, pp. 17-25 (1993).

Danielpour, et al., "Immunodetection and Quantitation of the Two Forms of Transforming Growth Factor-Beta (TGF-1 and TGF-2) Secreted by Cells in Culture," Journal of Cellular Physiology, vol. 138, pp. 79-86 (1989).

Davies, A.M., et al., "Peroxidase Activation of Tamoxifen and Toremifene Resulting in DNA Damage and Covalently Bound Protein Adducts", Carcinogenesis, 16, 539-545, (1995).

deAlvare, L.R., et al., "Mechanism of Superoxlde Anion Scavenging Reaction by Bis-(Salicylato)-Copper(II) Complex", Biochemical and Biophysical Research Communications, 69, 687-694, (1976).

Dehmer, G.J., et al., "Reduction in the Rate of Early Restenosis After Coronary Angioplasty by a Diet Supplemented with n-3 Fatty Acids", N. Engl. J. Med., 319, 733-740, (1988).

Del Vecchio et al., "Inhibition of human scleral fibroblast proliferation with heparin, Invest".. Ophthalmol. Vis. Sci., 29:1272-1276 (1988).

Delmas, P.D., "Effects of Raloxifene on Bone Mineral Density, Serum Cholesterol Concentrations, and Uterine Endometrium in Postmenopausal Women", The New England Journal of Medicine, 337(23), (1997).

Detre, et al., "Percutaneous Transluminal Coronary Angioplasty in 1985-1986 and 1977-1981", The New England J. of Med., vol. 318, No. 5, pp. 265-270 (1988).

DiGiacomo, R.A., et al., "Fish-Oil Dietary Supplementation in Patients with Raynaud's Phenomenon: A Double-Blind, Controlled, Prospective Study", Am. J. Med., 86, 158-164, (Feb. 1989).

DiLuccio, R.C., et al., "Sustained-Release Oral Delivery of Theophylline by Use of Polyvinyl Alcohol and Polyvinyl Alcohol-Methyl Acrylate Polymers", Journal of Pharmaceutical Sciences, 83, 104-106, (Jan. 1994).

Dimond, Patricia F., Ph.D., "TGF-Beta Shows Potential as Therapeutic Agent for Macular Holes," Genetic Engineering News, pp. 7 & 19 (1993).

Donnelly, J., et al., "Protective Efficacy of Intramuscular Immunization with Naked DNA; DNA Vaccines: A New Era in Vaccinology, Margaret A. Liu et al., eds.", Annals of the New York Academy of Sciences, 772, 40-44, (1995).

Dotter, "Intraventional Radiology—Review of an Emerging Field," Seminars in Roentgenology 1982;16(1):7-8.

Dove, C.R., et al., "Effect of Vitamin E and Copper on the Vitamin E Status and Performance of Growing Pigs", J. Anim. Sc., 69, 2516-2523, (1991).

Dowsett, M., "New Developments in the Hormonal Treatment of Breast Cancer", In: The Treatment of Cancer: Beyond Chemotherapy, Conference Documentation, The Glouster Hotel, London, 7 p., (Mar. 13-14, 1995).

Dragan, Y.P., et al., "Comparison of the Effects of Tamoxifen and Toremifene on Liver and Kidney Tumor Promotion in Female Rats", Carcinogenesis, 16, 2733-2741, (1995).

Draper, M.W., et al., "Antiestrogenic Properties of Raloxifene", Pharmacology, 50, 209-217, (Apr. 1995).

Dyerberg, J., "Platelet—Vessel Wall Interaction: Influence of Diet", Phil. Trans. R. Soc. Lond., B 294, 372-381, (1981).

Dyerberg, J., et al., "The Effect of Arachidonic- and Eicosapentaenoic Acid on the Synthesis of Prostacyclin-like Material in Human Umbilical Vasculature", Artery, 8, 12-17, (1980).

Ebner, et al., "Cloning of a Type 1 TGF-$\beta$ Receptor and Its Effect on TGF-$\beta$ Binding to the Type II Receptor," Science, vol. 260, pp. 1344-1348 (1993).

Edelman, E.R., et al., "Effect of Controlled Adventitial Heparin Delivery on Smooth Muscle Cell Proliferation Following Endothelial Injury", Proc. Natl. Acad. Sci. USA, 87, 3773-3777, (May 1990).

Eldridge, et al., "Biodegradable and Biocompatible Poly(DL-Lactide-CO-Glycolide) Microspheres as an Adjuvant for Staphylococcal Enterotoxin B Toxoid which Enhances the Level of Toxin-Neutralizing Antibodies," Infection and Immunity, 59(9):2978-2986 (1991).

Ellis et al., "Effect of 18- to 24-hour heparin administration for prevention of restenosis after uncomplicated coronary angioplasty", Am, Heart J., 117(4):777-782 (1989).

Ellis, S.G., et al., "In-Hospital Cost of Percutaneous Coronary Revascularization: Critical Determinants and Implications", Circulation, 92, 741-747, (1995).

Endres, S., et al., "The Effect of Dietary Supplementation with n-3 polyunsaturated Fatty Acids on the Synthesis of Interleukin-1 and Tumor Necrosis Factor by Mononuclear Cells", N. Engl. J. Med., 320, 265-271, 1989).

Epstein, Stephen E., MD., "Cytotoxic Effects of a Recombinant Chimeric Toxin on Rapidly Proliferating Vascular Smooth Muscle Cells," Cir. vol. 84, No. 2, pp. 778-787 (1991).

Esnouf, M.P., et al., "The Inhibition of the Vitamin K-Dependent Carboxylation of Glutamyl Residues in Prothombin by Some Copper Complexes", FEBS Letters, 107, 146-150, (1979).

Espinosa, E., et al., "17-Estradiol and Smooth Muscle Cell Proliferation in Aortic Cells of Male and Female Rats", Biochemical and Biophysical Research Communication, 221, 8-14, (1996).

Ettenson and Gotlieb "Centrosomes, Microtubules, and Microfilaments in the Reendothelialization and Remodeling of Double-Sided In Vitro Wounds". Laboratory Investigation, vol. 68, No. 6, pp. 722-733, 1992, United States and Canadian Academy of Pathology, Inc.

Evans, G.L., et al., "Tissue-Selective Actions of Estrogen Analogs", Bone, 17, 181S-190S, (Oct. 1995).

Fanelli, et al., "Restenosis Following Coronary Angioplasty", Amer. Heart J., vol. 119, No. 2, Part 1, pp. 357-368 (1990).

Farhat, et al., "In Vitro Effect of Oestradiol on Thymidine Uptake in Pulmonary Vascular Smooth Muscle Cell: Role of the Endothelium," Br. J. Pharmacol. vol. 107, pp. 679-683 (1992).

Faxon et al., "Enozaprain, a low molecular weight heparin, in the prevention of restenosis after angioplasty: results of a double blind randomized trial", JACC 19:258A, Abstract 783-3 (1992).

Faxon et al., "Restenosis Following Transluminal Angioplasty in Experimental Atherosclerosis", Arteriosclerosis, vol. 4, No. 3, pp. 189-195 (1984).

Fay, et al., "Effects of Cytochalasin B On The Uptake of Ascorbic Acid and Glucose By 3T3 Fibroblasts: Mechanism of Impaired Ascorbate Transport in Diabetes," Life Sci., vol. 46, pp. 619-624 (1990) (USA).

Feelisch, et al., "Biotransformation of Organic Nitrates to Nitric Oxide by Vascular Smooth Muscle and Endothelial Cells," Biochemical and Biophysical Research Communications, vol. 180, No. 1, pp. 286-293 (1991).

Ferrari, R.P., et al., "Changes of Serum Iron Transferrin and Copper Ceruloplasmin in Rats Given Cu(II) sub2 (Acetylsalicyate) sub4 During Acute Inflammation", Anticancer Res., 9, 771-774, (1989).

Fett-Neto, A.G., et al., "Effect of White Light on Taxol and Baccatin III Accumulation in Cell Cultures of Taxus Cuspidata Sieb and Zucc.", J. Plant Physiol., 146, 584-590, (1995).

Fischell, et al., "Low-Dose, beta-Particle Emission From 'Stent' Wire Results in Complete, Localize Inhibition of Smooth Muscle Cell Proliferation", Circulation, 90 2956-2963 (Dec. 1994).

Fischer, et al., "A Possible Mechanism in Arterial Wall for Mediation of Sex Difference in Atherosclerosis Experimental and Molecular Pathology", Exp. Mol. Pathol., 43 288-296 (1985).

Fischman, et al., A Randomized Comparison of Coronary-Stent Placement and Balloon Angioplasty in the Treatment of Coronary Artery Disease:, The New England Journal of Medicine, 331, 496-501 (Aug. 1994).

Fisher, M., et al., "Dietary n-3 Fatty Acid Supplementation Reduces Superoxide Production and Chemiluminescence in a Monocyte-Enriched Preparation of Leukocytes", Am. J. Clin. Nutr., 51, 804-808, (1990).

Flanders, K.C., et al., "Altered Expression of Transforming Growth Factor-B in Alzheimer's Disease", Neurology, 45, 1561-1569, (Aug. 1995).

Flanders, K.C., et al., "Transforming Growth Factor-B1: Histochemical Localization With Antibodies to Different Epitopes", Journal of Cell Biology, 108, 653-660, (Feb. 1989).

Foekens, J.A., et al., "Urokinase-Type Plasminogen Activator and Its Inhibitor PAI-1: Predictors of Poor Response to Tamoxifen Therapy in Recurrent Breast Cancer", Journal of the National Cancer Institute, 87(10), 751-756, (May 1995).

Forney-Prescott et al., "Angiotensin-converting enzyme inhibito' versus angiotensin II, AT1 receptor antagonist: effects on smooth muscle cell migration and proliferation after balloon catheter injury", Am J Pathol, 139:1291-1296 (1991).

Forrester, J.S., et al., A Paradigm for Restenosis Based on Cell Biology: Clues for the Development of New Preventive Therapies: JACC, 17, 758-769, (1991).

Fox and DiCorleto, "Fish oils inhibit endothelial cell production of platelet-derived growth factor-like protein", Science, 241 (4864):453-456 (1988).

Frautschy, S.A., et al., "Rodent Models of Alzheimer's Disease: Rat A Infusion Approaches to Amyloid Deposits", Neurobiology of Aging, 17, 311-321, (1996).

Frazier-Jessen, et al., "Estrogen Modulation of JE/Monocytte Chemoattractant Protein-1 mRNA Expression in Murine Macrophages", J. Immunol., 1828-1845.

Friberg, et al., "Microemulsions and Solubilization by Nonionic Surfactants", Prog. Colloid and Polymer Sci., 56, 16-20 (1975).

Frye, L.L., et al., "Oxolanosterol Oximes: Dual-Action Inhibitors of Cholesterol Biosynthesis", Journal of Lipid Research, 35, 11333-1344, (1994).

Fukaura, H., et al., "Induction of Circulating Myelin Basic Protein and Proteolipid Protein-Specific Transforming Growth Factor-B1-secreting Th3 T Cells by Oral Administration of Myelin in Multiple Sclerosis Patients", J. Clin. Invest., 98, 70-77, (1996).

Fukuda, et al., "Distinct Expression of Transforming Growth Factor-B Receptor Subtypes on Vascular Smooth Muscle Cells from Spontaneously Hypertensive Rats and Wistar-Kyoto Rats", Clin. Exp. Pharmacol. Physiol. Supply., 1, S120, 1995.

Fulop, et al., "Age-Dependent Variations of Intralysosomal Enzyme Release from Human PMN Leukocytes Under Various Stimuli," Immunobiol., vol. 171, pp. 302-310 (1986).

Furr, B.J., et al., "The Pharmacology and Clinical Uses of Tamoxifen", Pharmac. Ther., 25, 127-205, (1984).

Garg, U.C., et al., "Nitric Oxide-Generating Vasodilators and 8-Bromo-Cyclic Guanosine Monophosphate Inhibit Mitogenesis and Proliferation of Cultured Rat Vascular Smooth Muscle Cells", Journal of Clinical Investigation, 83, 1774-1777, (May 1989).

Garrigues, et al., "The Melanoma Proteoglycan: Restricted Expression on Microspikes, a Specific Microdomain of the Cell Surface," J. Cell Biol. vol. 103, pp. 1699-1710 (1986).

Gasco, et al., "In Vitro Permeation of Azelaic Acid from Viscosized Microemulsions", International Journal of Pharmaceutics, 69, 193-196 (1991).

Gasco, M. R., et al., Long-acting Delivery Systems for Peptides: Reduced Plasma Testosterone Levels in Male Rats after a Single Injection:, Intl. J. of Pharmaceut, 62 119-123 (1990).

Gebhardt, R., et al., "Differential Inhibitory Effects of Garlic-Derived Organosulfur Compounds on Cholesterol Biosynthesis in Primary Rat Hepatocyte Cultures", Lipids, 31, 1269-1276, (1996).

Gebhardt, R., et al., "Inhibition of Cholesterol Biosynthesis by Allicin and Ajoene in Rat Hepatocytes and HepG2 Cells", Biochimica et Biophysica Acta, 1213, 57-62, (1994).

Gertz et al., "Geometric Remodeling Is Not the Principal Pathogenic Process in Restoenosis After Balloon Angioplasty", Circulation, 90, 3001-3008 (Dec. 1994).

Giachelli, et al., "Osteopontin is Elevated During Neointima Formation in Rat Arteries and is a Novel Component of Human Atherosclerosis Plaques", J. Clin. Invest., 92, 1686-1696, (Oct. 1993).

Gibbons et al., "The emerging concept of vascular remodeling", New Engl. J. of Medicine, 330 1431-1437 (1994).

Gibson, D.M., et al., "Initiation and Growth of Cell Lines of Taxus Brevifolia (Pacific Yew)", Plant Cell Reports, 12, 479-482, (1993).

Glagov, et al., "Compensatory Enlargement of Human Atherosclerotic Coronary Arteries," New England J. of Med., vol. 316 No. 22, p. 1371-1375 (1987).

Glagov, S., "Intimal Hyperplasia, Vascular Modeling, and the Restenosis Problem", Circulation, 89, 2888-2891, (1994).

Goldman, et al., "Influence of Pressure on Permeability of Normal and Diseased Muscular Arteries to Horseradish Peroxidase," Atherosclerosis, vol. 65, pp. 215-225 (1987).

Goodnight, S.H., "The Effects of n-3 Fatty Acids on Atherosclerosis and the Vascular Response to Injury", Arch. Pathol. Lab. Med., 117, 102-106, (Jan. 1993).

Gradishar, W.J., et al., "Clinical Potential of New Antiestrogens", Journal of Clinical Oncology, 15, 840-852, (1997).

Graham et al., "Dexamethasone Inhibits Grown and Na:H Exchange in Vascular Smooth Muscle Cells" Journal of Endocrinology, 129 (Suppl.) Abstract 180, 10$^{th}$ Joint Metting of British Endocdrine Societies, Brighton, England, UK, Apr. 15-18, 1991.

Grainger and Metcalfe, TGF-beta: implications for human vascular disease. J Hum Hypertens., 9(8):679 (1995).

Grainger and Mosedale, "TGF-$\beta$ and the cardiovascular system, TGF-$\beta$ and Related Cytokines in Inflammation," Breit, SN and Wahl, SM (ed.), Birkhauser Verlag, 91-146 (2001) (DJG 006134-006190).

Grainger et al., "Dietary fat and reduced levels of TGFbeta 1 act synergistically to promote activation of the vascular endothelium and formation of lipid lesions", J. Cell Sci., 113:2355-2361(2000).

Grainger et al., "Transforming growth factor-beta dynamically regulates vascular smooth muscele cell differentiation in vivo", J. Cell Sci., 111:2977-2988 (1998).

Grainger, D.J., "Transforming growth factor beta and atherosclerosis: so far, so good for the protective cytokine hypothesis", Arterioscler. Thromb. Vasc. Biol., 24:399-404 (2004) (DJG 006208-006213).

Grainger, D.J., et al., "A Pivotal Role for TGF-Beta in Atherogenesis?", Biol. Rev., 70, 571-596, (1995).

Grainger, D.J., et al., "Activation of Transforming Growth Factor-beta is Inhibited by Apolipoprotein (a) in vivo", Circulation, 90, 67$^{th}$ Scientific Session, Abstract No. 3353, p. I-623, (Oct. 1994).

Grainger, D.J., et al., "Activation of Transforming Growth Factor-beta is Inhibited in Transgenic Apolipoprotein (a) Mice", Nature, 370 460-462, (Aug. 11, 1994).

Grainger, D.J., et al., "Active and Acid-Activatable TGF-beta in Human Sera, Platelets and Plasma", Clinica Chemica Acta., 235, 11-31, (Feb. 1995).

Grainger, D.J., et al., "Active TGF-beta is Depressed Five-fold in Triple Vessel Disease Patients Compared with Syndrome X Patients", Journal of Cellular Biochemistry, 18A, Abstract No. E111, p. 267, (1994).

Grainger, D.J., et al., "Active Transforming Growth Factor-beta is Depressed in Patients with Three Vessel Coronary Artery Disease", Circulation, 90, 67$^{th}$ Scientific Sessions, Abstract No. 2754, p. I-512, (Oct. 1994).

Grainger, D.J., et al., "Hexamethylenebisacetamide Selectively Inhibits the Proliferation of Human and Rat Vascular Smooth-Muscle Cells", Biochemical Journal, 283, 403-408, (1992).

Grainger, D.J., et al., "Mitogens for Adult Rat Aortic Vascular Smooth Muscle Cells in Serum-Free Primary Culture", Cardiovascular Research, 28, 1238-1242, (1994).

Grainger, D.J., et al., "Proliferation of Human Smooth Muscle Cells Promoted by Lipoprotein(a)", Science, 260, 1655-1658, (Jun. 11, 1993).

Grainger, D.J., et al., "Release and Activation of Platelet Latent TFG-Beta in Blood Clots During Dissolution with Plasmin", Nature Medicine, 1, 932-937, (1995).

Grainger, D.J., et al., "Tamoxifen Elevates Transforming Growth Factor-beta and Suppresses Diet-Induced Formation of Lipid Lesions in Mouse Aorta", Nature Medicine, 1, 1067-1073, (Oct. 1995).

Grainger, D.J., et al., "Tamoxifen: Teaching an Old Drug New Tricks?", Nature Medicine, 2, 381-385, (Apr. 1996).

Grainger, D.J., et al., "The Serum Concentration of Active Transforming Growth Factor-beta is Severely Depressed in Advanced Atherosclerosis", Nature Medicine, 1, 74-80, (Jan. 1995).

Grainger, D.J., et al., "Transforming Growth Factor beta Decreases the Rate of Proliferation of Rat Vascular Smooth Muscle Cells by Extending the G2 Phase of the Cell Cycle and Delays the Rise in Cyclic AMP Before Entry into M Phase", Biochemical Journal, 299, 227-235, (1994).

Grainger, D.J., et al., "Transforming Growth Factor-beta and Cardiovascular Protection", In: TheEendothelium in Clinical Practice, Rubanyi, G.M., et al., (eds.), Marcel Dekker, Inc., New York, 203-243, (1997).

Grainger, D.J., et al., "Transforming Growth Factor-beta is Sequestered into an Inactive Pool by Lipoproteins", Journal of Lipid Research, 38, 117-125, (1997).

Grainger, D.J., et al., "Transforming Growth Factor-beta: The Key to Understanding Lipoprotein(a)?", Current Opinion In Lipidology, 6, 81-85, (1995).

Grainger, D.J., University of Cambridge Ph.D. Thesis, Control of the proliferation and differentiation of vascular smooth muscle cells, DJG 005911-006102 (1992) and all references therein.

Grainger, et al., "Heparin decreases the rate of proliferation of rat vascular smooth muscle cells by releasing transforming growth factor-like activity from serum," Cardiovascular Research, vol. 27, pp. 2238-2247 (1993).

Grainger, et al., "Tamoxifen Decreases the Rate of Proliferation of Rat Vascular Smooth Muscle Cells in Culture by Inducing Production of Transforming Growth Factor β," Biochem J. vol. 294, pp. 109-112 (1993).

Grainger, et al., A Large Accumulation of Non-Muscle Myosin Occurs at First Entry into M Phase in Rat Vascular Smooth-Muscle Cells, Biochem. J. vol. 277, pp. 145-151 (1991).

Gravlee, G.P. MD, Heparin-Coated Cardiopulmonary Bypass Circuits, Journal of Cardiothoracic and Vascular Anesthesia, vol. 8, No. 2, Apr. 1994, pp. 213-222.

Gref, et al., "Biodegradable Long-Circulating Polymeric Nanoshoeres", Science, 263, 1600-1603, (Mar. 18, 1994).

Gregory et al., Rapamycin Inhibits Arterial Intimal Thickening Caused by Both Alloimmune and Mechanical Injury:, Transplantation, 55 1409-1418 (1993).

Gregory et al., "Treatment with rapamycin blocks arterial intimal thickening following mechanical and alloimmune injury", Transplant. Proc., 25:120-21 (1993).

Gregory, et al. "Effects of Treatment with Cyclosporine, FK 506, Rapamycin, Mycophenolic Acid, or Deoxyspergualin on Vascular Muscle Proliferation in Vivo," Transplantation Proceedings, 25:770-771 (1993).

Grese, T.A., et al., "Structure-Activity Relationships of Selective Estrogen Receptor Modulators: Modification to the 2-Arylbenzothiophene Core of Raloxifene", J. Med. Chem., 40, 146-167, (1997).

Grey, A.B., et al., "The Effect of the Anti-Estrogen Tamoxifen on Cardiovascular Risk Factors in Normal Postmenopausal Women", J. Clinical Endocrinology and Metabolism, 80, 3191-3195, (1995).

Grigg, L.E., et al., "Determinants of Restenosis and Lack of Effect of Dietary Supplementation with Eicosapentaenoic Acid on the Incidence of Coronary Artery Restenosis After Angioplasty", JACC, 13, 655-672, (1989).

Gruntzig, et al., "Nonoperative Dilatation of Coronary-Artery Stenosis," New England J. Med.. Jul. 12, 1979;301(2):61-68.

Guba et al., "Rapamycin inhibits primary and metastatic tumor growth by antiangiogenesis: involvement of vascular endothelial growth factor", Nat. Med., 8(2):128-35 (2002).

Guetta, V., et al., "Effects of the Antiestrogen Tamoxifen on Low-Density Lipoprotein Concentrations and Oxidation in Postmenopausal Women", The American Journal of Cardiology, 76, 1072-1073, (Nov. 15, 1995).

Gulino, A., et al., Heterogeneity of Binding Sites for Tamoxifen and Tamoxifen Derivatives in Estrogen Target and Nontarget Fetal Organs of Guinea Pig, Cancer Research 42, 1913-1921, (May 1982).

Guyton et al., "Inhibition of rat arterial smooth muscle cell proliferation by heparin: in vivo studies with anticoagulant and noncoagulant heparin", Circ. Res., 46(5):625-634 (1980).

Gylling, H., et al., "Tamoxifen and Toremifene Lower Serum Cholesterol by Inhibition of Delta8-Cholesterol Conversion to Lathosterol in Women with Breast Cancer", Journal of Clinical Oncology, 13, 2900-2905, (1995).

Gylling, H., et al., "Tamoxifen Decreases Serum Cholesterol by Inhibiting Cholesterol Synthesis", Atherosclerosis, 96, 245-247, (1992).

Hafzi et al., "Differential effects of rapamycin, cyclosporine A, and FK506 on human coronary artery smooth muscle cell proliferation and signalling", Vascul. Pharmacol., 41:167-76 (2004).

Hahn, L., et al., "The Influence of Acetylsalicylic Acid and Paracetamol on Menstrual Blood Loss in Woman With and Without an Intrauterine Contraceptive Device", Am. J. Obstet. Gnecol., 135, 393-396, (1979).

Hall, I.H., et al., "Hypolipidemic Activity of Tetrakis-mu-(trimethylamine-boranecarboxylato)-bis (trimethylamine-carboxyborane) -dicopper (II) in Rodents and Its Effect on Lipid Metabolism", J. Pharmaceut. Sci., 73, 973-977, (1984).

Hanke, et al., Inhibition of Cellular Proliferation After Experimental Balloon Angioplasty by Low-Molecular-Weight Heparin, Circulation, vol. 85, No. 4, pp. 1548-1556 (1992).

Hanson, et al., "In vivo evaluation of artificial surfaces with a non-human primate model of arterial thrombosis," J. Lab. Clin. Med. 95:289-304; 1980.

Hanson, et al., "Testing of Blood—Materials Interactions," Biomaterials Science (B.D. Ratner, Ed.), Academic Press, 222-238 (1996).

Harpel, et al., "Plasmin Catalyzes Binding of Lipoprotein ($\alpha$) to Immobilized Fibrinogen and Fibrin," Proc. Natl. Acad. Sci. USA, vol. 86, pp. 3847-3851 (1989).

Harrison, D.C., "Nonatherosclerotic Coronary Artery Disease", In.: Atherosclerosis and Coronary Artery Disease, V. Fuster, et al., (eds.), Lippencott-Raven Publishers, pp. 757-772, (1996).

Hayden, L.J., "Inhibitors of Gastric Lesion in the Rat", J. Pharm. Pharmac., 30, 244-246, (1978).

Hayes, D.F., et al., "Randomized Comparison of Tamoxifen and Two Separate Doses of Toremifene in Postmenopausal Patients with Metastatic Breast Cancer", Journal of Clinical Oncology, 13, 2556-2566, (Oct. 1995).

Hehrlein, C., et al., "Low-Dose Radiactive Endovascular Stents Prevent Smooth Muscle Cell Proliferation and Neointimal Hyperplasia in Rabbits", Circulation, 92, 1570-1575, (1995).

Hehrlein, C., et al., "Pure Beta-particle-emitting Stents Inhibit Neointima Formation in Rabbits", Circulation, 93, 641-645, (1996).

Heldin, et al., "Demonstration of an Antibody Against Platelet-derived Growth Factor," Experimental Cell Research, vol. 136, pp. 255-261 (1981).

Heller, et al., "Preparation of Polyacetals by the Reaction of Divinyl Ethers and Polyols," J. of Polymer Science: Polymer Letters Edition, vol. 18, pp. 293-297 (1980).

Henriksson, et al., Hormonal Regulation of Serum Lp ($\alpha$) Levels; J. Clin. Invest. vol. 89, p. 1166-1171 (1992).

Hermann and Hirshfeld, Jr., "Clinical Use of the Palmaz-Schatz Intracoronary Stent," Futura Publishing Co. (1993).

Hermans et al., "Prevention of restenosis after percutaneous transluminal coronary angioplasty: the search for a "magic bullet"" American Heart Journal, 122 (1) Part, 1, 171-187, 1991.

Hirata et al., "Inhibition of in vitro vascular endothelial cell proliferation and in vivo neovascularization by low-dose methotrexate". Arthritis and Reumatism, 32(9): 1065-1073, 1989.

Hoff, et al., "Modification of Low Density Lipoprotein with 4-Hydroxynonenal Induces Uptake by Macrophages," Arteriosclerosis, vol. 9, No. 4, pp. 538-549 (1989).

Hoffman, A., "Modification of Material Surfaces to Affect How They Interact with Blood, Blood in Contact with Natural and Artificial Surfaces," Leonard, E. et al., (eds), Annals of the New York Academy of Sciences, 516:96-100 (1987).

Hofmann, et al., "Enhancement of the Antiproliferative Effect of cis-Diamminedichloroplatinum(II) and Nitrogen Mustard by Inhibitors of Protein Kinase C," Int. J. Cancer, vol. 42, pp. 382-388 (1988).

Holland, et al., "Atherogenic Levels of Low-density Lipoprotein Increase Endocytotic Activity in Cultured Human Endothelial Cells," Amer. J. of Pathology, vol. 140, No. 3, pp. 551-558 (1992).

Holmes, et al., "Analysis of 1-year clinical outcomes in the SIRIUS trial: a randomized trial of a sirolimus-eluting stent versus a standard stent in patients at high risk for coronary restenosis",Circulation, 109:634-640 (2004).

Holmes, Jr., D.R., "Remodeling Versus Smooth Muscle Cell Hyperpasia", Restenosis Summit VI, The Cleveland Clinic Foundation, 222-223, (1994).

Hoover, et al., "Inhibition of rat arterial smooth muscle cell proliferation by heparin:II. In vitro studies", Circ. Res., 47(4):578-83 (1980).

Hopfenberg, H., "Transport Through Polymers, 7 Encyclopedia of Materials Science and Engineering," (Michael B. Bever, (ed.); The MIT Press, 5141-5145 (1986).

Howell, A., et al, "New Endocrine Therapies for Breast Cancer", European Journal of Cancer, 32A, 576-588, (1996).

Hsu, Li-Chien "Principles of Heparin-Coating Techniques", Perfusion 6: 209-219 (1991).

Huang, et al., "Rapamycins: mechanism of action and cellular resistance." Cancer Biol. Ther., 2(3):222-32 (2003).

Huang, S.S., et al., "Transforming Growth Factor Beta peptide Antagonists and Their Conversion to Partial Agonists", The Journal of Biological Chemistry, 272(43), 27155-57159, 1997.

Huehns, et al., "Adventitia as a Trarget for Intravascular Local Drug Delivery", Heart, 75, 437-438 (1996).

Hughes, D.E., et al., "Estrogen Promotes Apoptosis of Murine Osteoclasts Mediated by TFG-beta", Nature Medicine, 2, 1132-1136, (1996).

Hwang et al., "Effects of Platelet-Contained Growth Factors (PDGF, EGF, IGF-1 and TGF-B) on DNA Synthesis in Porcine Aortic Smooth Muscle Cells in Culture." Exp. Cell Res., 200, 358-360 (1992).

Ishihara, et al., "Synthesis of phospholipid polymers having a urethane bond in the side chain as coating material on segmented polyurethane and their platelet adhesion-resistant properties,"Biomaterials, 1995 16(11): 873-879.

Isner, "Vascular Remodeling: Honey, I Think I Shrunk the Artery", Circulation, 89 2937-2841 (Jun. 1994).

Jacinto and Hall, "Tor signalling in bugs, brain and brawn", Nature Rev. Mol. Cell Biol., 4:117-126 (2003).

Jampel et al., "In vitro release of hydrophobic drugs from polyanhydride disks". Ophthal Surg, 23 (11):676-680, 1991.

Jande et al., "Effects of cytochalasin B and dihydrocytochalasin B on calcium transport by intestinal absorptive cells", Calcif. Tissue Int. 33, 143-151 (1981); Chem. Abs. 94 Abstract No. 189223e (1981).

Jarvis, et al., "Allelopathic Agents from Parthenium hysterophorus and Baccharis megapotamica," Chemistry of Alleopathy, pp. 149-159 (1985).

Jarvis, et al., "Macrocylic and Other Novel Trichothecenes: Their Structure, Synthesis, and Biological Significance," Acc. Chem. Res. 15 pp. 338-395 (1982).

Jeffrey A. Hubbell, Ph.D., "Pharmacologic Modification of Materials" Cardiovasc Pathol vol. 2 No. 3 (Suppl.) Jul.-Sep. 1993,121S-127S.

Jeng, et al., "Regulation of the levels of three transforming growth factor beta mRNAs by estrogen and their effects on the proliferation of human breast cancer cells", Mol. Cell Endocrinol., 92:115-123 (1993).

Jenkins et al., Local Delivery of Taxol Inhibits Neointimal Regrowth Following Balloon Injury of the Rat Carotid Artery:, Circulation, 90, p. I-297, Abrstract No. 1596 (Oct. 1994).

Johnson, et al., "Coronary Atherectomy: Light Microscopic and Immunochemical Study of Excised Tissues," Supp. II Circulation, vol. 78, No. 4, p. II-82 (1988).

Johnston, S.R., et al., "Changes in Estrogen Receptor, Progesterone Receptor, and ps2 Expression in Tamoxifen-resistant Human Breast Cancer", Cancer Research, 55, 3331-3338, (Aug. 1995).

Jones, R.H., et al., "Increased Susceptibility to Metal Catalysed Oxidation of Diabetic Lens beta subL Crystallin: Possible Protection by Dietary Supplementation with Acetylsalicyclic Acid", Exp. Eye Res., 57, 783-790, (1993).

Jordan, A. et al., "Tubulin as a Target for Anticancer Drugs: Agents which Interact with the Mitotic Spindle", Medicinal Research Reviews, 18, 259-296, (1998).

Jordan, V. Craig, "Long-Term Tamoxifen Therapy to Control or to Prevent Breast Cancer: Laboratory Concept to Clinical Trials," Hormones, Cell Biol. and Cancer: Perspectives and Potentials, pp. 105-123 (1988).

Jordan, V.C., et al., "A Mutant Receptor as a Mechanism of Drug Resistance to Tamoxifen Treatment", Annals New York Academy of Science, 761, 138-147, (1995).

Jordan, V.C., et al., "Structural Requirements for the Pharmacological Activity of Nonsteroidal Antiestrogens in Vitro", Molecular Pharmacology, 26, 272-278, (1984).

Jordan, V.C., et al., "Tamoxifen: Toxicities and Drug Resistance During the Treatment and Prevention of Breast Cancer", Annu. Rev. Pharmacol. Toxicol., 35, 195-211, (1995).

Joswig, B.C., et al., "Transmural Myocardial Infarction in the Absence of Coronary Arterial Luminal Narrowing in a Young Man with Single Coronary Arterial Anomaly", Catheterization and Cardiovascular Diagnosis, 4, 297-304, (1978).

Jung, S.M., et al., "Platelet Cytoskeletal Protein Distributions in Two Triton-Insoluble Fractions and How They are Affected by Stimulants and Reagents that Modify Cytoskeletal Protein Interactions" Thrombosis Research, 50 775-787 (1988).

Kakuta, T., et al., "Differences in Compensatory Vessel Enlargement, Not Intimal Formation, Account for Restenosis After Angioplasty in the Hypercholesterolemic Rabbit Model", Circulation, 89, 2809-2815, (1994).

Kakuta, T., et al., "The Impact of Arterial Remodeling on the Chronic Lumen Size After Angioplasty in the Atherosclerotic Rabbit", JACC, Abstract No. 875-95, p. 138A, (Feb. 1994).

Kambic, et al., "Biomaterials in Artificial Organs," Chemical & Engineering News, pp. 31-48 (1986).

Kanzaki, et al., "In vivo effect of TGF-beta 1: enhanced intimal thickening by administration of TGF-beta1 in rabbit arteries injured with a balloon catheter", Arterioscler. Thromb. Vasc. Biol., 15(11):1951-57 (1995).

Kardami et al., "Regulation of cell motility, morphology, and growth by sulfated glycosaminoglycans", Dev. Biol.., 126:19-28 (1988).

Kariya et al., "Antiproliferative action of cyclic GMP-elevating vasodilators in cultured rabbit aortic smooth muscle cells". Atherosclerosis, 80:143-147 (1989).

Kaski, J.C., et al., "Local Coronary Supersensitivity to Diverse Vasoconstrictive Stimuli in Patients with Variant Angina", Circulation, 74, 1255-1265, (1996).

Kastrati et al., "Restenosis after coronary placement of various stent types," Am. J. Cardiol., 87:34-49 (2001).

Ke, H.Z., et al., "Comparative Effects of Droloxifene, Tamoxifen, and Estrogen on Bone, Serum Cholesterol, and Uterine Histology in the Ovariectomized Rat Model", Bone, 20, 31-39, (1997).

Keen, C.L., et al., "Hypertension Induced Alterations in Copper and Zinc Metabolism: A Link to Vascular Disease?", In: Biology of Copper Complexes, Sorenson, J.R.J., (ed.), Humana Press, Clifton, New Jersey, 141-153, (1987).

Kellen, J.A., "Tamaoxifen Beyond the Antiestrogen", BirkhΣuser, 392 pages, (1996).

Kellen, J.A., et al., "The Effect of Toremifene on the Expression of Genes in a Rat Mammary Adenocarcinoma", In Vivo, 10, 511-514, (1996).

Kemp et al., "The Id Gene is Activated by Serum But is Not Required for De-differentiation in Rat Vascular Smooth Muscle Cells," Biochem. J. (Great Britain), vol. 277, pp. 285-288 (1991).

Kemp, P.R., et al., "Cloning and Analysis of the Promoter Region of the Rat SM11-Alpha Gene", Biochem. J., 310, 11043, (1995).

Kemp, P.R., et al., "Inhibition of PDGF BB Stimulated DNA Synthesis in Rat Aortic Vascular Smooth Muscle Cells by the Expression of a Truncated PDGF Receptor", FEBS Letters, 336, 119-123, (Dec. 1993).

Kemp, P.R., et. al., "ID—A Dominant Negative Regulator of Skeletal Muscle Differentiation—is Not Involved in Maturation or Differentiation of Vascular Smooth Muscle Cells", FEBS Letters, 368, 81-86, (1995).

Kim, et al., "Suppression of Vascular Transforming Growth Factor-B1 and Extracellular Matrix Gene Expressions by Cilazapril and Nifedipine in Hypertensive Rats", Clin. Exp. Pharmacaol. Physiol. Suppl., 1, S355, (1995).

Kim, J. et al., "Production of Taxol and Related Taxanes in Taxus brevifolia Cell Cultures: Effect of Sugar", Biotechnology Letters, 17, 101-106, (Jan. 1995).

Kingston, D.G., et al., "Synthesis and Structure-Activity Relationships of Taxol Derivatives As Anticancer Agents", In: New Trends in Natural Products Chemistry, Atta-ur-Rahman, et al., (eds.), Studies in Organic Chemistry, vol. 26, Elsevier Science Publishers B.V., Amsterdam, 219-235, (1986).

Kirk-Othmer, Encyclopedia of Chemical Technology, $33^{rd}$ edition, vol. 17, 1982, John Wiley & Sons, pp. 281-310.

Kirschenlohr, H.L., et al., "Adult Human Aortic Smooth Muscle Cells in Culture Produce Active TFG-Beta", Amer. J. Physiol, 265, C571-C576, (1993).

Kirschenlohr, H.L., et al., "Cultures of Proliferating Vascular Smooth Muscle Cells from Adult Human Aorta", In: Human Cell Culture, Jones, G.E., (ED.), Humana Press, Inc., 24 p. (1996).

Kirschenolohr, H.L., et al., "Proliferation of Human Aortic Vascular Smooth Muscle Cells in Culture is Modulated by Active TGF-Beta", Cardiovascular Research, 29, 848-855, (1995).

Klebe et al., "Regulation of cell motility, morphology, and growth by sulfated glycosaminoglycans", Cell Motil. Cytoskel., 6:273-281 (1986).

Klein, H.O. et al., "Experimental Investigations on a Sequential Combination Chemotherapy Protocol" J. Cancer Res. Clin. Oncol vol. 96 No. 2 Jan. 1980 p. 65-78.

Kleinman, N.S., et al., "Prinzmetal's Angina during 5-Fluorouracil Chemotherapy", The American Journal of Medicine, 82, 566-568, (1987).

Knabbe, C., et al., "Induction of Transforming Grown Factor-B by the Antiestrogens Droloxifene, Tamaoxifen, and Toremifene in MCF-7 Cells", Am. J. Clin. Oncol. 14, S15-S20, (1991).

Koff, et al., Negative Regulation of GI in Mammalian Cells: Inhibition of Cyclin E-Dependent Kinase by TGF-β, Science, vol. 260, pp. 536-538 (1993).

Kopp, A., et al., "Transforming Growth Factor Beta2 (TGF-Beta2) Levels in Plasma of Patients with Metastatic Breast Cancer Treated with Tamoxifen", Cancer Research, 55, 4512-4515, (Oct. 15, 1995).

Kost, J. Langer R, "Controlled Release of Bioactive Agents," Trends in Biotechnology, vol. 2, No. 2, 1984, pp. 47-51.

Kotoulas, I.G., et al., "Tamoxifen Treatment in Male Infertility. I. Effect on Spermatozoa", Fertility and Sterility, 61, 911-914, (May 1994).

Kovach, et al., "Serial Intravascular Ultrasound Studies Indicate That Chronic Recoil Is An Important Mechanism Of Restenosis Following Transcatheter Therapy," JACC vol. 484A, Abstract 835-3 (1993).

Koyama, N., et al., "Regulation of Smooth Muscle Cells Migration by a New Autocrine Migration Factor and TGF-beta", Circulation, 84, Abstract No. 1829, II-459, (1991).

Kremer, J.M., et al., "Fish-Oil Fatty Acid Supplementation in Active Rheumatoid Arthritis", Annals of Internal Medicine, 106, 497-502, (1987).

Kunert, et al., Paclitaxel Inhibits Developpment of Restenosis Following Experimental Balloon Angioplasty in the Rabbit Carotid Artery:, European Heart Journal, 17, Abstract No. P1998, p. 368 (1996).

Kunz et al., "Defining Coronary Restenosis Newer Clinical and Angiographic Paradigms". Circulation, 88 1310-1323 (Sep. 1993).

Kunz et al., "Sustained Dilation and Inhibition of Restenosis in a Pig Femoral Atery Injury Model". Circulation, 90, p. 1-297, Abstract No. 1598 (Oct. 1994).

Kunz et alk., "Inhibition of Microfilament Reorganization Following Balloon Angioplasty Decreases Extent of Geometric Remodeling in Restenosis,"J. of Amer. Coll. of Cardiology, AMerican College of Geometric Cardiology $44^{th}$ Annual Scientific Session, Abstract No. 122292. (Mar. 19-22, 1995).

Kunz, L.L., et al., "Efficacy of Cytochalasin B in Inhibiting Coronary Restenosis Caused by Chronic Remodeling After Balloon Trauma in Swine", Journal of the American College of Cardiology, Supplement A., Abstract No. 984-23, p. 302, (Mar. 1995).

Kuramochi, H., "Conformational Studies and Electronic Structures of Tamoxifen and Toremifene and Their Allylic Carbocations Proposed as Reactive Intermediates Leading to DNA Adduct Formation", J. Med. Chem., 39, 2877-2886, (1996).

Kuzana, S., et al., "Effects of Some Anti-Rheumatic Agents on Copper-Catalyzed Thermal Aggregation of Gamma Globulin", Agents and Actions, 9 375-380, (1979).

L C.. Palmaz et. al., Expandable Intraluminal Graft: A Preliminary Study, Radiology 1985;1:73-77.

Labhsetwar et al., "Nanoparticles for site specific delivery of U-86983 in restenosis on pig coronary arteries," Proc . Intern. Symp. Control. Rel. Bioact. Mater. 22, 182-183 (1995).

LaFont, et al., "Post-angioplasty Restenosis In The Atherosclerotic Rabbit: Proliferative Response Or Chronic Constriction?," Circulation, vol. 88, I-521, Abstract 2806 (1993).

Laird, J., et al., "Inhibition of Neointimal Proliferation with Low-dose Irradiation from a Beta-particle-emitting Stent", Circulation, 93, 529-536, (1996).

Lambert et al., "A new method for arterial drug delivery via removable stent". JACC, 21(2):483A, #834-2, 1992.

Lambert, et al., "Local Drug Delivery Catheters: Functional Comparison of Porous and Microporous Designs," Coronary Artery Disease, vol. 4, No. 5, pp. 469-475 (1993).

Langbein, W., "Too Many Drugs, Too Little Value in CV Conditions", In Vivo, 14-20, (Jun. 1995).

Lange, R.A., et al., "Cocaine-Induced Coronary-Artery Vasoconstriction", The New England Journal of Medicine, 321, 1557-1562, (1989).

Lange, R.L., et al., "Nonatheromatous Ischemic Heart Disease following Withdrawal from Chronic Industrial Nitroglycerin Exposure", Circulation, 46, 666-678, (1972).

Langer, R. et al., "Polymeric Delivery Systems for Macromolecules-Approaches for Studying In Vivo Release Kinetics and Designing Constant Rate Systems", in: *Biological Activities of Polymers*, Carraher, Jr. and Gebelein (eds), American Chemical Society Symposium Series 186, pp. 95-105 (1982).

Langer, R., "New Methods of Drug Delivery", Science, vol. 249, 28.09 1990, pp. 1527-1533.

Langer, R., "Polymeric Delivery Systems for Controlled Drug Release", Chem. Eng. Communi. 6:1-48 (1980).

Law et al., "Rapamycin potentiates transforming growth factor beta-induced growth arrest in nontransformed, oncogene-transformed, and human cancer cells", Mol.. Cell. Biol., 22:8184-8198 (2002).

Lawn, R.M., et al., "Feedback Mechanism of Focal Vascular Lesion Formation in Transgenic Apolipoprotein(a) Mice", The Journal of Biological Chemistry, 271, 31367-31371, (1996).

Lazier, C.B., et al., "Comparison of the Effects of Tamoxifen and of a Tamoxifen Analogue that Does Not Bind the Estrogen Receptor on Serum Lipid Profiles in the Cockerel", Biochem. Cell Biol., 68, 210-217, (1990).

LC. Palmaz et al., Expandable Intraluminal Vascular Graft: A Feasibility Study, Surgery Feb. 1986; 199(2): 199-205.

Lefer, Allen M., "Role of Transforming Growth Factor β in Cardioprotection of the Ischemic-Reperfused Myocardium," Growth Factors and the Cardiovascular System, Chapter 14 (Cummins, P. ed.), Kluwer Academic Publishers, pp. 249-260 (1993).

Lefer, et al., "Mechanism of the Cardioprotective Effect of Transforming Growth Factor $β_1$, in Feline Myocardial Ischemia and Reperfusion," PNAS (USA), vol. 90, pp. 1018-1022 (1993).

Lefer, et al., "Mediation of Cardioprotection by Transforming Growth Factor-β," Science, vol. 249, pp. 61-64 (1990).

Lehmann, K. et al., "Effect of cilazapril on the proliferative response after vascular damage", J. of Cardiovascular Pharmacology, 22 (Suppl. 4), S19-24, (1993).

Lehmann-Bruinsma, et al., "Transforming Growth Factor B2 (TGF-B) Suppression of Smooth Muscle Cell (SMC) Proliferation After Balloon Angioplasty of Rat Carotid Arteries", Clin. Res. 42, Abstract No. 4A, (Feb. 9-12, 1994).

Leroux et al., "Internalization of poly(D L-lactic acid) nanoparticles by isolated human leukocytes and analysis of plasma proteins adsorbed onto the particles," J. Biomed. Mater. Res., 28, 471-481 (1994).

Levy, "Drug Release from Submicronized O/W Emulsion: A New In Vitro Kinetic Evaluation Model", Intl. J. Pharmaceut. ,66, 29-37 (1990).

Levy, et al., "Strategies for Treating Arterial Restenosis Using Polymeric Controlled Release Implants," Abstracts, Proc. Am. Chem. Soc. Symp., In: Biotechnol. Bioact. Poly., C.G. Gebelein, (ed.), pp. 359-268 (1992).

Levy, et al., "Strategies for Treating Arterial Restenosis Using Polymeric Controlled Release Implants," Chemical Abstracts, 121, 580: Abstract No. 263625g (1994).

Li, et al., "Structure and Dynamics of Microemulsions which Mimic the Lipid Phase of Low-Density Lipoproteins", Biochimica et Biophysica Acta, 1042, 42-50 (1990).

Liau and Chan, "Regulation of extracellular matrix RNA levels in cultured smooth muscle cells: relationship to cellular quiescence", J. Cell Biol., 264:10315-10320 (1989).

Liaw, et al., "Osteopontin Promotes Vascular Cell Adhesion and Spreading and Is Chemotactic for Smooth Muscle Cells In Vitro," Cir. Res. vol. 74, No. 2, pp. 214-224 (1994).

Lichtlen et al., "Retardation of angiographic progression of coronary artery disease by nifedipine", Lancet, 335:1109-1113 (1990).

Lin, et al., "Expression Cloning of the TGF-β Type II Receptor, a Functional Transmembrane Serine/Threonine Kinase," Cell. vol. 68, pp. 775-785 (1992).

Lincoff et al., "Local Drug Delivery for the Prevention of Restenosis" Circulation, 90 2070-2084 (Oct. 1994).

Lindkaer-Jensen, S., et al., "Inhibition of Salicylate and Lithium Absorption in the Human Intestine by Copper Sulfate", Arch. Toxicol., 35, 175-179, (1976).

Lindner, "Vascular repair processes mediated by transforming growth factor-beta, Z Kardiol", 90 Suppl 3:17-22 (2001).

Lippold, B.C., "Retardarzneiformen" in E. Numberg, Hagers Handbuch der pharmazeutischen Praxis, vol. 2, Springer-Verlag Berlin Heidelberg New York, 5th edition, 1991 pp. 832-840.

Lippman and Mathews, "Heparins: varying effects on cell proliferation in vitro and lack of correlation with anticoagulant activity", Fed. Proc., 36:55-59 (1977).

Lipski, et al., "Cytochalasin B: Preparation, Analysis in Tissue Extracts, and Pharmacokinetics After Intraperitoneal Bolus Administration In Mice," Analytical Biochem., vol. 161, pp. 332-340 (1987).

Liu et al., "Trapidil in preventing restenosis after balloon angioplasty in the atherosclerotic rabbit", Circulation, 81(3): 1089-1093 (1990).

Liu, et al., "Restenosis After Coronary Angioplasty—Potential Biologic Determinants and Role of Intimal Hyperplasia," Circulation, vol. 79, No. 6, pp. 1374-1387 (1989).

Lopez-Anaya, A., et al., "Pharmacokinetics and Pharmacodynamics in Copper Deficiency I", Biological Trace Element Research, 40, 161-176, (1994).

Lopez-Casillas, et al., "Beta-glycan Presents Ligand to the TGFBeta Signaling Receptor", Cell, 73, 1435-1444, (Jul. 2, 1993).

Loser, R., et al., "In Vivo and in Vitro Antiestrogenic Action of 3-Hydroxytamoxifen, Tamoxifen and 4-Hydroxytamoxifen", Eur. J. Cancer Clin. Oncol., 21, 985-990, (1985).

Love, et al., "Effects of Tamoxifen on Cardiovascular Risk Factors in Postmenopausal Women," Annals of Internal Medicine, vol. 115, No. 11, pp. 860-864 (1991).

Love, et al., "Effects of Tamoxifen Therapy on Lipid and Lipoprotein Levels in Postmenopausal Patients with Node-Negative Breast Cancer," J. of the National Cancer Institute, vol. 82, No. 16, pp. 1327-1332 (1990).

Lowe, et al., "Coronary In-Stent Restenosis: Current Status and Future Strategies", Journal of the American College of Cardiology, 1992, vol. 39 No. 2, pp. 183-193.

Luan et al., "Rapamycin is an effective inhibitor of human renal cancer metastasis", Kidney Int., 63:917-926 (2003).

Lucas, C., et al., "The Authocrine Production of Transforming Growth Factor-B1 During Lymphocyte Activation", The Journal of Immunology, 145(5), 1415-1422, (1990).

Ludwig K. von Segesser, MD., Heparin-Bonded Surfaces in Extracorporeal Membrane Oxygenation for Cardiac Support:, The Society of THoracic Surgeons, (1996).

Luo, H. et al., "Chronic Vessel Constriction is an Important Mechanism of Restenosis After Balloon Angioplasty: An Intravascular Ultrasound Analysis", Circulation, 90, 67 Scientific Sessions, Abstract No. 0318, p. 1-61, (1994).

Luostarinen, R., et al., "Effect of Dietary Fish Oil Supplemented with Different Doses of Vitamin E on Neutrophil Chemotaxis in Healthy Volunteers", Nutrition Research, 12, 1419-1430, (1992).

Lutgens et al., "Transforming growth factor-beta mediates balance between inflammation and fibrosis during plaque progression", Arterioscler. Thromb. Vasc. Biol., 22:975-982 (2002).

Lyons et al., "Mechanism of activation of latent recombinant transforming growth factor beta1 by plasmin", J. Cell. Biol., 110:1361-1367 (1990).

Macander et al., "Balloon Angioplasty for Treatment of In-Stent Restenosis: Feasibility, Safety, and Efficacy", Catheterization and Cardiovascular Diagnosis, 32 125-131 (1994).

Madri et al., "Endothelial cell behavior after denudation injury is modulated by transforming growth factor-beta1 and fibronectin", Lab. Invest., 60:755-764 (1989).

Magarian, "The Medicinal Chemistry of Nonsteroidal Antiestrogens: A Review", Current Medicinal Chemistry, 1, 61-104, (1994).

Maione, Theodore E. and Sharpe, Richard J. "Development of angiogenesis inhibitors for clinical applications" TiPS- Nov. 1990 [vol. 11].

Majack, "Beta-type transforming growth factor specifies organizational behavior in vascular smooth muscle cell cultures", J. Cell Biol., 105:465-471 (1987).

Majack, R.A., et al., "Role of PDGF-A Expression in the Control of Vascular Smooth Muscle Cell Growth by Transforming Growth Factor-B", The Journal of Cell Biology, 111, 239-247, (1990).

Majesky, M.W., et al., "Production of Transforming Growth Factor beta1 During Repair of Arterial Injury", J. Clin. Invest., 88, 904-910, (1991).

Malcolmson, et al., "A Comparison Between Nonionic Micelles and Microemulsions as a Means of Incorporating the Poorly Water Soluble Drug Diazepam", J. Pharm. Pharmacol, 42 6p, (1990).

Mambetisaeva, E.T., et al. "Effect of New Synthetic Cholesterol Derivatives on Cholesterol Metabolism in Cultured Rabbit Hepatocytes", Biokhimiya (Russia), 58, Translation, Plenum Publishing Corporation, 1126-1132, (1993).

Manasek, et al., The Sensitivity of Developing Cardiac Myofibrils to Cytochalasin-B, PNAS (USA), vol. 69, No. 2, pp. 308-312 (1972).

Manucci, P.M., et al., "Effect of Tamoxifen on Measurements of Hemostatis in Healthy Women", Arch. Intern. Med., 156, 1806-1810, (1996).

Marx and Marks, "Bench to Bedside: The development of rapamycin and its application to stent restenosis", Circulation 104:852-55 (2001).

Marx, "CMV-p. 53 Interaction May Help Explain Clogged Arteries", Science, 265, 320, (Jul. 1994).

Marzocchi, A., et al., "Restenosis after Coronary Angioplasty: It's Pathogenesis and Prevention," Cardiologia, 36, 309-320 (Dec. 1991) English Abstract only, reported in Medline, Accession No. 93046311.

Massague and Wotton, "Transcriptional control by the TGF-beta/Smad signaling system", EMBO J., 19(8):1745-54 (2000).

Massague et al., "Type beta transforming growth factor is an inhibitor' of myogenic differentiation", Proc,. Natl. Acad. Sci., 83:8206-8210 (1986).

Massagué, Joan, "The Transforming Growth Factor-B; Family", Annu. Rev. Cell Biol. vol. 6, pp. 597-641 (1990).

Massague,"Subunit structure of a high-affinity receptor for' type beta-transforming growth factor: evidence for a disulfide-linked glycosylated receptor complex", J. Biol. Chem., 260(11):7059-7066 (1985).

McAuslan, B.R., et al., "Cellular and Molecular Mechanisms in Angiogenesis", Trans. Ophthal. Soc. U.K., 100, 354-358, (1980).

McCaffrey et al, "Genomic instability in the type II TGF-b1 receptor gene in atherosclerotic and restenotic vascular cells," J Clin Invest, 100:2182-2188 (1997).

McCaffrey et al., "Aging and arteriosclerosis: the increased proliferation of arterial smooth muscle cells isolated from old rats is associated with increased platelet-derived growth factor-like activity," J. Exp. Med., 167:163-174 (1988).

McCaffrey et al., "Decreased type II/type I TGF-beta receptor ratio in cells derived from human atherosclerotic lesions. Conversion from an antiproliferative to profibrotic response to TGF-beta1", J. Clin. Invest., 96:2667-2675 (1995).

McCaffrey, "TGF-betas and TGF-beta receptors in atherosclerosis," Cytokine and Growth Factor Rev., 11:103-114 (2000).

McCaffrey, et al., "Transforming Growth Factor; β Activity is Potentiated by Heparin Via Dissociation of the Transforming Growth Fact—Macroglobulin Inactive Complex," The J. of Cell Biology, vol. 109, pp. 441-448 (1989).

McCaffrey, T.A., et al., "Fucoidan is a Non-Anticoagulant Inhibitor of Intimal Hyperplasia", Biochemical and Biophysical Research Communications, 184, 773-781, (1992).

McCague, R., et al., "An Efficient, Large Scale Synthesis of Idoxifene ((E)-1(4- (2- (N-pyrrolidino) ethoxyl) -1-(4-iodophenyl) -2-phenyl-1-butene)", Organic Preparations and Proc. Int., 26, 343-346, (1994).

McCague, R., et al., "Synthesis of 4-Stannylated Tamoxifen Analogues: Useful Precursors to Radiolabelled Idoxifene and Axiridinyl 4-Iodotamoxifen.", J. Labelled Compounds and Pharmaceuticals, 34, 297-302, (1994).

McCarroll, et al., Preliminary Studies on the Regulation of Secretion of Latent Transforming Growth Factor-β (TGF-β) by Endothelial Cells in Culture, Clin. Chem. vol. 36, No. 6, pp. 1152 (1990) Abstract No. 0934.

McClean, et al., "cDNA sequence of human apolipoprotein (a) is homologous to plasminogen", Nature, 330, 132-137 (1987), 132-137, (1987).

McCormick, et al., "Retinoid-Tamoxifen Interaction in Mammary Cancer Chemoprevention," Carcinogenesis, vol. 7, No. 2, pp. 193-196 (1986).

McDonald, C.C., et al., "Cardiac and vascular morbidity in women receiving adjvant tamoxifen for breast cancer in a randomised trial", BMJ, 311, 977-980, (Oct. 14, 1995).

McDonald, et al., "Fatal Myocardial Infarction in the Scottish Adjuvant Tamoxifen Trial," BNJ, vol. 303 pp. 435-437 (1991).

McDonnell, D.P., et al., "Analysis of Estrogen Receptor Function in Vitro Reveals Three Distinct Classes of Anti estrogens", Molecular Endocrinology, 9, 65-669, (Jun. 1995).

McLaughlin, C.S., et al., "Inhibition of Protein Synthesis by Trichothecenes", In: Mycotoxins in Human and Animal Health, Pathotox Publishers, Inc., 263-273, (1977).

McMurray et al., "A standardised method of culturing aortic explants, suitable for' the study of factors affecting the phenotypic modulation, migration and proliferation of aortic smooth muscle cells," Atherosclerosis, 86:227-237 (1991).

McQuiggan, James Daniel: "Tissue Distribution of Cytochalasin B After Intraperitoneal Bolus and Microencapsulated Injection in Mice and its Effect on β-N-Acetylglucosaminidase Activity in Cultured B16-BL6 Melanoma Cells," Thesis Submitted in partial fulfillment of the requirements for the degree of Master of Science in Biology in the Graduate School of Syracuse University, published Syracuse University, Biology Dept. (1988).

Meiser et al., "Effectsof Cyclosporin, Fk506, and Rapamycin on Graft-Vessel Disease", The Lancet, 338, 1297-1298 (1991).

Merck Index,, (Susan Budavari et al, ed.) 1989, p. 1435.

Merrilees and Scott, "Antisense S-oligonucleotide against transforming growth factor-beta 1 inhibits proteoglycan synthesis in arterial wall," L Vase. Res. 31:322-329 (1994).

Merrilees et al., "Effect of TGF-beta(1) antisense S-oligonucleotide on synthesis and accumulation of matrix proteoglycans in balloon catheter-injured neointima of rabbit carotid arteries, 3". Vase. Res. 37:50-60 (2000).

Merrilees, et al., "Synthesis of TGF-β₁ by Vascular Endothelial Cells is Correlated with Cell Spreading," J. Vasc. Res., vol. 29, pp. 376-384 (1992).

Metcalfe et al., "Calcium and cell proliferation," Br. Med.. Bull., 42(4):405-4t2 (1986).

Metcalfe, et al., "Protein Markers of Lesion Development in the Vessels of Transgenic Apo(a) Mice" Inflammation, Growth Regulatory Molecules & Atherosclerosis, J. Cellular Biochem., SUpplement 18A, p. 208, Abstract No. E212 (1994).

Meyer, S.C., "Functionalized Cytochalasins for Potential Biotechnology Transfer", Ph. D. Thesis (Selected Pages), Syracuse University, New York, 13 p., (May 1994).

Michael N. Helmus, "Materials Selection, Chapter 2," Encyclopedic Handbook of Biomaterials and Bioengineering, Part A: Materials, vol. 1 (1995).

Michael N. Helmus, Materials Selection, Chapter 6, Cardiovsc. Pathol. 2(3)(Suppl.):53s-71s (Jul.-Sep. 1993).

Michael N. Helmus, "Materials Selecton for Medical Devices," Spectrum, 1-21, (Jul. 30, 1993).

Michael N. Helmus, "Medical Device Design—A Systems Approach: Central Venous Catheters", (1990).

Michael N. Helmus, "Opportunities for Biomaterials," DH Reports, (Feb. 1995).

Michael N. Helmus, "Technological Advances in Thromboresistant Materials," Spectrum, 1-13 (Jun. 19, 1990).

Michael N. Helmus, "Thromboresistant Biomaterials: Technical Developments and Applications," Spectrum, (Sep. 12, 1990).

Middlebrook, et al., "Specific Association of T-2 Toxin with Mammalian Cells," Biochem. Pharmacology, vol. 38, No. 18, pp. 3093-3102 (1989).

Middlebrook, J.L., et al., "Binding of T-2 Toxin to Eukaryotic Cell Ribosomes", Biochemical Pharmacology, 38 33110, (1989).

Milner, M.R., et al., "Usefulness of Fish Oil Supplements in Preventing Clinical Evidence of Restenosis After Percutaneous Transluminal Coronary Angioplasty", Am. J. Cardiol., 64, 294-299 (1989).

Mintz, G.S., et al., "Chronic Compensatory Arterial Dilation Following Coronary Angioplasty: An Intravascular Ultrasound Study", JACC, Abstract No. 875-97, p. 138A, (Feb. 1994).

Mintz, G.S., et al., "Geometric Remodeling is the Predominant Mechanism of Clinical Restenosis After Coronary Angioplasty", JACC, Abstract No. 875-42, p. 138A, (Feb. 1994).

Mintz, G.S., et al., "Mechanisms of Late Arterial Response to Transcatheter Therapy: A Serial Quantitative Angiographic and Intravascular Ultrasound Study", Circulation, 90, Abstract No. 117, p. 1-24, (Oct. 1994).

Mirjalili, N. et al., "Methyl Jasmonate Induced Production of Taxol in Suspension Cultures of Taxus Cuspidata: Ethylene Interaction and Induction Models", Biotechnol. Prog., 12, 110-118, (1996).

Mirjalili, N., et al., "Gas Phase Composition Effects on Suspension Cultures of Taxus cuspidata", Biotechnology and Bioengineering, 48, 123-132, (1995).

Mitchell, L.L., et al., "Copper Deficiency Depresses Rat Aortae Superoxide Dismutase Activity and Prostacyclin Synthesis", Prostaglandins, 35, 977-986, (1988).

Molling, K., "Naked DNA for Vaccine or Therapy", J. Mol. Med., 75, 242-246, (1997).

Moorthy, B., et al., "Tamoxifen Metabolic Activation: Comparison of DNA Abducts Formed by Microsomal and Chemical Activation of Tamoxifen and 4-Hydroxytamoxifen with DNA Abducts Formed in Vivo", Cancer Research, 56, 53-57, (Jan. 1, 1996).

More et al., "A Targeted Antithrobotic Conjugate with Antiplatelet and Fibrinolytic Properties which reduces in vivo Thrombus Formation", Cardiovascular Research, 27, 2200-2204 (1993).

Morisaki, et al., "Effects of Transforming Growth Factor β on Growth of Aortic Smooth Muscle Cells," Atherosclerosis, vol. 88, pp. 227-234 (1991).

Morris et al., "Rapamycin (sirolimus) inhibits vascular smooth muscle DNA synthesis in vitro and suppresses narrowing in arterial allografts and in balloon-injured carotid arteries: evidence that rapamycin antagonizes growth factor action on immune and nonimmune cells," Transplant Proc, 27:430-31 (1995).

Morris, R.E., "Rapamycins: Antifungal, Antitumor, Antiproliferative, and Immunosuppressive Macrolides", Transplantation Reviews, 6, 39-87, (1992).

Morris, R.E., et al., "Immunosuppressive Effects of the Morpholinoethyl Ester of Mycophenolic Acid (RS-61443) in Rat and Nonhuman Primate Recipients of Heart Allografts", Transplantation Proceedings, 23, 19-25, (1991).

Mosedale and Grainger, "An antibody present in normal human serum inhibits the binding of cytokines to their receptors in an in vitro system," Biochem J., 343:125-133 (1999).

Mosedale, D.E. University of Cambridge Ph.D. Thesis, Differentiated state of smooth muscle and its relationship to TGF-β in vivo, DJG 005652-005910 (1998) and all references therein.

Mosedale, D.E., et al., "Transforming Growth Factor-beta is Correlated with Smooth Muscle Cell Differentiation in Vivo", Circulation, 90, 67th Scientific Session, Abstract No. 1590, p. 1-296, (Oct. 1994).

Moses and Langer "Inhibitors of angiogenesis". Bio/Technology. 9:630-634, 1991.

Murphy, C.S., et al., "Structural Components Necessary For The Antiestrogenic Activity of Tamoxifen", J. Steroid Biochem, 34, 1-6 (1989).

Murphy, C.S., et al., "Structure-Activity Relationships of Nonisomerizable Derivatives of Tamoxifen: Importance of Hydroxyl Group and Side Chain Positioning for Biological Activity", Molecular Pharmacology, 39, 421-428, (1991).

Murphy, L.C., et al., "Differential Effects of Tamoxifen and Analogs with Nonbasic Side Chains on Cell Proliferation in Vitro", Endocrinology, 116, 1071-1078, (1985).

Myer, R.O, et al., "Performance and Carcass Characteristics of Swine When Fed Diets Containing Canola Oil and Added Copper to Alter the Unsaturated:Saturated Ration of Pork Fat", J. Anim. Sci., 70, 1417-1423, (1992).

Nabel, "Recombinant Gene Expression in Vivo Within Endothelial Cells of the Arterial Wall", Science, 244, 1342-1344 (1983).

Nabel, E.G., et al., "Direct Transfer of Transforming Growth Factor Beta 1 Group Into Arteries Stimulates Fibrocellular Hyperplasia", Proc. Natl. Acad. Sci. USA 90, 10759-10763, (1993).

Nagakawa, Y., et al., "Effect of Eicosapentaenoic Acid on the Platelet Aggregation and Composition of Fatty Acid in Man", Atherosclerosis, 47, 71-75, (1983).

Naito, et al., "Vascular Endothelial Cell Migration In Vitro Roles of Cyclic Nucleotides, Calcium Ion and Cytoskeletal System," Artery, vol. 17(1), pp. 21-31 (1989).

Nakagawa, et al., "A Case of Acute Myocardinal Infarction Intracoronary Arteries Due To Hormone Therapy.", Angiology, 45, 333-338, (May 1994).

Nakano, Glucocorticoid Inhibits Thromin-Induced Expression of Platelet-Derived Growth Factor A-chain and Heparin-Binding Epidermal Growth Factor-Like Growth Factor in Human Aortic Smooth Muscle Cells:, The Journal of Biological Ch emistry, 268, 22941-22947 (1993).

Nakao, et al., "Calcium Dependency of Aortic Smooth Muscle Cell Migration Induced by 12-L-Hydroxy-5,8,10,14-eicosatetraenoic Acid," Atherosclerosis, vol. 46, pp. 309-319 (1983).

Navarro, S.E., et al., "Notes from Transcatheter Cardiovascular Therapeutics 1995 Conference", USB Securities, Equity Research—Medical Technology, 10 p., (Mar. 3, 1995).

Nayfield, S.G., et al., "Tamoxifen-Associated Eye Disease: A Review", Journal of Clinical Oncology, 14(3), 1018-1026, (1996).

Nikol et al., "Persistently increased expression of the transforming growth-factor-131 gene in human vascular restenosis: Analysis of 62 patients with one or more episode of restenosis," Cardiovasc. Pathol., 3:57-64 (1994).

Nikol, et al., "Expression of Transforming Growth Factor $\beta_1$ is Increased in Human Vascular Restenosis Lesions," J. Clin. Invest., vol. 90, pp. 1582-1592 (1992).

Nunes, et al., "Vitamins C and E Improve the Response to Coronary Balloon Injury In the Pig: Effect of Vascular Remodeling," Circulation, vol. 88, No. 4, Part 2, p. I-372 (1993).

O'Brien, et al., "Osteopontin mRNA and Protein are Overexpressed in Human Coronary Atherectomy Specimens: Clues to Lesion Calcification," Cir. vol. 88, p. I-619, Abstracts from the 66th Scientific Sessions (1993).

O'Connor-McCourt, et al., "Latent Transforming Growth Factor β in Serum: A Specific Complex with $_2$-Macroglobulin," The Journal of biological Chemistry, vol. 262, No. 29, pp. 14090-14099 (1987).

O'Leary, V.J., et al., "The Resistance of Low Density Lipoprotein to Oxidation Promoted by Copper and Its Used as an Index of Antioxidant Therapy", Atherosclerosis, 119, 169-179, (1996).

Ohmi, et al., "Effect of K252a, A Protein Kinase Inhibitor, on the Proliferation of Vascular Smooth Muscle Cells," Biochemical and Biophysical Research Communications, vol. 173, No. 3, p. 976-981 (1990).

Ohno, et al., "Gene Therapy for Vascular Smooth Muscle Proliferation After Afterial Injury", Science, 265, 781-784, (Aug. 5, 1994).

O-Keefe Jr. et al., "Ineffectiveness of colchicine for the prevention of restenosis after coronary angioplasty". JACC, 19(7): 1597-1600, 1992.

Okuyyama, S., et al., "Copper Complexes of Non-Steroidal Anti-inflammatory Agents: Analgesic Activity and Possible Opoid Receptor Activation", Agents and Actions, 21, 130-144, (1987).

Oliveira, et al., "Isolation and Characterization of Smooth Muscle Cell Membranes," Biochimica et Biophysica Acta. vol. 332, pp. 221-232 (1974).

Opherk, D., et al., "Four-Year Follow-up Study in Patients With Angina Pectoris and Normal Coronary Arteriograms ("Syndrome X")", Circulation, 80, 1610-1616, (1989).

Orlov, S.N., et al., "Altered beta-Adrenergic Regulation of Na—K—Cl Cotransport in Cultured Smooth Muscle Cells Form the Aorta of Spontaneously Hypertensive Rats", American Journal of Hypertension, 8, 739-747, (1995).

Osborne, et al., "Microemulsions as Topical Drug Delivery Vehicles: In Vitro Trandermal Studies of a Model Hydrophilic Drug", J. Pharm. Pharmacol., 43, 451-454 (1991).

Osborne, M.R., et al., "Identification of the Major Tamoxifen-Deoxyguanosine Adduct Formed in the Liver DNA of Rats Treated with Tamoxifen", Cancer Research, 56, 66-71, (1996).

Osipow, "Transparent Emulsion" J. Soc. Cosmetic Chemists, 277-285 (1963).

Owens, G.K., et al., "Transforming Growth Factor-B-induced Growth Inhibition and Cellular Hypertrophy in Cultured Vascular Smooth Muscle Cells", The Journal of Cell Biology, 107, 771-780, (1988).

Ozer, et al., "New Roles of low density lipoproteins and vitamin E in the pathogenesis of atherosclerosis", Biochem Mol. Biol. Intern, 35, 117-124, (1995).

Palmaz et al., "Balloon Expandable Intraluminal Grafting of Normal and Abnormal Renal Arteries: Experimental Study," Radiology Nov. 1986; 161 (P):40-41 Abstract 85.

Palmaz et al., "Expandable Intrahepatic Portacaval Shunt Stents in Dogs with Chronic Portal Hypertension," A JR 1986 Dee; 147:1251-54.

Palmaz et al., "Expandable Intrahepatic Portacaval Shunt Stents: Early Experience in the Dog," 145 Am. J. Roentgenol. 1985;145:821-825.

Palmaz et al., "Expandable Intraluminal Grafting in Atherosclerotic Rabbit Aortas," Radiology Nov. 1985; 157(P):66 Abs 130.

Palmaz et al., "Intravascular Stents", Advances in Vascular Surgery, 1, 107-135 (1993).

Palmaz et al., "Normal and Stenotic Renal Arteries: Experimental Balloon-expandable Intraluminal Stenting," Radiology Sep. 1987; 164(3):705-708.

Palmaz et al., "Removable Biliary Endoprosthesis," Am, J. Roentgenol. 1983;l40(4):812-4.

Palmaz, et al., "Atherosclerotic Rabbit Aortas: Expandable Intraluminal Grafting," Radiology Sep. 1986; 160:723-726.

Palmaz, et al., "Intravascular Stents: Basic Physical and Biological Properties, Endoluminal Treatment: The Different Techniques.". Editors Michel Henry, Max Arnor, Edward B. Diethrich and Barry Katzen. Published by Springer Verlag; 4:149-158 (1997).

Palmaz, J.C. "Expandable Intraluminal Graft: A Preliminary Study," Radiology Nov. 1984; 153(P):329 Abs. 993.

Palmaz, J.C., "Balloon-Expandable Intravascular Stent", Am. J. of Radiol. 150:1263-1269 (1988).

Pandey, B.L., et al., "A Study of the Effects of Tamrabhasma, an Indigenous Preparation of Copper on Experimental Gastric Ulcers and Secretion", Indian Journal of Experimental Biology, 21, 258-264, (1983).

Pardee, et al., "Control of Cell Proliferation," Cancer, vol. 39, pp. 2747-2754 (June Supplement 1977).

Pardoll, D., et al., "Exposing the Immunology of Naked DNA Vaccines", Immunity, 3, 165-169, (1995).

Parthasatathy, S., et al., "A Role for Endothelial Cell Lipoxygenase in the Oxidative Modification of Low Density Lipoprotein", Proc. Nat'l Acad. Sci., USA, 86, 1046-1050, (1989).

Pathak, et al., "Enhanced Stability of Physostigmine Salicylate in Submicron o/w Emulsion", International Journal of Pharmaceutics, 65, 1690175 (1990).

Pedron, N. et al., "The Effect of Acetylsalicyclic Acid on Menstrual Blood Loss in Women with IUDs", Contraception, 36, 295-303, (1987).

Peng et al., "The immunosuppressant rapamycin mimics a starvation-like signal distinct from amino acid and glucose deprivation," Mol. Cell.. Biol., 22:5575-84 (2002).

Pennisi, E., "Drug's Link to Genes Reveals Estrogen's Many Sides", Science, 273, 1171, (Aug. 30, 1996).

Peress, N.S., et al., "Differential Expression of TGF-B1, 2 and 3 Isotypes in Alzheimer's Disease : A Comparative Immunohistochemical Study with Cerebral Infarction, Aged Human and Mouse Control Brains", Journal of Neuropathology and Experimental Neurology, 54, 802-811, (Nov. 1995).

Peress, N.S., et al., "Glial Transforming Growth Factor (TGF) -B Isotypes in Multiple Sclerosis: Differential Glial Expression of TGF-B1, 2, and 3 Isotypes in Multiple Sclerosis", Journal of Neuroimmunology, 71, 115-123, (1996).

Perez, J.R., et al., "Regulation of Adhesion and Growth of Fibrosarcoma Cells by NF—kb RelA Involves Transforming Growth Factor Beta", Molecular and Cellular Biology, 14, 5326-5332, (1994).

Pfister, W.R. et al., "Silicone Based Sustained and Controlled Release Drug Delivery Systems", 1985, 30$^{th}$ National SAMPE Symposium and Exhibition, Anaheim, CA, Mar. 19-21, 1985, pp. 490-498 (1985).

Pinto, H.C., et al., "Tamoxifen-associated Steatohepatitis C Report of Three Cases", Journal of Hepatology, 23, 95-97, (1995).

Podzimek, et al., "O/W Microemulsions", J. Dispersion Science and Technology, I, 341-359 (1980).

Popma, et al., "Factors Influencing Restenosis After Coronary Angioplasty", The Amer. J. of Med. vol. 88, pp. 1-16N-1-24N (1990).

Post et al., "The Relative Importance of Arterial Remodeling Compared With Intimal Hyerplasia in Lumen Renarrowing After Balloon ANgioplasty" Circulation 89, 2816-2821 (Jun. 1994).

Post, et al., "Restenosis Is Partly Due To Intimal Hyperplasia And Partly To Remodeling Of The Injured Arterial Wall," European Heart J., vol. 14, p. 201, Abstract P1164 (1993).

Post, et al., "Which Part Of The Angiographic Diameter Reduction After Balloon Dilation Is Due To Intimal Hyperplasia?", JACC, vol. 21, 36A, Abstract, 851-95 (1993).

Potter et al., "A mechanism hypothesis for DNA adduct formation following hepatic oxidative metabolism," Carcinogenesis, 15, 439-442 (1994).

Pouton, C.W., "Self-Emulsifying Drug Delivery Systems: Assessment of the Efficiency of Emulsification", International Journal of Pharmaceutics, 27, 335-348, (1985).

Powell et al., "Inhibitors of angiotensin-converting enzyme prevent myointimal proliferation after vascular injury," Science, 245:186-188 (1989).

Powell et al., "Suppression of the Vascular Response to Injury: The Role of Angiotensin-Converting Enzyme Inhibitors", JACC, 17, 137B-142B (1991).

Presentation at The Society of CV & Interventional Radiology's Twelfth Annual Course On "Diagnostic Angiography and Interventional Radiology." Includes: "The Current Status of Vascular Prostheses" by Julio Palmaz at 118-120 (Mar. 23 -26, 1987).

Program and abstracts of the Seventh International Conference on the Adjuvant Therapy of Cancer, held in Tuscon, Arizona on Mar. 10-13, 1993.

Pupita, G., et al., "Myocardial Ischemia Caused by Distal Coronary-Artery Constriction in Stable Angina Pectoris", The New England Journal of Medicine, 323, 514-520, (1990).

Rainsford, K.D., et al., "Concerning the Merits of Copper Aspirin as a Potential Anti-Inflammatory Drug", J. Pharm. Pharmac., 28, 83-86, (1976).

Rainsford, K.D., et al., "Gastric Mucus Effusion Elicited by Oral Copper Compounds: Potential Anti-Ulcer Activity", Experientia, 32, 1172-1173, (1976).

Raisz, L.G., "Estrogen and Bone: New Pieces to the Puzzle", Nature Medicine, 2, 1077-1078, (1996).

Raloff, "Tamoxifen Puts Cancer on Starvation Diet", Science News, 146, 292, (Nov. 5, 1994).

Rauterberg, et al., "Collagens in Atherosclerotic Vessel Wall Lesions," Current Topics in Pathology, vol. 87, pp. 163-192 (1993).

Ray, P., et al., "Repression of interleukin-6 gene expression by 17beta-estradiol: Inhibition of the DNA-binding activity of the transcription factors NF-IL6 and NF-6B by the estrogen receptor", FEBS Letters, 409, 79-85, (1997).

Razavi, M., "Unusual Forms of Coronary Artery Disease", Cleveland Clinic Consultations, 7, 25-46, (1975).

Recchia, F., et al., "Interferon-beta, Retinoids, and Tamoxifen in the Treatment of Metastatic Breast Cancer: A Phase II Study", Journal of Interferon and Cytokine Research, 15, 605-610, (1995).

Reckless, J., et al., "Tamoxifen Decreases Cholesterol Sevenfold and Abolishes Lipid Lesion Development in Apolipoprotein E Knockout Mice", Circulation, 95, 1542-1548, (1997).

Reid, et al., "Fragmentation of DNA in P388D$_1$ Macrophages Exposed to Oxidized Low-density Lipoprotein," FEBS Letters, vol. 332, No. 3, pp. 218-220 (1993).

Reilly et al., "Antiproliferative effects of heparin on vascular smooth muscle cells are reversed by epidermal growth factor," J. Cell Physiol., 131 :t 49-157 (1987).

Reilly, C.F., "Rat Vascular Smooth Muscle Cells Immortalized with SV40 Large T Antigen Possess Defined Smooth Muscle Cell Characteristics Including Growth Inhibition by Heparin", Journal of Cellular Physiology, 142, 342-351, (1990).

Reiner, Z., et al., "Antiestrogen Tamoxifen Reduces Lipoprotein(a)", Abstracts, The Second International Conference on Lipoprotein(a), New Orleans, LA, 124, (Nov. 12-14, 1992).

Reis, G.J., et al., "Randomized Trial of Fish Oil for Prevention of Restenosis After Coronary Angioplasty", The Lancet, 177-181, (1989).

Ribeiro, G., et al., "Adjuvant Tamoxifen for Male Breast Cancer (MBC)", Br. J. Cancer, 65, 252-254, (1992).

Rieckmann, P., et al., "Tumor Necrosis Factor-a Messenger RNA Expression in Patients with Relapsing-Remitting Multiple Sclerosis is Associated with Disease Activity", Ann. Neurol, 27, 82-88, (1996).

Riessen et al., "Prospects for Site-Specific Delivery of Pharmacologic and Molecular Therapies", J. Amer. Collage of Cardiol., 23, 1234-1244 (Apr. 1994).

Riessen et al., "Regional Differences in the Distribution of the Proteoglycans Biglycan and Decorin in the Extracellular Matrix of Atherosclerotic and Restenotic Human Coronary Ateries", Amer. J. Path 144, 962-974 (May 1994).

Roberts et al., "Type beta transforming growth factor: a bifunctional regulator of cellular growth," Proc. Natl. Acad. Sci., 82:119-123 (1985).

Robinson, J.R. (ed), "Sustained and Controlled Release Drug Delivery Systems," New York, Marcel Dekker (1978). Chapters 1-2, 4, and 7-9.

Roche Lexikon Medizin, Urban und Schwarzenberg, 1984, p. 69 "Antibiotika", and p. 515 "Fibrin".

Rompp, Chemie-Lexikon, 8$^{th}$ ed., 1987, p. 2633 "Mitosehemmer".

Ross, et al., Chronic Inflammation, PDGF, TGF, and Smooth Muscle Proliferation, Abstracts from the 20$^{th}$ Annual Meeting of the Keystone Symposia on Molecular Biology, Session on Molecular Mechanisms of Vascular Disease, J. Cell Biochem. S15C, Abstract No. G006, p. 96 (1991).

Ross, Russell, The Pathogenesis of Atherosclerosis: A Perspective for the 1990s, Nature, vol. 362, pp. 801-809 (1993).

Roubin, "Intracoronary Stenting of Canine Coronary Arteries After Percutaneous Coronary Angioplasty (PTCA)," Circulation Oct. 1986;74(Supp. II-458):1825 Abstract.

Rowinsky et al., "Taxol: Twenty years Later, the Story Unfolds," Journal of the National Cancer Institute, 1991, vol. 83 No. 24 pp. 1778-1781.

Rutqvist, L.E., et al., "Cardiac and Thromboembolic Morbidity Among Postmenopausal Women with Early-Stage Breast Cancer in a Randomized Trial of Adjuvant Tamoxifen", Journal of the National Cancer Institute, 85, 1398-1406, (1993).

Rutsch, et al., "Benestent-II Pilot Study: 6 months Follow Up of Phase 1" Abstract, Society of Cardiology, (1995).

Ruygrok and Serruys, "From Bench to Bedside, Intracoronary Stenting, From Concept to Custom," Circulation 1996; 94:882-890.

Ryan et al., "Transforming growth factor-beta-dependent events in vascular remodeling following arterial injury," J.. Vase. Res., 40:37-46 (2003).

Saarto, T., et al., "Antiatherogenic Effects of Adjuvant Antiestrogens: A Randomized Trial Comparing the Effects of Tamoxifen and Toremifene on Plasma Lipid Levels in Postmenopausal Women with Node-Positive Breast Cancer", Journal of Clinical Oncology, 14, 429-433, (Feb. 1996).

Sabatini et al., "RAFT1: a mammalian protein that binds to FK.BP12 in a rapamycin-dependent fashion and is homologous to yeast TORs", Cell, 78:35-43 (1994).

Sagitani, et al., "Microemulsion Systems with a Nonionic Cosurfant" J. Dispersion Science and Technology, 1 (2), 151-164 (1980).

Saito, H., et al., "Influence of Maternal Drug Metabolism on the Fetal Toxicity Induced by Acetylsalicylic Acid", The Journal of Toxicological Sciences, 7, 177-184, (1982).

Sanchez, et al., "Control of Contact activation on end-point immobilized heparin, The role of antithrombin and the specific antithrombin-binding sequence," *J. Of Biomedical Materials Research*, pp. 655-661 (1995).

Sanders, et al., "Controlled Release of a Luteinizing Hormone-Releasing Hormone Analogue from Poly(d,1-lactide-co-glycolide) Microspheres," Journal of Pharmaceutical Sciences, vol. 73, No. 9, pp. 1294-1297 (1984).

Sanderson et al., "Antibody-Coated Microspheres for Drug Delivery to Prevent Restenosis", Circulation, 90, I 508, Abstract No. 2734 (Oct. 1994).

Sargent, L.M., et al., "Induction of Hepatic Aneuploidy in Vivo by Tamoxifen, Toremifene and Idoxifene in Female Sprague-Dawley Rats", Carcinogenesis, 17, 1051-1056, (1996).

Schatz et al., "Balloon Expandable Intravascular Stents in Diseased Human Cadaver Coronary Arteries," Circulation Oct. 1987;70(4): Abstract 0102.

Schatz et al., "Balloon-expandable Intra-coronary Stents In The Adult Dog," Circulation Aug. 1987; 76(2):450-457.

Schatz, "A View of Vascular Stents", Circulation, 79 445-457 (1989).

Schatz, et al., "Balloon Expandable Intracoronary Stents In Dogs," Circulation Oct. 1986;74(Supp. II-458): 1824 Abstract.

Schatz, et al., "Clinical Experience with the Palmaz-Schatz Stent: Initial Results of A Multicenter Study," Circulation Jan. 1991;83(1): 148-161.

Schatz, R.A. Introduction to Intravascular Stents, Cardiology Clinics Aug. 1988;6(3):357-72.

Schlaak, J.F., et al., "Different Cytokine Profiles in the Synovial Fluid of Patients with Osteoarthritis, Rheumatoid Arthritis and Seronegative Spondylarthropathies", Clinical and Experimental Rheumatology, 14, 155-162, (1996).

Schlingemann, et al., Expression of the High Molecular Weight Melanoma-Associated Antigen by Pericytes During Angiogenesis in Tumors and in Healing Wounds, Amer. J. Pathology, vol. 136, No. 6, pp. 1393-1405 (1990).

Schmidt, E.B., et al., "Long-Term Supplementation with n-3 Fatty Acids, II: Effect on Neutrophil and Monocyte Chemotaxis", Scand. J. Clin. Lab. Invest., 52, 229-236, (1992).

Schneiderman, et al., "Increased Type I Plasminogen Activator Inhibitor Gene Expression in Atherosclerotic Human Arteries," PNAS (USA), vol. 89, pp. 6998-7002 (1992).

Schoenemanne, et al., "The Differential Diagnoses of Spontaneous Pneumothrax and Pulmonary Lymphangioleimyomatosis Clinical Picture Diagnoses and Theory.", Chiraq, 61, 301-303 (1990); reported in Biosis, 90, 432367 (1990), English abstract only.

Schulick et al.., "Overexpression of transforming growth factor beta1 in arterial endothelium causes hyperplasia, apoptosis, and cartilaginous metaplasia," PNAS 95:6983-6988 (1998).

Schwartz, C.J., et al., "The Pathogenesis of Atherosclerosis: An Overview", Clin. Cardiol., 14, I-1-I-16, (1991).

Schwartz, et al., "Maintenance of Integrity in Aortic Endothelium," Fed. Proc., vol. 39, No. 9, pp. 2618-2625 (1980).

Schwartz, et al., Restenosis After Balloon Angioplasty—A Practical Proliferative Model in Porcine Coronary Arteries, Circulation, vol. 82, No. 6, pp. 2190-2200 (1990).

Schwartz, et al., "The Restenosis Paradigm Revisited: An Alternative Proposal for Cellular Mechanisms," JACC, vol. 20, No. 5, pp. 1284-1293 (1992).

Schwartz, G.G., et al., "Pathophysiology of Chronic Stable Angina", In: Atherosclerosis and Coronary Artery Disease, V. Fuster, et al., (eds.), Lippencott-Raven Publishers, Philadelphia, pp. 1386-1400, (1996).

Sedlacek, S. "Estrogenic Properties of Tamoxifen on Serum Lipids in Postmenopausal Women with Breast Cancer (BCA)", Breast Cancer Research and Treatment, 14, Abstract No. 82, 153, (1989).

Sehgal et al., "Rapamycin (AY-22,989), a new antifungal antibiotic. II. Fermentation, isolation and characterization." J. Antibiot., 28:727-32 (1975).

Sehgal, "Sirolimus: its discovery, biological properties, and mechanism of action." Transplant. Proc., 35(3 Suppl):7S-148 (2003).

Serruys et al., "The new angiotensin converting enzyme inhibitor cilazapril does not prevent restenosis after coronary angioplasty: the results of the Mercator trial," JACC 19:258A, Abstract 783-2 (1992).

Serruys, et al., "A Comparison of Balloon-Expendable-Stent Implantation with Balloon Angioplasty in Patients with Coronary Artery Disease", The New England Journal of Medicine, 331, 489-495 (Aug. 1994).

Serruys, P.W., et al., "Heparin-Coated Palmaz-Schatz Stents in Human Coronary Arteries—Early Outcome of the Benestent-II Pilot Study", Circulation, 93, 412-422, (Feb. 1996).

Shanahan and Weissberg, "Smooth muscle cell heterogeneity: patterns of gene expression in vascular smooth muscle cells in vitro and in vivo," Arterioscler. Thromb. Vase. Biol., 18(2):333-338 (1998).

Shanahan, C.M., et al., "High Expression of Genes for Calcification-regulating Proteins in Human Atherosclerotic Plaques", Journal of Clinical Investigation, 93, 2393-2402, (Jun. 1994).

Shananhan, et al., "Isolation of Gene Markers of Differentiated and Proliferating Vascular Smooth Muscle Cells," Circulation Research, vol. 73, No. 1 (1993).

Shapiro, L.M., "Echocardographic Features of Impaired Ventricular Function in Diabetes Mellitus", British Heart Journal, 47, 439-444, (1982).

Shemon, et al., "Tamoxifen Decreases Lipoprotein(a) in Patients with Breast Cancer.", Metabolism, 43, 531-532, (May 1994).

Shewmon, et al., "Tamoxifen and Estrogen Lower Circulating Lipoprotein(a) Concentration in Healthy Postmenopausal Women", Arteriosclerosis and Thrombosis, 14, 1589-1593, (1994).

Shewmon, et al., "Tamoxifen Lowers Lp(a) in Males with Heart Disease," Supplement I Cir., vol. 86, No. 4, p. 1345 (1992).

Shimaoka, I., et al., "Purification of a Copper Binding Peptide from the Mushroom Grifola Frondosa and Its Effect on Copper Absorption", J. Nutr. Biochem., 4, 33-38, (1993).

Shoji, et al., "Enhancement of Anti-Inflammatory Effects of Biphenylylacetic Acid by its Incorporation into Lipid Microspheres," J. Pharm. Pharmacol. 38:118-121 (1985).

Shou et al., "Cardiac defects and altered ryanodine receptor function in mice lacking FK-BP 12," Nature, 391 (6666):489-92 (1998).

Siebenlist, U., et al., "Structure, Regulation and Function of NF-kB", Annu. Rev. Cell. Biol., 10, 405-455, (1994).

Sigwart, et al., "Intravascular Stents to Prevent Occlusion and Restenosis After Transluminal Angioplasty," N. Engl. J. Med., Mar. 19, 1987, vol. 316, No. 12, pp. 701-706.

Sigwart, U., Frank, G.I., "Bioabsorbable, Drug-Eluting, Intracoronary Stents: Design and Future Applications," Coroinary Stents. Springer-Verlag (1992).

Sigwart, Ulrich, "The Self Expanding Mesh Stent" Textbook of Interventional Cardiology, (Eric J. Topol, ed) 1990, Chapter 29, pp. 605-622.

Silber, S. "Drug-eluting stents: aktueller Stand", internet article on http://sigmund-silber.com/deutsch/varia/var-2003/03-09-5-Silber-Chemnitz.pdf of Aug. 6, 2003.

Simpson, J.B., et al., "Percutaneous Coronary Atherectomy", Circulation, 978, 61st Scientific Session, Abstract No. 326, p. II-82, (Oct. 1988).

Singh, et al., "Phylogenetic Analysis of Platelet-derived Growth Factor by Radio-Receptor Assay," The Journal of Cell Biology, vol. 95, pp. 667-671 (1982).

Sismondi, et al., "Metabolic Effects of Tamoxifen in Postmenopause.", Anticancer Res., 14, 2237-2244, (1994).

Snow, et al., "Heparin Modulates the Composition of the Extracellular Matrix Domain Surrounding Arterial Smooth Muscle Cells," American J. of Pathology, vol. 137, No. 2 (1990).

Soderberg, L.S., et al., "Copper (II) (3,5-Diisopropylsalicylate) sub2 Accelerates Recovery of B and T Cell Reactivity Following Irradiation", Scand J. Immunol., 26, 495-502, (1987).

Soderberg, L.S., et al., "Copper (II) sub2(3, 5-diisopropylsalicylate) sub4 Stimulates Hemopoiesis in Normal and Irradiated Mice", Exp. Hematol., 18, 577-580, (1988).

Soderberg, L.S., et al., "Postirradiation Treatment with Copper (II) sub2 (3,5-diisopropylsalicylate) sub4 Enhances Radiation Recovery and Hemopoietic Regeneration", Exp. Hematol., 18, 801-805, (1990).

Soderberg, L.S., et al., "Radiation Recovery Agents", DN & P, 3, 600-605, (1990).

Sollott, S.J., et al., "Taxol Inhibits Neointimal Smooth Muscle Cell Accumulation after Angioplasty in the Rat", The Journal of Clinical Investigation, 95, 1869-1876, (Apr. 1995).

Song "Dexamethasone-nanoparticles for intra-arterial localization in restenosis in rats," Prceed. Intern .Symp. Control. Rel. Mater., 22, 444-445 (1995).

Song, J., et al., "Tamoxifen (Estrogen Antagonist) Inhibits Voltage-Gated Calcium Current and Contractility in Vascular Smooth Muscle from Rats", The Journal of Pharmacology and Experimental Therapeutics, 227, 1444-1453, (1996).

Sorenson, J.R., "Copper Complexes Offer a Physiological Approach to Treatment of Chronic Disease", Progress in Medicinal Chemistry, 26, 437-568, (1989).

Sorenson, J.R., "Essential Metalloelement Metabolism and Radiation Protection and Recovery", Radiation Research, 132, 19-29, (1992).

Sorenson, J.R., "Pharmacological Activities of Copper Compounds", In: Handbook of Metal-Ligand Interactions in Biological Fluids—Bioinorganic Medicince, vol. 2, Berton, G., (ed.), Marcel Dekker, Inc., New York, 1128-1139, (1995).

Sorenson, J.R., "Radiation Protection and Radiation Recovery with Essential Metalloelement Chelate", P.S.E.B.M., 210, 191-204, (1995).

Sorenson, J.R., "The Ulcerogenic Potential of Copper Aspirinate Seems to be More Imaginary than Real", Journal of Pharmaceutical Sciences, 73, Open Forum, 1875-1878, (1984).

Sorenson, J.R., et al., "Antieoplastic Activities of Some Copper Salicylates", In: Trace Substances in Environmental Health, vol. XVI, Hemphill, D.D., (ed.), University of Missouri, Columbia, 362-369, (1982).

Sorenson, J.R., et al., "Bis (3, 5-diisopropylsalicylato) copper (II), a Potent Radioprotectant with Superoxide Dismutase Mimetic Activity", J. Med. Chem., 27, 1747-1749, (1984).

Sorenson, J.R., et al., "Copper Complexes as 'Radiation Recovery' Agents", Chemistry in Britain, 25, 169-171, (1989).

Sorenson, J.R., et al., "Copper-, Iron-, Manganese- and zinc-3, 5-diisopropylsalicylate Complexes Increase Survival of Gamma-Irradiated Mice", Eur. J. Med. Chem., 28, 221-229, (1993).

Sousa et al., "Sustained suppression of neointimal proliferation by sirolimus-eluting stents: one-year angiographic and intravascular ultrasound follow-up," Circulation, 104:2007-i 1 (2001) (CYP228071-228075).

Sousa et al., "Two-year angiographic and intravascular ultrasound follow-up after implantation of sirolimus-eluting stents in human coronary arteries," Circulation. 107(3):381-3 (2003) (BSX 024170-024172).

Sousa, J.E. et al., "New Frontiers in Cardiology Drug-Eluting Stens: Part I", Circulation, 2003, 107:2274-2279.

Southgate and Newby, "Serum-induced proliferation of rabbit aortic smooth muscle cells from the contractile state is inhibited by 8-Br-cAMP but not 8-Br-cGMP," Atherosclerosis, 82:113-123 (1990).

Speir et al., "Potential Role of Human Cytomegalorvirus and p53 Interaction in Coronary Restenosis", Science, 265, 391-394 (1994).

Srivastava, K.C., "Effects of Dietary Fatty Acids, Prostaglandins and Related Compounds on the Role of Platelets in Thrombosis", Biochem. Exp. Biol., 16, 317-338, (1980).

Steele, P.M. et al., "Balloon Angioplasty—Nature History of the Pathophysiological Response to Injury in a Pig Model", Circulation Research, 57 105-112 (1985).

Stevenson, F., et al., "Idiotypic DNA Vaccines against B-cell Lymphoma", Immunological Reviews, 145, 221-228, (1995).

Stork, G., et al., "Total Synthesis of Cytochalasin B", Journal of the American Chemical Society, 100, 7775-7777, (1978).

Stouffer, et al., "TGF beta Has a Biphasic, Concentration Dependant Effect on EFG and PDGR-BB Induced Smooth Muscle Cell Proliferation, Inflammation, Growth Regulatory Molecules and Atherosclerosis.", J. Cellular Biochem, Supplement 18A, Abstract No. A321, 288, (1994).

Strepetti, A.V., et al., "Formation of Myointimal Hyperplasia and Cytokine Production in Experimental Vein Grafts", Surgery, 123(4), 461-469, (1998).

Streuli, et al., "Extracellular Matrix Regulators Expression of the TGF-β1 Gene," The J. of Cell Biol. vol. 120, No. 1, pp. 253-260 (1993).

Suckling, "Atherosclerosis Patents: Clues to the Next Drug Generation", Bio/Tech, 12 1379-1380 (Dec. 1994).

Suckling, Keith E., "Emerging Strategies for the Treatment of Atherosclerosis as Seen from the Patent Literature," Biochem. Society Transactions, vol. 21, pp. 660-662 (1993).

Sudo, K., et al., "Antiestrogen-Binding Sites Distinct from the Estrogen Receptor: Subcellular Localization, Ligand Specificity, and Distribution in Tissues of the Rat", Endocrinology, 112, 425-434, (1983).

Swain, "Blazing new paths for product introductions," Medical Device & Diagnostic Industry, Sep. 2003, p. 68-81.

Szekanecz, Z., et al., "Increased Synovial Expression of Transforming Growth Factor (TGF) -B Receptor Endoglin and TGF- B1 in Rheumatoid Arthritis: Possible Interaction in the Pathogenesis of the Disease", Clinical Immunology and Immunopathology, 76, 187-194, (Aug. 1995).

Tabas et al., "the Actin Cytoskeleton in Important for the Stimulation of Cholesterol Esterification by Atherogenic Lipoprotiens in Macrophages" J. Biol. Chem., 269, 22547-22556 (Sep. 9, 1994).

Takashima, K. et al., "The Hypocholesterolemic Action of TA-7552 and its Effects on Cholesterol Metabolism in the Rat", Atherosclerosis, 107, 247-257, (1994).

Tanaka et al., "1alpha 25 (OH) 303 Exerts Cytostatic effects on Murine Osteosarcoma Cells and Enhance Cytocidal Effects on Anticancer Drugs" Clinical Orthopaedics and related Research No. 247 1989 pp. 290-296.

Tanaka et al., "Prominent Inhibitory Effects of Tranilast on Migration and Proliferation of and Collagen Synthesis by Vascular Smooth Muscle Cells" Atherosclerosis, 107, 179-185 (1994).

Tanenbaum, S.W., "Microbiological, Preparative and Analytical Aspects of Cytochalasin Production", In: Cytochalasins—Biochemical and Cell Biological Aspects, Tanenbaum, S.W., (ed.), Elsevier/North-Holland Biomedical Press, 2-14, (1978).

Tang et al., "Regression of collagen-induced arthritis with taxol, a microtubule stabilizer". Arthritis and Rheumatism, 36 (9) Suppl.:S45, 1993.

Tawashi, R., "The dissolution rates of crystalline drugs", J. Mond. Pharm, 4,11,1968, pp. 371-379.

Teirstein (ed.), "Coronary Stents: pros and cons," Coronary Artery Disease, 5:561-600 (1994).

Tessari et al., "Antiproliferative activity of unfractioned heparin on a human smooth muscle cell line, Pharmacol." Res., 21:145-6 (1989).
Testart, J., et al., "The Action of Anti-Inflammatory Drugs to the Fertility of Female Rats with Intrauterine Contraceptive Devices", J. Reprod. Fert., 63, 257-261, (1981).
Thompson, J.T., et al., "Comparison of Recombinant Transforming Growth Factor-beta -2 and Placebo as an adjunctive Agent for Macular Hole Surgery", Ophthalmology, 15(4), 700-706, (1998).
Thompson, N.L., et al., "Expression of Transforming Growth Factor-B1 in Specific Cells and Tissue of Adult and Neonatal Mice", Journal of Cell Biology, 108, 661-669, (1989).
Tice, et al., "Biodegradable controlled-release parental systems" Pharmaceutical Technology, 26-35 (1984).
Tong et al., Non-Thrombogenic Hemofiltration System for Acute renal failure Treatment: ASAIO Trans. 38: M702-M706 (1992).
Toomasian et al., "Evaluation of Duraflo II Herparin Coating in Prolonged Extracorporeal Membrane Oxygenation", ASAIO Trans 34: 410-14 (1988).
Topol, E. et al., "Frontiers in Interventional Cardiology" Circulation, 1998, 98:1802-1820.
Topol, Eric J., The Restenosis "Antitheory", Mayo Clinic Proc. vol. 68, pp. 88-90 (1993).
Treasure, C.B., et al., "Hypertension and Left Ventricular Hypertrophy Are Associated With Impaired Endothelium-Mediated Relaxation in Human Coronary Resistance Vessels", Circulation, 87, 86-93, (1993).
Treiber, A., et al., "Chemical and Biological Oxidation of Thiophene: Preparation and Complete Characterization of Tiophene S-Oxide Dimers and Evidence for Thiophene S-Oxide as an Intermediate in Thiophene Metabolism in vivo and In Vitro", J. Am. Chem. Soc., 119, 1565-1571, (1997).
Tucker et al., "Growth inhibitor from BSC-1 cells closely related to platelet type beta transforming growth factor," Science, 226:705-707 (1984).
Ulman, et al., "Drug Permeability of Modified Silicone Polymers," Journal of Controlled Release 1989; 10:273-281.
Ulman, K.L. et al., "Drug Permeability of Modified Silicone Polymers", J. Controlled Release, 10:251-260 (1989).
Van Der Giessen, et al., "Coronary Stenting With Polymer-Coated And Uncoated Self-Expanding Endoprosthesis In Pigs" Coron. Art. Disease 1992; 3:631-40.
Van Der Giessen, et al., "Self-expandable Mesh Stents: an Experimental Study Comparing Polymer Coated and Uncoated Wallstent Stents in the Coronary Circulation of Pigs" Circulation 82:III-542 (1990).
Van Sickle, W.A., et al., "An Alternative Mechanism for the Inhibition of Cholesterol Biosyntesis in HepG2 Cells by N- [(1,5,9) - Trimethyldecyl] -4alpha, 10-dimethyl 8-aza-trans-decal-3beta-ol (MDL 28, 815)", The Journal of Pharmacology and Experimental Therapeutics, 267, 243-1249, (1993).
Vanhoutte, P.M., "Hypercholesterolemia, Atherosclerosis and Release Of Endothelium-Derived Relaxing Factor By Aggregating Platelets," European Heart J. vol. 12, Supplement E. pp. 25-32 (1991).
Vargas, et al., "Oestradiol Inhibits Smooth Muscle Cell Proliferation of Pig Coronary Artery," Br. J. Pharmacol., vol. 109, pp. 612-617 (1993).
Vawter, M.P., et al., "TGF B1 and TGF B2 Concentrations are Elevated in Parkinson's Disease in Ventricular Cerebrospinal Fluid", Experimental Neurology, 141, 313-332, (1996).
Vidensek N., et al., "Taxol Content in Bark, Wood, Root, Leaf, Twig, and Seedling from Several Taxus Species", Journal of Natural Products, 53, 1609-1610, (Nov./Dec. 1990).
Vijayagopal, et al., "Human Monocyte-Derived Macrophages Bind Low-Density-Lipoprotein-Proteoglycan Complexes by a Receptor Different from the Low-Density-Lipoprotein Receptor," Biochem. J., vol. 289, pp. 837-844 (1993) (GB).
Vijayagopal, et al., "Lipoprotein-Proteoglycan Complexes Induce Continued Cholesteryl Ester Accumulation in Foam Cells from Rabbit Atherosclerotic Lesions," J. Clin. Invest. vol. 91, pp. 1011-1018 (1993).
Voigt, R., Lehrbuch der pharmazeutischen Technologie, 5$^{th}$. edition VEB Verlag Volk und Gesundheit Berlin, 1984, p. 689.

Voisard, et al., "The In-Vitro Effect of Antineoplastic Agents on Proliferative Activity and Cytoskeletal Components of Plaque-derived Smooth-muscle Cells from Human Coronary Arteries," Coronary Artery Disease, 4:935-942 (1993).
Voisard, R., et al., "Search for new strategies for prevention of restenosis after angioplasty: the effect of cytostatic drugs on cell migration of re-stenosing human plaques cells in vitro". Vasa Suppl. 1992; 35: 132-3 [Article in German].
Von Schacky, C., et al., "Long-Term Effects of Dietary Marine omega-3 Fatty Acids upon Plasma and Cellular Lipids, Platelet Function, and Eicosanoid Formation in Humans", J. Clin. Invest., 76, 1626-1631, (1985).
Vrudhula, V.M., et al., "Selective Synthetic Transformations with Roridin A", Abstracts, 199$^{th}$ American Chemical Society National Meeting, Abstract No. 50, Boston, MA, (Apr. 22-27, 1990).
Wakefield, et al., "Latent Transforming Growth Factor β from Human Platelets: A High Molecular Weight Complex Containing Precursor Sequences," The Journal of Biological Chemistry, vol. 263, No. 16, pp. 7646-7654 (1988).
Wakefield, et al., "Recombinant Latent Transforming Growth Factor I Has a Longer Plasma Half-Life in Rats than Active Transforming Growth Factor, I, and a Different Tissue Distribution," The Journal of Clinical Investigation, Inc., vol. 86, pp. 1976-1984 (1990).
Waksman, R., et al., "Intracoronary Radiation Before Stent Implantation Inhibits Neointima Formation in Stented Porcine Coronary Arteries", Circulation, 92, 1383-1386, (1995).
Wallace, et al., "Tracheobronchial Tree: Expandable Metallic Stents Used in Experimental and Clinical Applications," Radiology Feb. 1986;158(2):309-12.
Wallace, J.M., et al., "Dietary Fish Oil Supplementation Alter Leukocyte Function and Cytokine Production in Healthy Women", Arteriosclerosis, Thrombosis and Vascular Biology, 15, 185-189, (1995).
Waller et al., "Crackers, Breakers, Stretchers, Drillers, Scrappers, Shavers, Burners, Welders and Melters: The Future Treatment of Atherosclerotic Coronary Artery Disease?" A Clinical-Morphologic Assessment, JACC 13:969-87 (1989).
Waller et al., "Differential effects of modem immunosuppressive agents on the development of intimal hyperplasia," Transpl. Int. 17:9-14 (2004).
Waller et al., "Mycophenolate mofetil inhibits intimal hyperplasia and attenuates the expression of genes favouring smooth muscle cell proliferation and migration," Transplant Proc. 37(1): 164-6 (2005).
Waller, B.F. X.L., et al., "Atherosclerotic and Nonatherosclerotic Coronary Artery Factors in Acute Myocardial Infarction", In: Acute Myocardial Infarction, Pepine, C.J., (ed.), F.A. Davis Company, Philadelphia, 29-104, (1989).
Walternberger, "Modulation of growth factor action: implications for the treatment of cardiovascular diseases," Circulation, 96:4083-4094 (1997).
Wang, X.L., et al., "Circulating Transforming Growth Factor Beta1 and Coronary Artery Disease", Cardiovascular Research, 34, 404-410, (1997).
Ward et al., "Tranilast prevents activation of transforming growth factor-beta system, leukocyte accumulation, and neointimal growth in porcine coronary arteries after stenting," Arterioscler. Thromb. Vasc. Biol. 22:940-948 (2002).
Watson, et al., "TGF-B1 and 25-Hydroxcholesterol Stimulate Osteoblast-Like Vascular Cells to Calcify", J. Clin. Invest., 93, 2106-2113, (May 1994).
Wei, C.M. et al., "Binding of Trichodermin to Mammalian Ribosomes and Its Inhibition by Other 12, 13-Epoxytrichotheces", Molecular & Cellular Biochemistry, 3, 215-219, (May 30, 1974).
Weissberg, et al., "Approaches to the development of selective inhibitors of vascular smooth muscle cell proliferation," Cardiovascular Res., vol. 27, pp. 1191-1198 (1993).
Weissberg, et al., "The Endothelin Peptides ET-1, ET-2, ET-3 and Sarafotoxin S6b are Comitogenic with Platelet-Derived Growth Factor for Vascular Smooth Muscle Cells," Atherosclerosis, vol. 85, pp. 257-262 (1990).
Weissberg, et al., Effects of TGFB on Vascular Smooth Muscle Cell Growth, Growth Factors and the Cardiovascular System, (Cummins, P. ed), Kluwer Academic Publishers, p. 189-205 (1993).

Weissberg, P.L., et al., "Is Vascular Smooth Muscle Cell Proliferation Beneficial?", Lancet, 347, 305-307, (Feb. 3, 1996).
West, G.B., "Comments on 'The Ulcerogenic Potential of Copper Aspirinate Seems to be More Imaginary than Real'", Journal of Pharmaceutical Sciences, 74, Open Forum, 700, (1985).
West, G.B., "Testing for Drugs Inhibiting the Formation of Gastric Ulcers", Journal of Pharmacological Methods, 8, 33-37, (1982).
Wickremesinhe, E.R., et al., "Taxus Callus Cultures: Initiation, Growth, Optimization, Characterization and Taxol Production", Plan Cell, Tissue and Organ Culture, 35, 181-193, (1993).
Wickremesinhe, E.R., et al., "Taxus Cell Suspension Cultures: Optimizing Growth and Production of Taxol", J. Plant Physiol., 144, 183-188, (1994).
Wight, et al., "Proteoglycans Structure and Function," Cell Biol. of Extracellular Matrix, Second Edition, edited by Elizabeth D. Hay, Plenum Press, New York Chapter 2, pp. 45-78 (1991).
Wight, et al., "The Role of Proteoglycans in Cell Adhesion, Migration and Proliferation," Current Opinion in Cell Biol. vol. 4, pp. 793-801 (1992).
Wight, Thomas N., "Cell Biology of Arterial Proteoglycans," Arteriosclerosis, vol. 9, No. 1., pp. 1-20 (1989).
Wilensky, et al., "Direct Intraarterial Wall Injection of Microparticles via a Catheter: A Potential Drug Delivery Strategy Following Angioplasty," American Heart Journal, vol. 122, No. 4, pp. 1136-1140 (1991).
Wilensky, et al., "Regional and Arterial Localization of Radioactive Microparticles after Local Delivery by Unsupported Porous Balloon Catheters", American Heart Jounal, 129, 852-859 (May 1995).
Wilensky, R.L., et al., "A Prospective, Randomized, Double-Blind, Dose-Escalation Study Evaluating the Safety and Tolerability of Cytochalasin B to Reduce Vascular Remodeling Following Percutaneous Transluminal Coronary Angioplasty", Abstract, 46$^{th}$ Annual Scientific Session of the American College of Cardiology, 1 p., (1997).
Williams, J.K., et al., "The Estrogen Receptor Agonist/Antagonist Tamoxifen Inhibits Progression of Coronary Artery Atherosclerosis in Monkeys", Circulation, 92, Nov. 1995 AHA Meeting, (Oct. 15, 1995).
Willson, T.M., et al., "Dissection of the Molecular Mechanism of Action of GW5638, a Novel Estrogen Receptor Ligand, Provides Insights into the Role of Estrogen Receptor in Bone", Endocrinology, 138(9), (Sep. 1997).
Winokur et al., "Expression of transforming growth factors β 1, 2, and 3 following vascular injury," J. Cell Biochem., Suppl. 15C:G414 (Abstr.) (1991).
Winslow, R., "Going for the Flow", The Wall Street Journal, (Oct. 23, 1995).
Winternitz, C.I. et al., "Development of a Polymetric Surgical Paste Formulation for Taxol", Pharmaceutical Research, 13 368-375 (1996).
Wiseman, H., "Tamoxifen as an Antioxidant and Cardioprotectant", Biochem. Soc. Symp., 61, 209-219, (1995).
Wiseman, L.R., et al., "Toremifene—A Review of its Pharmacological Properties and Clinical Efficacy in the Management of Advanced Breast Cancer", Drugs, 54, 141-160, (Jul. 1997).
Witherup, K.M., et al., "Taxus Spp. Needles Contain Amounts of Taxol Comparable to the Bark of Taxus brevifolia: Analysis and Isolation", Journal of Natural Products, 53, 1249-1255, (Sep./Oct. 1990).
Wolf, Y.G., et al., "Antibodies Against Transforming Growth Factor Beta1 Suppress Intimal Hyperplasia in a Rat Model", J. Clin. Invest., 93, 1172-1178, (Mar. 1994).
Wolinsky, et al., Use of a Perforated Balloon Catheter to Deliver Concentrated Heparin Into the Wall of the Normal Canine Artery, JACC, vol. 15, No. 2, pp. 475-481 (1990).
Wrana, et al., "Mechanism of Activation of the TGF-B Receptor", Nature, 370 341-347, (Aug. 4, 1994).
Wright et al., "Cytoclasin Inhibition of Slow Tension Increase in Rat Aortic Rings", Am. J. Physion., 267 H1437- H1446 (1994).
Wright et al., "Percutaneous Endovascular Stents: An Experimental Study," Radiology Nov. 1984;153(P):206 Abs 593.
Wright et al., "Percutaneous Endovascular Stents: An Experimental Evaluation," Radiology 1985;1:69-72.

Wu et al., "Comparative immunoregulatory effects of rapamycin, FK 506 and cyclosporine on mitogen-induced cylokine production and lymphoproliferation," Transplant. Porc., 23:238-240 (1991).
Wu et al., "The inhibitory mechanism of YC-1, a benzyl indazole, on smooth muscel cell proliferation: an in vitro and in vivo study," J. Pharmacol. Sci. 94:252-60 (2004).
Wu, et al., "Silicone-covered Seft-expanding Metallic Stents for the Palliation of Malignant Esophageal Obstruction and Esophagorespiratory Fistulas: Experience in 32 Patients and a Review of the Literature," Gastrointest. Endosc. 1994; 40:22-33.
Yamamoto et al., "Ribozyme oligonucleotides against transforming growth facotr-beta inhibited neointimal formation after vascular injury in rat model: potential application of ribozyme strategy to treat cardiovascular disease," Circulation, 102(11):1308-14 (2000).
Yang, N., et al., "Developing Particle-mediated Gene-transfer Technology for Research Into Gene Therapy of Cancer", Molecular Medicine Today, 476-481, (1996).
Yang, N.N., et al., "Estrogen Receptor: One Transcription Factor, Two Genomic Pathways", Calcified Tissue Intl., 54, 342, (1994).
Yang, N.N., et al., "Identification of an Estrogen Response Element Activated by Metabolites of 17Beta-Estradiol and Raloxifene", Science, 273, 1222-1225, (Oct. 30, 1996).
Young H., et al., "Pharmacokinetics and Biodistribution of Radiolabelled Idoxifene: Prospects for the Use of PET in the Evaluation of a Novel Antioestrogen for Cancer Therapy", Nucl. Med. Biol., 22, 405-411, (May 1995).
Zhang, L. et al., "MCF-7 breast carcinoma cells overexpressing FGF-1 form vascularized, metastatic tumors in ovariectomized and tamoxifen-treated nude mice", Oncogen, 15, 2093-2108, (1997).
Zohlnhofer et al., "Rapamycin effects transcriptional programs in smooth muscle cells controlling proliferative and inflammatory properties," Mol. Pharmacol. 65:880-889 (2004).
Zuckerman, et al., "Cytokine Regulation of Macrophage apo E Secretion: Opposing Effects of GM-CSF and TGF-β," Atherosclerosis, vol. 96, pp. 203-214 (1992).
Zuckerman, et al., "Exogenous Glucocorticoids Increase Macrophage Secretion of E by Cholesterol-Independent Pathways," Atherosclerosis, vol. 103, pp. 43-54 (1993).
Baringa, "Gene Therapy for Clogged Arteries Passes Test in Pigs", Science, 265, 738 (Aug. 5, 1994).
"Coronary Artery Disease: Restenosis and Reocclusion After Surgical and Nonsurgical Interventions, Part 1", Durg and Market Development, 5, 121-129 (Sep. 26, 1994).
DiMario, "Is the Mechanism of Restenosis Device-Independent? Serial Assessment with Intracoronary Ultrasound", Circulation, 90, I-24, Abstract 115 (Oct. 1994).
Hanson, S., "Device Thrombosis and Thromboembolism," Cardiovasc Pathol. 2(3) (Suppl.): 157S-165S (Jul.-Sep. 1993).
Leroux, et al., "New Approach for the Preparation of Nanoparticles by an Emulsification-Diffusion Method", Eur. J. Pharm. Biopharm, 41, 14-18, (1995).
Merck Index, Eleventh Edition 2796, Cytochalasins, p. 438 (1989).
Polysciences Inc., TDMAC-Heparin Coatings, Nov. 1988, Data Sheet #172.
Answering Memorandum In Opposition To Plaintiffs' Motion For A Preliminary Injunction, Civil Action No. 03-283 Dated Apr. 3, 2003, U.S. District Court for the District of Delaware.
Appendix To Answering Memorandum In Opposition To Plaintiffs' Motion For A Preliminary Injunction, vol. 1, Civil Action No. 03-283 Dated Apr. 3, 2003, U.S. District Court for the District of Delaware.
Appendix To Answering Memorandum In Opposition To Plaintiffs' Motion For A Preliminary Injunction, vol. 2, Civil Action No. 03-283 Dated Apr. 3, 2003, U.S. District Court for the District of Delaware.
Complaint, Civil Action No. 03-283, Filed Mar. 13, 2003, U.S. District Court for the District of Delaware.
Declaration Of Brian G. Firth, Civil Action No. 03-283 SLR, Dated Mar. 31, 2003, U.S. District Court for the District of Delaware.
Declaration Of Dr. Jeffrey W. Moses, M.D., Civil Action No. 03-283 SLR, Dated Mar. 31, 2003, U.S. District Court for the District of Delaware.
Declaration Of Dr. Martin B. Leon, M.D., Civil Action No. 03-283 SLR, Dated Mar. 31, 2003, U.S. District Court for the District of Delaware.

Declaration Of Dr. Paul S. Teirstein, M.D., F.A.C.C., Civil Action No. 03-283 SLR, Dated Mar. 28, 2003, U.S. District Court for the District of Delaware.

Declaration Of Dr. Peter Fitzgerald, M.D., Ph.D., Civil Action No. 03-283 SLR, Dated Mar. 31, 2003, U.S. District Court for the District of Delaware.

Declaration Of Dr. Richard E. Kuntz, M.D. M.Sc., Civil Action No. 03-283 SLR, Dated Mar. 21, 2003, U.S. District Court for the District of Delaware.

Declaration Of Eric Simso, Civil Action No. 03-283, Dated Mar. 20, 2003, U.S. District Court for the District of Delaware.

Declaration Of Jermone Segal, M.D., Civil Action No. 03-283 Dated Mar. 20, 2003, U.S. District Court for the District of Delaware.

Declaration Of Kinam Park, Ph.D., Civil Action No. 03-283 Dated Mar. 20, 2003, U.S. District Court for the District of Delaware.

Defendants' Answer, Counterclaim And Demand For Jury Trial, Civil Action No. 03-283, Filed Apr. 7, 2003, U.S. District Court for the District of Delaware.

Opening Expert Report Of Robson F. Storey, Ph.D., Civil Action No. 03-283 SLR, Dated May 23, 2003, U.S. District Court for the District of Delaware.

Opening Expert Report Of Stephen R. Hanson, Ph.D., Civil Action No. 03-283 SLR, Dated May 23, 2003, U.S. District Court for the District of Delaware.

Plaintiffs' Opening Brief In Support Of Their Motion For Preliminary Injunction, Civil Action No. 03-283 Filed Mar. 20, 2003, U.S. District Court for the District of Delaware.

Plaintiffs' Reply Brief In Support Of their Motion For Preliminary Injunction, Civil Action No. 03-283 SLR, Dated Apr. 10, 2003, U.S. District Court for the District of Delaware.

Plaintiffs' Reply To Defendant's Counterclaim, Civil Action No. 03-283 Filed Apr. 21, 2003, U.S. District Court for the District of Delaware.

Preliminary Injunction Hearing Transcript, vol. A, Civil Action No. 03-27 (SLR), Dated Jul. 21, 2003, U.S. District Court for the District of Delaware.

Preliminary Injunction Hearing Transcript, vol. B, Civil Action No. 03-27 (SLR), Dated Jul. 22, 2003, U.S. District Court for the District of Delaware.

Preliminary Injunction Hearing Transcript, vol. C, Civil Action No. 03-27 (SLR), Dated Jul. 23, 2003, U.S. District Court for the District of Delaware.

Rebuttal Expert Report Of Kiman Park. Ph.D., Civil Action No. 03-283 SLR, Dated Jun. 2, 2003, U.S. District Court for the District of Delaware.

Second Declaration Of Jerome Segal, M.D., Civil Action No. 03-283 SLR, Dated Apr. 10, 2003, U.S. District Court for the District of Delaware.

Second Declaration Of Kinam Park, Ph.D., Civil Action No. 03-283 SLR, Dated Apr. 10, 2003, U.S. District Court for the District of Delaware.

* cited by examiner

STENT DEVICE AND METHOD

This application is a continuation of U.S. application Ser. No. 10/443,266, filed May 22, 2003, now U.S. Pat. No. 7,011,680, issued on Mar. 14, 2006, which is a continuation of U.S. application Ser. No. 09/847,626, filed May 2, 2001, now U.S. Pat. No. 6,613,083, issued on Sep. 2, 2003, the entire disclosure of each of which is incorporated herein by reference in its entirety.

FIELD OF THE INVENTION

The invention relates generally to stents and more particularly to a drug delivery endovascular stent which delivers a specific immunosuppressant drug to the stent treatment site.

BACKGROUND OF THE INVENTION

Stents are a widely used adjunct to coronary artery interventions. After an angioplasty or other intervention, a stent may be introduced to the treatment site to support the wall of the artery.

The principle problem with stent usage is a re-closure process called restenosis. The problem of restenosis is widely recognized. It appears from research that the mechanisms for restenosis after a balloon procedure differs in detail from the healing processes associated with stent placement.

The biological reactions associated with the use stents causes a cascade of cellular growth and proliferation. The mechanical action of the stent against the artery wall (spring back) and the introduction of the foreign substance into the body results in an inflammatory response which gives rise to signaling molecules called cytokines which mediate a variety of biologic processes. Although the magnitude and course of the inflammatory response varies widely among patients, the body isolates the foreign material of the stent by encapsulating it with cell growth. Consequently a pseudo intima will be produced on the surface of the stent. In general the propagation of a smooth muscle tissue pseudo intima is desirable, however in some patients the proliferation of smooth muscle cells and their conversion to secretory muscle cells results in re-closure of the vessel within a short period of time. Although this is a normal response to the insertion of a foreign body, given the location of the stent it results in severe clinical problems. Other short term complications exist as well including acute thrombosis. The delivery of anti platelet drugs and other thrombolytic drugs have been proposed to treat this near term type of reclosure.

Several efforts have been made to prevent or delay the longer term restenosis process. One approach has been to implant radioactive stents where the local emission of beta radiation inhibits hyperplasia. Although intra-coronary radiation is effective at preventing restenosis this grossly interferes with the healing process previously described and can lead to secondary complications such as edge restenosis and late thrombosis. One example of this stent technology is known from U.S. Pat. No. 5,871,437 to Alt. This reference teaches the use of multiple coating on the stent substrate. One coating carries a beta emitter while other coatings deliver a anticoagulation drug.

Another approach to the treatment of acute thrombosis in stent treatments is discussed in U.S. Pat. No. 5,788,979 to Alt et al. The stent according to this invention uses a biodegradable coating to release a controlled amount of a therapeutic agent such as an a anti-coagulant, anti-thrombogenic, or anti-stenotic drug. The biodegradable coating provides a local release of drug which improves the bio-compatibility of the stent and reduces inflammation and the hyperplasia processes. The objective or these different methods is to interfere with and control the proliferation of the smooth muscle cells.

Although the various coated stents improve the restenosis rates for some patients, a fully bio-compatible stent remains an elusive problem as the factors of local thrombus formation, vessel injury and inflammation interact in complex and individually variable ways. For these reasons re-occlusion and restenosis problems are difficult to manage in a clinical setting. Restenosis remains a significant risk for patients.

SUMMARY

In contrast to the prior art, the stent of the present invention delivers an effective dose of the immunosuppressant drug tacrolimus to the stent treatment site. The tacrolimus is delivered at a rate and in a concentration that both encourages proliferation of smooth muscle cells and limits conversion of such cells to the secretory type muscle cells. This method and approach differs from the prior art cytostatic techniques where Taxol and related drugs are used in an overall strategy to interfere with and delay the healing response.

In accord with the method and device of the of the present invention a stent delivers tacrolimus to the cells proliferating on the surface of the stent. The stent forms a primary structure and the coating is a secondary process. In general it is preferred to use a polymer coat but surface modification of the stent itself to create a drug delivery surface is possible though not preferred.

The preferred device delivers drug by elution from a polymer matrix applied as a coating to the stent. The polymer matrix may be permanent and non biodegradable or it may be biodegradable. An example of a suitable biodegradable material is polylactic acid (PLA). Examples of more permanent matrix materials includes; polyethylene; vinyl acetate and medical polyurethanes and silicone rubber. Other biodegradable and non-biodegradable materials are contemplated within the scope of the inventions well. The primary requirement is the formation of a biocompatible matrix to allow elution of the tacrolimus.

The localized and selective delivery of the tacrolimus and tacrolimus containing compounds encourages endothelization of the stent with smooth muscle cells and other endothelial cells and discourages the proliferation and conversion of such cells to secretory smooth muscle cell types.

The beneficial effect of tacrolimus and its analogues is unknown in this context and the drug is not indicated for or labeled for use in cardiovascular interventions.

Although arterial endovascular and specifically coronary interventions are an important application for this invention it should be recognized that other biomedical devices and device locations, sizes and drug concentrations are contemplated within the scope of the invention. It must also be recognized that additional features and structures may be added to the invention without departing from the scope of the invention.

BRIEF DESCRIPTION OF THE DRAWINGS

Throughout the figures of the drawing like reference numerals represent identical structure, wherein.

DETAILED DESCRIPTION

Figure 1:
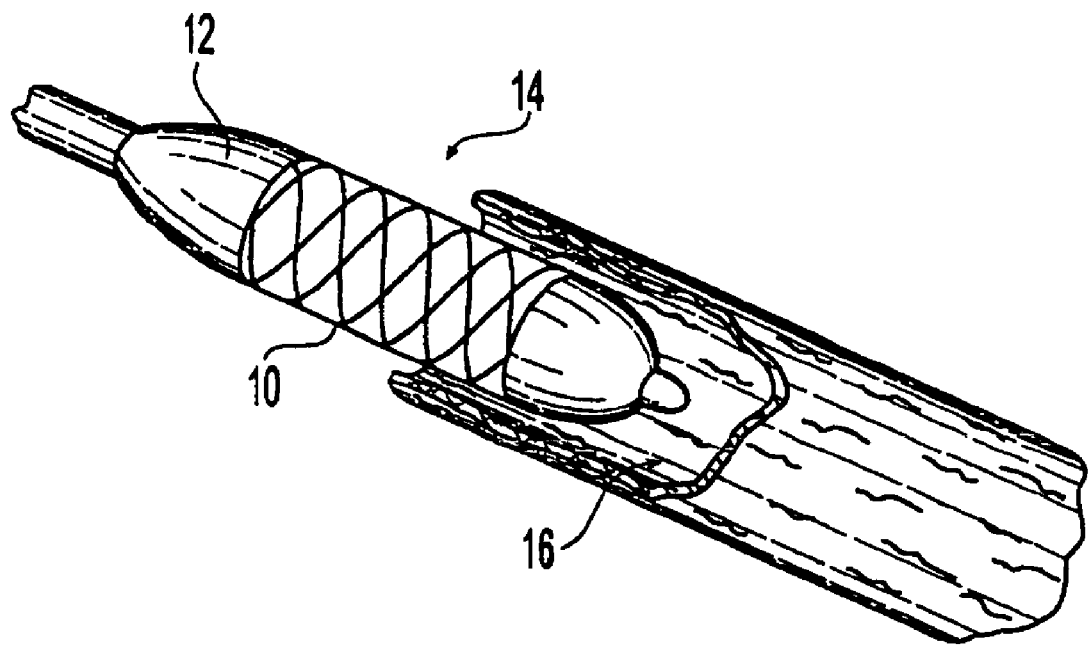
FIG. 1 shows a stent being delivered to a treatment site.

FIG. 1 shows a stent 10 which has been crimped onto an angioplasty balloon 12. The assembly 14 is being delivered to a treatment site 16 in an arterial vessel 16. In a typical intervention the stent 10 will be made of a metal mesh and this primary structure will be mechanically deformed onto a balloon after it has been coated with the drug. After insertion into the treatment site 16 the stent 10 will be deployed by expanding it into the tissues at the treatment site. The secondary coating on the surface of the primary structure will be in contact with the tissue at the treatment site and the stent will be exposed to a continuous flow of blood at the site.

Figure 2:
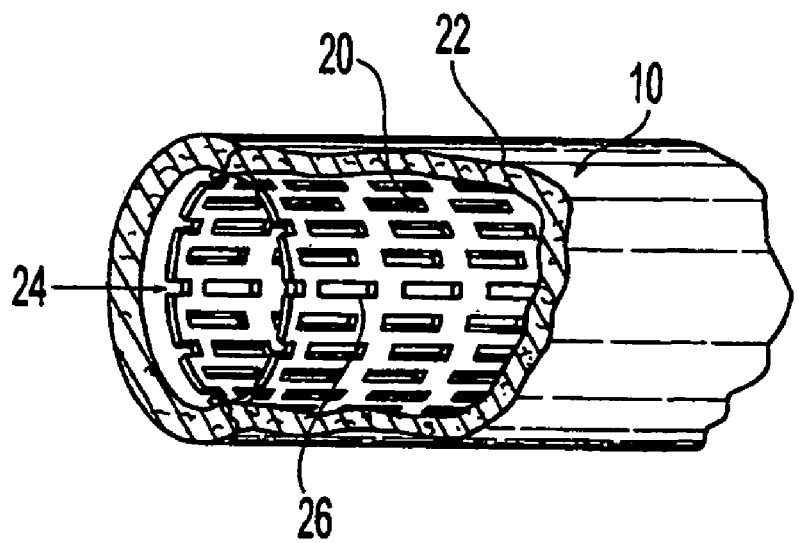
FIG. 2 shows a stent with the preferred coating applied.

FIG. 2 shows a partial cross section of a segment of the stent 10 The metal substrate 20 provides the mechanical characteristics for the stent and is the primary structure as is well known in this art. As seen in the figure the stent 10 is a hollow tube having open ends typified by open end 24 and a side wall substrate 20 with multiple apertures typified by aperture 26.

The secondary coating 22 is preferable a biodegradable polymer such as PLA carrying a concentration of the drug tacrolimus. The preferred approach is to dissolve the Tacrolimus in the selected polymer and dip coat the stent. In this preferred process the tacrolimus is uniformly distributed in the coating. It is important to note that other approaches may be adopted as well. For example the surface of the stent may be modified to exhibit porosity. This matrix may be considered a secondary coating and it may be loaded or filled with tacrolimus or a tacrolimus contains compound in another operation.

Example

The following protocol details an illustrative proposed test stent according to the invention.

Approximately 40 mg of R203, a polylactic acid of a molecular weight of 30 kDa, is dissolved in 0.6 ml chloroform together with 10 mg of tacrolimus. The resulting solution yields a weight-related content of 20% of tacrolimus in the coating.

The stents are dip-coated at reduced temperate in several steps in order to apply an approximately 10 µm thick coating on the stent surface.

Next the stents are crimped on a balloon. When used in a patient the stent will be expanded into a vessels of a patient to a maximum diameter of 4.5 mm. The expansion of the stent places the polymer matrix which is acting a secondary coating in contact with the tissues at the site of stent placement. Stents proposed for use are conventional in design and are commercially available from InFlow Dynamics (InFlow Starflex Stent Design).

Expected Mechanism of Operation and Interaction with the Body

Tacrolimus was discovered in 1984 in the culture medium of a bacterium that was detected in the soil in Japan. The bacterium was called *Streptomyces tsukubaensis*, and has shown to have interesting properties. Initially it was assumed to belong to the group of the macrolide antibiotics such as erythromycin.

Tacrolimus has a molecular weight of 822 Da, it is a white crystalline powder and it has both a lipophilic and strong hydrophobic behavior which are exploited in the invention. It is soluble in chloroform, ethylacetate acetone, and ethanol, and is practically insoluble in water. This drug is available from Fujisawa Inc. of Japan.

The approved indications for the drug vary between countries. In the US, tacrolimus is currently approved for the use in the prophylaxis of organ rejection in patients receiving liver or kidney transplant. In UK and Canada, tacrolimus is indicated for primary therapy and rescue therapy for graft rejection resistant to conventional immunosuppressive regimen and several European countries have approved the drug for heart transplantation.

The applicant has observed in restenosis that the infiltration of lymphocytes, macrophages, and plasma cells end in matrix production of smooth muscle cells.

It is believed that the production of T-helper cells and the production of cytokines are an important mechanism in the immunoresponse to a foreign body. If the stent surface is recognized as a foreign body by the CD4 identifiable helper cells ($T_{H1}$, $T_{H2}$), this induces a T-cell proliferation. The helper cells produce various cytokines such interleukine 2, interferon γ (IFNγ) that cause an activation of killer and cytotoxic T-cells as well as polynuclear granulocytes and mastcells. The mastcells themselves produce interleukine 1 and 2, which also enhance the proliferation of the T-cells. This response results in cellular cytotoxicity and antibody creation.

Interferon γ enhances the expression of intercellular adhesion molecules (ICAM1), that increases the adhesion of T-cells to the endothelial cells. This also effects a local thrombus formation on the endothelial cells and increases the endothelial permeability.

It appears the interleukine 8 especially promotes the adhesion and transepithelial migration of T-cells into the neointimal build-up. In transplant rejections, an increase in interleukine 8 production precedes the rejection of the organ by several days. In summary, the rejection of a foreign body is carried forward primarily by T lymphocytes, monocytes, macrophages, and killercells that are upregulated by a wide variety of cytokines such as interleukine 2, 4, 5, 6, 8, and 10, interferon γ, and TNFα.

When a T-cell recognizes the antigenic foreign surface then, upon activation, phospholipases (PLC) induce the generation of inositol-tri-phosphate ($IP_3$), a primarily calcium dependent signal transduction. Calcineurin diphosphorylizes the nuclear factor of activated lymphocytes in the cytoplasma (NF-ATC) and induces its translocation into the nucleus (NF-AT).

At the nucleus, this complex induces the transcription of interleukines 2, 3, 4, 5, and 8 genes as well as the transcription of TGFβ and of the tumornecrosis factor α. The transcription of the specific cytokine genes into mRNA results in the production of the respective cytokines by the T-cell.

Tacrolimus has a specific binding site in the cytoplasma. This binding protein is called FKBP-12. The binding of tacrolimus to his receptor binds to the calcineurine and inhibits the calcium dependent signal transduction. By this way, it inhibits the translocation of the cytoplasmatic NF-ATC from the cytoplasma into the nucleus and thereby the expression of the above mentioned cytokines.

TGFβ is not only released by T lymphocytes, but also by activated endothelial cells. Endothelial cells have a wide range of purposes and action. Aside from the production of the nitrogen monoxide NO, that inhibits vascular smooth muscle cell proliferation, endothelial cells are capable upon stimulation to produce also growth factors such as insuline-like growth factor (IGF1), basic fibroblast growth factor (bFGF), interleukine 6, and especially transforming growth factor β. In addition, if upon stimulation of interleukine 4, tumornecrosis factor α, and interferon γ the expression of ICAM-1 increases, the endothelial layer is more permeable to the cytokines and allows them to penetrate through the endothelial layer.

TGFβ has the capability to transit smooth muscle cells from their contractile state into its proliferative form. In this form, the cells are very secretory and produce a wide variety of intercellular matrix, among them various collagens and proteoglykanes.

Applicant believes that the primary action of tacrolimus is that it acts both as a suppressor of the inflammatory reaction against the foreign stent body and as a competitive inhibitor at the FKBP-12 receptor of smooth muscle cells and prevents them to enter the secretory state. Applicant believes that the important factor to be addressed in stent coatings is the immunoresponse toward the foreign body of the stent.

In a recent study, the different inhibitory effects of immunosuppressive drugs on human and rat aortic smooth muscle cells and endothelial cell proliferation were studied. This trial revealed that tacrolimus very modest antiproliferative properties on vascular cells. This means that the normal wound healing response is not compromised, but the transition to the secretory smooth muscle cell type that is responsible for the restenosis build up is practically totally inhibited. This is the major difference between his and other immunosuppressive drugs that inhibit all normal wound healing responses.

Also methylprednisolone showed a gradual inhibition over a broad concentration interval in rat and human smooth muscle cells, but not of human endothelial cells.

Dosage

Since only a limited amount of drug can be coated onto the surface of a stent, the most potent drug should be used. In clinical practice, the dosage for tacrolimus normally is a range of 0.04-0.06 mg/kg/day, if given intravenously. This means about 4 mg per day for a 75 kg patient are applied, a level in the whole blood of 10-20 ng/ml is the primary goal.

The dosages of cyclosporine and of mycophenolic acid which are used for immunosurpression are 10 to 100-fold higher in order to achieve similar effect.

A second aspect makes tacrolimus highly superior over cyclosporine, is its dual action on the cytokine inhibition. While cyclosporine also inhibits the cytokine release from T-cells, it has not the competitive inhibitory effect of TGFβ in smooth muscle cells, which is according to the hypothesis of this study the major action of arteriosclerosis and restenosis associated with the foreign body implant of a stent.

Tacrolimus is a lipophilic substance which is practically insoluble in water. Therefore, its distribution in the blood is primarily intracellular in red blood cells, in the plasma it is bound to α-1 sour glycoproteins and albumins. This means, that if coated to a stent the concentration in the cells will be high, while the solution into plasma is low, resulting in a high local concentration.

Previous studies with PLA-coating have shown that a thickness of 10 μm of PLA on the stent surface is favorable. This means, that on a 16 mm long stent on average 500 μg of carrier are applied by means described previously. In order not to compromise the physical characteristics of such a stent coating, a maximum of 20% of drug can be incorporated into the carrier. This means, that roughly 100 μg tacrolimus to a stent can be applied. Assuming a release over more than 10 days, the total dosage released is less than 1/1000 of the dosage given intravenously. Assuming that the majority is not released into the blood and that tacrolimus has a halflife of 12 hours, the systemic dosage released from the stent coating is $10^{5-6}$ below that what is needed for a systemic action.

Assuming a release similar to other drugs incorporated into the PLA carrier a minimum intracellular level of tacrolimus in the therapeutic range of 5-20 ng/ml tissue can be achieved in the adjacent wall.

Bio-Resorbable Coating

There is a complex reaction between the body and a material like PLA. The kinetics of this reaction governs in part the release of the tacrolimus. To test the elution it is proposed to fill 10 vials with 3 stents each are and to incubate them at 37° C. A magnetic stirrer induces a constant flow of the lipophilic solution into which the stents are immersed. Aliquots are taken at different time intervals, frozen, and subjected to high pressure liquid chromatography (HPLC) in order to detect the release level of tacrolimus and dexamethasone. Enzyme immunoassay systems that can detect down to a minimum of 0.5 ng/ml tacrolimus in the solution are to be used. Samples are taken at 1 hour, 12 hours, 24 hours, 48 hours, 6, 12, 24, and 30 days and then subjected to the assay.

Every time aliquots are taken (10 μl), the same amount of solution is added in order to keep the concentration the same.

The degradation of the PLA matrix has been tested in the past and described. In principle, at 37° C. also a magnetic stirrer tests the weight loss of stents in a saline solution. PLA degrades by hydrolysis to lactic acid. Previous calculations have shown, that if the entire amount of polymere was immediately degraded, this would result in roughly 5 μmol of lactic acid, that would be diluted in an average blood volume of 7 l. This would respond to a burden of lactic acid of about $10^{-6}$ μmol/ml lactate, well below the level of lactate present in blood after strenuous exercise (2-4 μmol/l).

Non Bio-Resorbable Coating

Non digestible coatings can be used as well. In addition to surface modification of the metal of the stent several polymer coats are contemplated. In this embodiment the polymer coating acts as an alternative to the PLA and the pharmo-kinetics related to dose administration must be tailored to provide a therapeutic dose based on the composition of the polymer. It is expected that the drug will be released though a diffusion process over a number of days. The polymer matrix should be tailored to achieve a therapeutic release. It is expected that polyurethanes and polyethylene and similar plastics will be useful in this application.

What is claimed is:

1. A stent having at least a portion which is implantable into the body of a subject comprising a surface and a coating comprising tacrolimus and a polymer, wherein at least a part of the stent is metallic and the coating is disposed on at least part of the metallic stent portion, and wherein the coating is formulated to deliver an intracellular level of tacrolimus in adjacent tissue of about 5 ng/ml of tissue to about 20 ng/ml of tissue while providing a systemic dosage that is $10^{5-6}$ lower than needed for a systemic action.

2. The stent of claim 1, wherein the surface is porous.

3. The stent of claim 1, wherein the tacrolimus is uniformly distributed in the coating.

4. The stent of claim 1, wherein the coating comprises 20% by weight of tacrolimus.

5. The stent of claim 1, wherein the coating has a thickness of about 10 μm.

6. The stent of claim 1, wherein the dosage prevents conversion of smooth muscle cells at the stent implantation site to secretory smooth muscle cell types.

7. The stent of claim 1, wherein the polymer is non-biodegradable.

8. The stent of claim 1, wherein the polymer is biodegradable.

9. The stent of claim 1, wherein the polymer forms a biocompatible matrix to allow elution of the tacrolimus.

10. A method of preventing restenosis by implanting the stent of claim 1 into a body lumen.

11. A stent having at least a portion which is implantable into the body of a subject comprising an open-ended metallic tubular structure having a sidewall with apertures therein, wherein the sidewall comprises an outer surface having a coating disposed thereon, wherein the coating is formulated to deliver an intracellular level of tacrolimus in adjacent tissue of about 5 ng/ml of tissue to about 20 ng/ml of tissue while providing a systemic dosage that is $10^{5-6}$ lower than needed for a systemic.

12. The stent of claim 11, wherein the dosage prevents conversion of smooth muscle cells at the stent implantation site to secretory smooth muscle cell types.

13. The stent of claim 11, wherein the polymer is non-biodegradable.

14. A method of preventing restenosis by implanting the stent of claim 11 into a body lumen.

15. The stent of claim 11, wherein the surface is porous.

16. The stent of claim 11, wherein the tacrolimus is uniformly distributed in the coating.

17. The stent of claim 11, wherein the coating comprises 20% by weight of tacrolimus.

18. The stent of claim 11, wherein the coating has a thickness of about 10 μm.

19. Ten stent of claim 11, wherein the polymer is biodegradable.

20. The stent of claim 11, wherein the polymer forms a biocompatible matrix to allow elution of the tacrolimus.

* * * * *